(12) United States Patent
Kemp et al.

(10) Patent No.: US 10,676,746 B2
(45) Date of Patent: Jun. 9, 2020

(54) METHODS FOR IDENTIFYING THERAPEUTIC TARGETS AND TREATING MONITORING CANCERS

(71) Applicant: Fred Hutchinson Cancer Research Center, Seattle, WA (US)

(72) Inventors: Christopher Kemp, Seattle, WA (US); Carla Grandori, Seattle, WA (US); Eduardo Mendez, Seattle, WA (US); Russell Moser, Seattle, WA (US); Chang Xu, Mercer Island, WA (US)

(73) Assignee: Fred Hutchinson Cancer Research Center, Seattle, WA (US)

( * ) Notice: Subject to any disclaimer, the term of this patent is extended or adjusted under 35 U.S.C. 154(b) by 589 days.

(21) Appl. No.: 15/038,342

(22) PCT Filed: Nov. 21, 2014

(86) PCT No.: PCT/US2014/066884
§ 371 (c)(1),
(2) Date: May 20, 2016

(87) PCT Pub. No.: WO2015/077602
PCT Pub. Date: May 28, 2015

(65) Prior Publication Data
US 2016/0289686 A1 Oct. 6, 2016

Related U.S. Application Data

(60) Provisional application No. 61/907,943, filed on Nov. 22, 2013.

(51) Int. Cl.
| | |
|---|---|
| *C12N 15/11* | (2006.01) |
| *C12N 15/113* | (2010.01) |
| *C12Q 1/6886* | (2018.01) |
| *A61K 45/06* | (2006.01) |
| *A61K 31/519* | (2006.01) |
| *A61K 33/24* | (2019.01) |
| *G01N 33/50* | (2006.01) |
| *A61K 31/426* | (2006.01) |
| *A61K 31/4535* | (2006.01) |
| *A61K 31/407* | (2006.01) |
| *A61K 31/5377* | (2006.01) |
| *A61K 31/506* | (2006.01) |
| *A61K 31/713* | (2006.01) |

(52) U.S. Cl.
CPC ........ *C12N 15/1137* (2013.01); *A61K 31/407* (2013.01); *A61K 31/426* (2013.01); *A61K 31/4535* (2013.01); *A61K 31/506* (2013.01); *A61K 31/519* (2013.01); *A61K 31/5377* (2013.01); *A61K 31/713* (2013.01); *A61K 33/24* (2013.01); *A61K 45/06* (2013.01); *C12Q 1/6886* (2013.01); *G01N 33/5011* (2013.01); *C12N 2310/14* (2013.01); *C12Q 2600/106* (2013.01); *C12Q 2600/136* (2013.01); *C12Q 2600/156* (2013.01); *C12Q 2600/158* (2013.01); *G01N 2800/52* (2013.01)

(58) Field of Classification Search
None
See application file for complete search history.

(56) References Cited

U.S. PATENT DOCUMENTS

| | | |
|---|---|---|
| 9,273,317 B2 | 3/2016 | Toyoshima et al. |
| 9,801,853 B2 | 10/2017 | Grandori et al. |
| 10,188,630 B2 | 1/2019 | Grandori et al. |
| 2005/0002998 A1 | 1/2005 | Chang et al. |
| 2007/0099209 A1 | 5/2007 | Clarke et al. |
| 2007/0105114 A1 | 5/2007 | Li et al. |
| 2010/0179154 A1 | 7/2010 | Almario Garcia et al. |
| 2013/0065939 A1 | 3/2013 | Judge et al. |
| 2013/0115309 A1 | 5/2013 | Grandori et al. |
| 2015/0148401 A1 | 5/2015 | Toyoshima et al. |
| 2016/0367572 A1 | 12/2016 | Toyoshima et al. |
| 2018/0110788 A1 | 4/2018 | Toyoshima et al. |
| 2018/0153858 A1 | 6/2018 | Grandori et al. |

FOREIGN PATENT DOCUMENTS

| | | |
|---|---|---|
| FR | 2918061 A1 | 1/2009 |
| JP | 2007-513940 A | 5/2007 |
| WO | WO 2004/035076 A1 | 4/2004 |
| WO | WO 2005/056043 A2 | 6/2005 |
| WO | WO 2009/016286 A2 | 2/2009 |
| WO | WO 2009/145815 A2 | 12/2009 |
| WO | WO 2010/111712 A2 | 9/2010 |
| WO | WO 2011/127202 A2 | 10/2011 |
| WO | WO 2013/023084 A2 | 2/2013 |
| WO | WO 2015/077602 A1 | 5/2015 |

OTHER PUBLICATIONS

Yilmaz et al., Therapeutic targeting of Trk suppresses tumor proliferation and enhances cisplatin activity in HNSCC, Cancer Biology & Therapy, vol. 10, pp. 644-653. (Year: 2010).*
Sweeny et al., Inhibition of fibroblasts reduced head and neck cancer growth by targeting fibroblast growth factor receptor, The Laryngoscope, vol. 122, pp. 1539-1544. (Year: 2012).*
Namiki et al., AMP kinase-related kinase NUAK2 affects tumor growth, migration, and clinical outcome of human melanoma, PNAS, vol. 108, pp. 6597-6602. (Year: 2011).*
Aguissa-Touréet al., Genetic alterations of PTEN in human melanoma, Cellular and Molecular Life Sciences, vol. 69, pp. 1475-1491. (Year: 2012).*
Gradiz et al., MIA PaCa-2 and PANC-1—pancreas ductal adenocarcinoma cell lines with neuroendocrine differentiation and somatostatin receptors, Scientific Reports, vol. 6:21648, pp. 1-14. (Year: 2016).*

(Continued)

*Primary Examiner* — Dana H Shin
(74) *Attorney, Agent, or Firm* — Cooley LLP

(57) ABSTRACT

The present invention provides methods for treating cancers having a mutation in one or more tumor suppressor genes, comprising providing to a subject in need thereof an inhibitor of a kinase, as well as related methods and compositions.

10 Claims, 29 Drawing Sheets

Specification includes a Sequence Listing.

(56) References Cited

OTHER PUBLICATIONS

Aarts et al. "Forced Mitotic Entry of S-Phase Cells as a Therapeutic Strategy Induced by Inhibition of WEE1", *Cancer Discovery* (2012), 2: 524-539. Published Online First Apr. 23, 2012; doi: 10.1158/2159-8290.CD-11-0320.
Agochiya et al. "Increased dosage and amplification of the focal adhesion kinase gene in human cancer cells", *Oncogene* (1999), 18(41): 5646-5653.
Annibali, Daniela, et al. "Myc inhibition is effective against glioma and reveals a role for Myc in proficient mitosis." Nature Communications (2014); 5: 4632, 11 pages.
Arabi et al. "c-Myc associates with ribosomal DNA and activates RNA polymerase I transcription", *Nat Cell Biol* (2005), 7(3): 303-310.
Armstrong, Stephen R., et al. "Distinct genetic alterations occur in ovarian tumor cells selected for combined resistance to carboplatin and docetaxel." Journal of Ovarian Research (2012); 5.1: 1-20.
Barna et al. "Suppression of Myc oncogenic activity by ribosomal protein haploinsufficiency", *Nature* (2008), 456(7224): 971-975.
Bartz et al. "Small interfering RNA screens reveal enhanced cisplatin cytotoxicity in tumor cells having both BRCA network and TP53 disruptions", *Molecular and Cellular Biology* (2006), 26(24): 9377-9386.
Behrend et al. "IC261, a specific inhibitor of the protein kinases casein kinase 1-delta and -epsilon, triggers the mitotic checkpoint and induces p53-dependent postmitotic effects", *Oncogene* (2000), 19(47): 5303-5313.
Benanti et al. "Epigenetic down-regulation of ARF expression is a selection step in immortalization of human fibroblasts by c-Myc", *Mol Cancer Res* (2007), 5(11): 1181-1189. Published Online First Nov. 2, 2007; doi: 10.1158/1541-7786.MCR-06-0372.
Benanti and Galloway. "Normal human fibroblasts are resistant to RAS-induced senescence", *Molecular and Cellular Biology* (2004), 24(7): 2842-2852.
Berns, et al. "C-myc Amplification is a Better Prognostic Factor than HER2/neu Amplification in Primary Breast Cancer", *Cancer Res* (1992), 52(5): 1107-1113.
Biechele et al. "Transcription-Based Reporters of Wnt/β-Catenin Signaling", *Cold Spring Harb Protoc* (2009), 4(Issue 6): 1-8. doi:10.1101/pdb.prot5223.
Birmingham et al. "Statistical methods for analysis of high-throughput RNA interference screens", *Nat. Methods.* (2009), 6(8): 569-575.
Blancato et al. "Correlation of amplification and overexpression of the c-myc oncogene in high-grade breast cancer: FISH, in situ hybridization and immunohistochemical analyses", *British Journal of Cancer* (2004), 90(8): 1612-1619.
Boon et al. "N-myc enhances the expression of a large set of genes functioning in ribosome biogenesis and protein synthesis", *The EMBO Journal* (2001), 20(6):1383-1393.
Bridges et al. "MK-1775, a Novel Wee1 Kinase Inhibitor, Radiosensitizes p53-Defective Human Tumor Cells", *Clinical Cancer Research* (2011), 17(17): 5638-5648. Published Online First Jul. 28, 2011; doi: 10.1158/1078-0432.CCR-11-0650.
Brockschmidt et al. "Anti-apoptotic and growth-stimulatory functions of CK1 delta and epsilon in ductal adenocarcinoma of the pancreas are inhibited by IC261 in vitro and in vivo", *Gut* (2008), 57(6): 799-806 Epub Jan. 18, 2008.
Cai, Guoqing, et al. "Phosphorylation of glycogen synthase kinase-3 ss at serine 9 confers cisplatin resistance in ovarian cancer cells." International Journal of Oncology (2007); 31.3: 657-662.
Campaner, et al. "Cdk2 suppresses cellular senescence induced by the c-myc oncogene", *Nat Cell Biol* (2010), 12(1): 54-59 (sup pp. 51-14).
Cermelli, Silvia, et al. "Synthetic lethal screens as a means to understand and treat MYC-driven cancers." Cold Spring Harbor Perspectives in Medicine (2014); 4.3 : a014209.

Chen, et al. "Overexpression of c-Myc were observed in 66% of Epithelial Ovarian Cancers (EOCs)", *Int J Gynecol Cancer* (2005), 15(5): 878-883.
Cheong et al. "IC261 induces cell cycle arrest and apoptosis of human cancer cells via CK1δ/ε and Wnt/β-catenin independent inhibition of mitotic spindle formation", *Oncogene* (2011), 30: 2558-2569.
Chiao et al. "Susceptibility to ras oncogene transformation is coregulated with signal transduction through growth factor receptors", *Oncogene* (1991), 6(5): 713-720.
Chung, et al. "MicroRNA-21 promotes the ovarian teratocarcinoma PA1 cell line by sustaining cancer stem/progenitor populations in vitro", *Stem Cell Research & Therapy* (2013), 4(88): 1-10.
Chung et al. "Median Absolute Deviation to Improve Hit Selection for Genome-Scale RNAi Screens", *Journal of Biomolecular Screening* (2008), 13(2): 149-158.
Cole et al. "RNAi screen of the protein kinome identifies checkpoint kinase 1 (CHK1) as a therapeutic target in neuroblastoma," *Proceedings of the National Academy of Sciences* (2011), 108(8): 3336-3341.
Cowling and Cole. "Turning the Tables: Myc Activates Wnt in Breast Cancer", *Cell Cycle* (2007), 6(21): 2625-2627.
Cowling, Victoria H., et al. "c-Myc transforms human mammary epithelial cells through repression of the Wnt inhibitors DKK1 and SFRP1." Molecular and Cellular Biology(2007); 27.14: 5135-5146.
Dar et al. "Aurora Kinase Inhibitors—Rising Stars in Cancer Therapeutics?", *Molecular Cancer Therapy* (2010), 9(2): 268-278. Published Online First Feb. 2, 2010; doi: 10.1158/1535-7163.MCT-09-0765.
Darcy et al. "Prognostic relevance of c-MYC gene amplification and polysomy for chromosome 8 in suboptimally-resected, advanced stage epithelial ovarian cancers: A Gynecologic Oncology Group study", *Gynecologic Oncology* (2009), 114(3): 472-479.
De Witt Hamer et al. "WEE1 Kinase Targeting Combined with DNA-Damaging Cancer Therapy Catalyzes Mitotic Catastrophe", *Clinical Cancer Research* (2011), 17: 4200-4207. Published Online First May 11, 2011.
Debnath et al. "rlk/TXK Encodes Two Forms of a Novel Cysteine String Tyrosine Kinase Activated by Src Family Kinases", *Molecular and Cellular Biology*(1999), 19(2): 1498-1507.
Doles and Hemann. "Nek4 Status Differentially Alters Sensitivity to Distinct Microtubule Poisons", *Cancer Research* (2010), 70: 1033-1041.
Dominguez-Sola et al. "Non-transcriptional control of DNA replication by c-Myc", *Nature* (2007), 448(7152): 445-451.
Egloff and Grandis. "Targeting epidermal growth factor receptor and SRC pathways in head and neck cancer", *Semin Oncol.* (2008), 35(3): 286-297.
EP Patent Application No. 11766677.6, Supplemental European Search Report, dated Oct. 7, 2013.
EP Patent Application No. 11766677.6, EPO Communication dated Jul. 10, 2014.
EP Patent Application No. 12772551.3, EPO Communication dated Jul. 30, 2015.
EP Patent Application No. 12772551.3, EPO Communication dated Jun. 21, 2016.
EP Patent Application No. 11766677.6, EPO Communication dated Feb. 5, 2016.
Firestein, et al. "CDK8 is a colorectal cancer oncogene that regulates β-catenin activity", *Nature* (2008), 455(7212): 547-551.
Fuja et al. "Somatic Mutations and Altered Expressions of the Candidate Tumor Suppressors CSNK1ε, DLG1, and EDD/hHYD in Mammary Ductal Carcinoma", *Cancer Research* (2004), 64: 942-951.
Goga et al. "Inhibition of CDK1 as a potential therapy for tumors over-expressing MYC", *Nature Medicine* (2007), 13(7): 820-827.
Grandori et al. "c-Myc binds to human ribosomal DNA and stimulates transcription of rRNA genes by RNA polymerase I", *Nat. Cell. Biol.* (2005), 7(3): 311-318.
Grandori et al. "Myc-Max heterodimers activate a DEAD box gene and interact with multiple E box-related sites in vivo", *The EMBO Journal* (1996), 15(16): 4344-4357.

(56) References Cited

OTHER PUBLICATIONS

Grandori et al. "Werner syndrome protein limits MYC-induced cellular senescence", *Genes & Development* (2003), 17(13): 1569-1574.

Greer and Rubin. "Casein kinase 1 delta functions at the centrosome to mediate Wnt-3a-dependent neurite outgrowth", *J. Cell. Biol.* (2011), 192(6): 993-1004.

Grinshtein et al. "Small Molecule Kinase Inhibitor Screen Identifies Polo-Like Kinase 1 as a Target for Neuroblastoma Tumor-Initiating Cells", Cancer Research, 71: 1385-1395 (2011) Published Online First Feb. 8, 2011; doi: 10.1158/0008-5472.CAN-10-2484.

Hanks and Hunter. "The eukaryotic protein kinase superfamily: kinase (catalytic domain structure and classification", *The FASEB Journal* (1995), 9: 576-596.

Hanson et al. "Effects of c-myc Expression on Cell Cycle Progression", *Molecular and Cellular Biology* (1994), 14(9): 5748-5755.

Haque, Azizul, et al. "Induction of apoptosis and immune response by all-trans retinoic acid plus interferon-gamma in human malignant glioblastoma T98G and U87MG cells." Cancer Immunology, Immunotherapy (2007); 56.5: 615-625.

Haque, Azizul, et al. "Emerging role of combination of all-trans retinoic acid and interferon-gamma as chemoimmunotherapy in the management of human glioblastoma." Neurochemical Research (2007); 32.12: 2203-2209.

Harsha et al. "A Compendium of Potential Biomarkers of Pancreatic Cancer", *PLOS Medicine* (2009), 6(4): e1000046, 1-6.

Hirai et al. "Small-molecule inhibition of Wee1 kinase by MK-1775 selectively sensitizes p53-deficient tumor cells to DNA-damaging agents", *Molecular Cancer Therapeutics* (2009), 8(11): 2992-3000. Published Online First Nov. 3, 2009; doi: 10.1158/1535-7163.MCT-09-0463.

Hirvonen, H. E., et al. "Differential expression of myc, max and RB1 genes in human gliomas and glioma cell lines." British journal of cancer 69.1 (1994): 16.

Hopkins and Groom. "The druggable genome", *Nat Rev Drug Discov* (2002), 1(9): 727-730.

Iba et al., "Expression of the c-myc gene as a predictor of chemotherapy response and a prognostic factor in patients with ovarian cancer", Cancer Science (2004), 95(5): 418-423.

Iorns, Elizabeth, et al. "CRK7 modifies the MAPK pathway and influences the response to endocrine therapy." Carcinogenesis (2009); 30.10: 1696-1701.

Japanese Patent Application No. 2013-503928, Notice of Reasons for Rejection dated Mar. 20, 2015 (with English translation).

Japanese Patent Application No. 2013-503928, Notice of Reasons for Rejection dated Feb. 29, 2016 (with English translation).

Jenkins et al. "Detection of c-myc oncogene amplification and chromosomal anomalies in metastatic prostatic carcinoma by fluorescence in situ hybridization", Cancer Research (1997), 57(3): 524-531.

Jones et al. "Core signaling pathways in human pancreatic cancers revealed by global genomic analyses", *Science* (2008), 321(5897): 1801-1806.

Katayama and Sen. "Aurora kinase inhibitors as anticancer molecules", *Biochim Biophys Acta.* (2010), 1799(10-12): 829-839. doi: 10.1016/j.bbagrm.2010.09.004. Epub Sep. 20, 2010.

Kikuchi et al. "Treatment options in the management of ovarian cancer", *Expert Opinion on Pharmacotherapy* (2005), 6(5): 743-754.

Kim et al. "CK1ε is required for breast cancers dependent on β-catenin activity", *PLoS One* (2010), 5(2): e8979, 1-10.

Kiyono et al. "Both Rb/p16$^{INK4a}$ inactivation and telomerase activity are required to immortalize human epithelial cells", Nature (1998), 396(6706): 84-88.

Kozma et al. "Investigation of c-myc oncogene amplification in colorectal cancer", Cancer Letters (1994), 81(2): 165-169.

Li et al., "Down-regulation of pescadillo inhibits proliferation and tumorigenicity of breast cancer cells", Cancer Science (2009), 100(12): 2255-2260.

Li, Chi-Ming, et al. "PEG10 is a c-MYC target gene in cancer cells." Cancer Research (2006); 66.2: 665-672.

Luoto et al. "Tumor cell kill by c-MYC depletion: role of MYC-regulated genes that control DNA double-strand break repair", Cancer Research (2010), 70(21): 8748-8759. Published Online First Oct. 12, 2010; DOI: 10.1158/0008-5472.CAN-10-0944.

Lutz et al. "Conditional expression of N-myc in human neuroblastoma cells increases expression of α-prothymosin and ornithine decarboxylase and accelerates progression into S-phase early after mitogenic stimulation of quiescent cells," *Oncogene* (1996), 13(4): 803-812.

Ma et al. "Death by releasing the breaks: CHK1 inhibitors as cancer therapeutics", *Trends Mol Med.* (2011), 17(2): 88-96. doi: 10.1016/j.molmed.2010.10.009. Epub Nov. 17, 2010.

Major, et al. "New Regulators of Wnt/β-Catenin Signaling Revealed by Integrative Molecular Screening", *Science Signaling* (2008), 1(45): ra12, 1-11.

Malynn et al. "N-myc Can Functionally Replace c-myc in Murine Development, Cellular Growth, and Differentiation", *Genes & Development* (2000), 14: 1390-1399.

Mano et al. "Tec protein-tyrosine kinase is an effector molecule of Lyn protein-tyrosine kinase", *FASEB* (1996), 10: 637-42.

Marcu et al. "Myc function and regulation", *Ann. Rev. Biochem.* (1992), 61: 809-860.

Mashhoon et al. "Crystal Structure of a Conformation- Selective Casein Kinase-1 Inhibitor", *The Journal of Biological Chemistry* (2000), 275(26): 20052-20060.

McMahon et al. "The essential cofactor TRRAP recruits the histone acetyltransferase hGCN5 to c-Myc", *Molecular & Cellular Biology* (2000), 20(2): 556-562.

The Merck Manual, 18th edition, Japanese ver., 2005, [online], Retrieved from the internet:, with Enbglish summary/translation, 3 pages <URL:http://merckmanual.jp/mmpej/sec19/ch285/ch285b.html>.

Mestdagh et al. "MYCN/c-MYC-induced microRNAs repress coding gene networks associated with poor outcome in MYCN/c-MYC-activated tumors", *Oncogene* (2010), 29(9): 1394-1404.

Mitani et al. "Analysis of c-myc DNA amplification in non-small cell lung carcinoma in comparison with small cell lung carcinoma using polymerase chain reaction", *Clin Exp Med* (2001), 1(2): 105-111.

Moniz et al. "Nek family of kinases in cell cycle, checkpoint control and cancer", *Cell Division* (2011) 6: 18, 10 pages.

Moses et al., "Intended transcriptional silencing with siRNA results in gene repression through sequence-specific off-targeting", RNA (2010), 16: 430-441. Published in Advance Dec. 21, 2009, doi: 10.1261/rna.1808510.

Nguyen et al. "Nek4 regulates entry into replicative senescence and the response to DNA damage in human fibroblasts", *Molecular and Cellular Biology* (2012), 32: 3963-3977.

Nikiforov et al. "TRRAP-Dependent and TRRAP-Independent Transcriptional Activation by Myc Family Oncoproteins", *Molecular and Cellular Biology* (2002), 22(14): 5054-5063.

Park et al. "Neuroblastoma: Biology, Prognosis and Treatment", *Pediatric Clinics of North America* (2008), 55: 97-120.

PCT/US2011/031460, International Search Report, dated Dec. 20, 2011.

PCT/US2011/031460, Written Opinion of the International Searching Authority, dated Dec. 20, 2011.

PCT/US2011/031460, International Preliminary Report on Patentability, dated Oct. 9, 2012.

PCT/US2012/050186, International Search Report, dated Apr. 18, 2013.

PCT/US2012/050186, Written Opinion of the International Searching Authority, dated Apr. 18, 2013.

PCT/US2012/050186, International Preliminary Report on Patentability, dated Feb. 11, 2014.

PCT/US2014/066884, International Search Report, dated Apr. 30, 2015.

PCT/US2014/066884, Written Opinion of the International Searching Authority, dated Apr. 30, 2015.

PCT/US2014/066884, International Preliminary Report on Patentability, dated May 24, 2016.

(56) References Cited

OTHER PUBLICATIONS

Poeta et al. "TP53 Mutations and Survival in Squamous-Cell Carcinoma of the Head and Neck", *N Engl J Med.* (2007), 357(25): 2552-2561.
Popadiuk, Cathy M., et al. "Antisense suppression of pygopus2 results in growth arrest of epithelial ovarian cancer." Clinical Cancer Research (2006); 12.7: 2216-2223.
Rajeshkumar et al. "MK-1775, a Potent Wee1 Inhibitor, Synergizes with Gemcitabine to Achieve Tumor Regressions, Selectively in p53-Deficient Pancreatic Cancer Xenografts", *Clinical Cancer Research* (2011), 17: 2799-2806. Published Online First Mar. 9, 2011; doi: 10.1158/1078-0432.CCR-10-2580.
Ray, et al. "Myc Can Induce DNA Breaks In vivo and In vitro Independent of Reactive Oxygen Species", *Cancer Research* (2006), 66(13): 6598-6605.
Regan et al. "Hsp90 inhibition increases p53 expression and destabilizes MYCN and MYC in neuroblastoma", *International Journal of Oncology* (2011), 32(1): 105-112.
Riley et al. "A Systematic Review of Molecular and Biological Tumor Markers in Neuroblastoma", *Clinical Cancer Research* (2004), 10: 4-12.
Robinson, et al. "c-Myc Accelerates S-Phase and Requires WRN to Avoid Replication Stress", PLoS One (2009), 4(6): e5951, 1-10.
Russo et al. "c-myc Down-Regulation Induces Apoptosis in Human Cancer Cell Lines Exposed to RPR-115135 ($C_{31}H_{29}NO_4$), a Non-Peptidomimetic Farnesyltransferase Inhibitor", *Journal of Pharmacology and Experimental Therapeutics* (2002), 304(1): 37-47.
Sakanaka, "Phosphorylation and Regulation of β-Catenin by Casein Kinase Iε", J Biochem (2002), 132: 697-703.
Sarraf et al. "The human ovarian teratocarcinoma cell line PA-1 demonstrates a single translocation: analysis with fluorescence in situ hybridization, spectral karyotyping, and bacterial artificial chromosome microarray", *Cancer Genetics and Cytogenetics* (2005), 161(1): 63-69.
Sasaki et al. "A binding site for Gli proteins is essential for HNF-3β floor plate enhancer activity in transgenics and can respond to Shh in vitro", *Development* (1997), 124: 1313-1322.
Sato et al. "Fluorescence in situ hybridization analysis of c-myc amplification in stage $T_3N_0M_0$ prostate cancer in Japanese patients", *International Journal of Urology* (2006), 13(6): 761-766.
Schleger et al. "c-MYC Activation in Primary and Metastatic Ductal Adenocarcinoma of the Pancreas: Incidence, Mechanisms, and Clinical Significance", *Modern Pathology* (2002), 15(4): 462-469.
Smal et al. "Casein kinase 1 delta activates human recombinant deoxycytidine kinase by Ser-74 phosphorylation, but is not involved in the in vivo regulation of its activity." Archives of Biochemistry and Biophysics (2010); 502: 44-52.
Soucek et al. "Modelling Myc inhibition as a cancer therapy", *Nature* (2008), 455(7213): 679-683.
Stabile et al. "c-Src Activation Mediates Erlotinib Resistance in Head and Neck Cancer by Stimulating c-Met", *Clinical Cancer Research* (2013), 19(2): 380-392. Published Online First, Dec. 4, 2012. doi: 10.1158/1078-0432.CCR-12-1555.
Swiatek, Wojciech, et al. "Regulation of casein kinase Iε activity by Wnt signaling." Journal of Biological Chemistry (2004); 279.13: 13011-13017.
Tainsky et al. "PA-1, A Human Cell Model for Multistage Carcinogenesis: Oncogenes and Other Factors", *Anticancer Research* (1988), 8(5A): 899-914.
Takahashi et al. "Amplification of c-myc and cyclin D1 genes in primary and metastatic carcinomas of the liver", *Pathology International* (2007), 57(7): 437-442.
Tashiro, et al. "c-myc Over-Expression in Human Primary Ovarian Tumours: Its Relevance to Tumour Progression", *Int. J. Cancer,* 50: 828-833 (1992).
Toyoshima et al. "Functional genomics identifies therapeutic targets for MYC-driven Cancer" PNAS, 109(24): 9545-9550 (2012).
Trumpp et al. "c-Myc regulates mammalian body size by controlling cell number but not cell size", *Nature* (2001), 414(6865): 768-773.

U.S. Appl. No. 13/639,258, Office Action dated Aug. 15, 2013.
U.S. Appl. No. 13/639,258, Office Action dated Jan. 16, 2014.
U.S. Appl. No. 13/639,258, Office Action dated Sep. 9, 2014.
U.S. Appl. No. 13/639,258, Office Action dated Jan. 5, 2015.
U.S. Appl. No. 13/639,258, Advisory Action dated Mar. 25, 2015.
U.S. Appl. No. 13/639,258, Office Action dated Nov. 16, 2015.
U.S. Appl. No. 13/639,258, Office Action dated Jun. 6, 2016.
U.S. Appl. No. 13/639,258, Advisory Action dated Aug. 17, 2016.
U.S. Appl. No. 14/237,838, Office Action dated Mar. 11, 2015.
U.S. Appl. No. 15/000,933, Office Action dated Nov. 30, 2016.
Valsesia-Wittmann et al., "Oncogenic cooperation between H-Twist and N-Myc overrides failsafe programs in cancer cells", *Cancer Cell,* 6(6): 625-630 (2004).
Van Linden et al. "Inhibition of Wee1 Sensitizes Cancer Cells to Antimetabolite Chemotherapeutics In Vitro and In Vivo, Independent of p53 Functionality", *Molecular Cancer Therapy* (2013), 12: 2675-2684. Published Online First Oct. 11, 2013; doi: 10.1158/1535-7163.MCT-13-0424.
Wada, Randal K., et al. "Interferon-γ and retinoic acid down-regulate N-myc in neuroblastoma through complementary mechanisms of action." Cancer Letters (1997); 121.2: 181-188.
Walton et al. "Selective Inhibition of Casein Kinase 1ε Minimally Alters Circadian Clock Period", *Journal of Pharmacology and Experimental Therapeutics* (2009), 330(2): 430-439.
Wang et al. "Improved low molecular weight Myc-Max inhibitors", *Molecular Cancer Therapy* (2007), 6(9): 2399-2408.
Wang et al. "Increased radio-resistance and accelerated B cell lymphomas in mice with Mdmx mutations that prevent modifications by DNA-damage-activated kinases", *Cancer Cell* (2009), 16(1): 33-43.
Wang, Yi-hua, et al. "Knockdown of c-Myc expression by RNAi inhibits MCF-7 breast tumor cells growth in vitro and in vivo." Breast Cancer Research 7.2 (2004): 1.
Weber et al. "Retinoic acid-mediated growth inhibition of small cell lung cancer cells is associated with reduced myc and increased $p27^{Kip1}$ Expression", International Journal of Cancer (1999), 80(6): 935-943.
Weiss et al. "Targeted Expression of MYCN Causes Neuroblastoma in Transgenic Mice", *The EMBO Journal* (1997), 16(11): 2985-2995.
Wen et al. "Knockdown of p21-activated Kinase 6 Inhibits Prostate Cancer Growth and Enhances Chemosensitivity to Docetaxel", Urology (2009), 73(6): 1407-1411.
Wheeler et al. "Lyn Kinase Mediates Cell Motility and Tumor Growth in EGFRvIII-Expressing Head and Neck Cancer", *Clinical Cancer Research* (2012), 18: 2850-2860. Published Online First Apr. 6, 2012; doi: 10.1158/1078-0432.CCR-11-2486.
Wright, Kim, et al. "β-Catenin mutation and expression analysis in ovarian cancer: Exon 3 mutations and nuclear translocation in 16% of endometrioid tumours." International Journal of Cancer (1999); 82.5: 625-629.
Wu et al. "Amplification and Overexpression of the L-MYC Proto-Oncogene in Ovarian Carcinomas", *American Journal of Pathology* (2003), 162(5): 1603-1610.
Xi et al. "SRC kinases mediate STAT growth pathways in squamous cell carcinoma of the head and neck", *J Biol Chem.* (2003), 278(34): 31574-31583. First Published Online May 27, 2003, doi: 10.1074/jbc.M303499200.
Xu et al. "Integrative analysis of DNA copy number and gene expression in metastatic oral squamous cell carcinoma identifies genes associated with poor survival", *Molecular Cancer* (2010), 9: 143, 12 pages.
Xu et al. "Integrative genomics in combination with RNA interference identifies prognostic and functionally relevant gene targets for oral squamous cell carcinoma", *PLOS Genetics* (2013), 9(1): e1003169. doi: 10.1371/journal.pgen.1003169.
Rinsho Yakuri, Clinical Pharmacology, Mar. 2010, vol. 41, No. 2, p. 23S-24S (with English summary/translation of pertinent portions).
Yang and Stockwell. "Inhibition of casein kinase 1-epsilon induces cancer-cell-selective, PERIOD2-dependent growth arrest", *Genome Biology* (2008), 9(6): R92, 1-13.

(56) References Cited

OTHER PUBLICATIONS

Zhang et al. "A Simple Statistical Parameter for Use in Evaluation and Validation of High Throughput Screening Assays", *Journal of Biomolecular Screening* (1999), 4(2): 67-73.

Zhang et al. "SRC family kinases mediate epidermal growth factor receptor ligand cleavage, proliferation, and invasion of head and neck cancer cells", *Cancer Research* (2004), 64: 6166-6173.

Zhou et al. "Overexpression of Cyclin D1 Enhances Gene Amplification", *Cancer Research* (1996), 56: 36-39.

Bell, et al., "Integrated genomic analyses of ovarian carcinoma." Nature (2011); 474(7353): 609-615 (and Erratum).

Benson, et al., "A phase I trial of the selective oral cyclin-dependent kinase inhibitor seliciclib (CYC202; R-Roscovitine), administered twice daily for 7 days every 21 days." British Journal of Cancer (2007); 96(1): 29-37.

Bösken, et al., "The structure and substrate specificity of human Cdk12/Cyclin K." Nature Communications (2014); Article No. 3505, 14 pages.

Delehouze, et al., "CDK/CK1 inhibitors roscovitine and CR8 downregulate amplified MYCN in neuroblastoma cells." Oncogene (2014); 33(50): 5675-5687.

Lee, et al., "Resveratrol Suppresses Growth of Human Ovarian Cancer Cells in Culture and in a Murine Xenograft Model: Eukaryotic Elongation Factor 1A2 as a Potential Target." Cancer Research (2009); 69(18): 7449-7458.

Markman and Bookman, et al., "Second-line treatment of ovarian cancer." The Oncologist (2000); 5(1): 26-35.

PCT/US2012/050186, Invitation to Pay Additional Fees, dated Feb. 5, 2013, 7 pages.

PCT/US2014/066884, Invitation to Pay Additional Fees, dated Mar. 11, 2015, 4 pages.

Pelengaris and Khan, "The c-MYC oncoprotein as a treatment target in cancer and other disorders of cell growth." Expert Opin. Ther. Targets (2003); 7(5): 623-642.

U.S. Appl. No. 15/604,993, Office Action dated Feb. 8, 2018, 12 pages.

U.S. Appl. No. 15/712,849, Office Action dated Apr. 12, 2018, 9 pages.

U.S. Appl. No. 15/712,849, Notice of Allowance dated Dec. 4, 2018, 8 pages.

Van Engelund, et al., In Ovarian Cancer Methods and Protocols, Humana Press, John M.S. Bartlett, Ed. (2000), pp. 669-677, 12 pages.

\* cited by examiner

Primary Validation siRNAs

| Gene Symbol | Gene ID | siRNA Target Sequence 1 | SEQ ID No. | siRNA Target Sequence 2 | SEQ ID No. | siRNA Target Sequence 3 | SEQ ID No. |
|---|---|---|---|---|---|---|---|
| ABL1 | 25 | CCAGTGGAGATAACACTCTAA | 1 | AAAGGTGAAAAGCTCCGGGTC | 29 | AACTTGGTGAAGGTAGCTGAT | 57 |
| CAMK2B | 816 | CCCGGAAGCAGGAGATCATTA | 2 | CACGACCATCCTGAACCCACA | 30 | CCGGCTCACGCAGTACATTGA | 58 |
| EIF2AK3 | 9451 | CGCGCGGCAGGTCATTAGTAA | 3 | CACAAACTGTATAACGGTTTA | 31 | CGGCAGGTCATTAGTAATTAT | 59 |
| EIF2AK4 | 440275 | CAAGGTTAAGTCTTTCGAGAA | 4 | CACCGTCAAGATTACGGACTA | 32 | TACACCTATGACAGCGACATA | 60 |
| EPHA2 | 1969 | AAGGAAGTGGTACTGCTGGAC | 5 | AAGCGCCTGTTCACCAAGATT | 33 | CAGCGCCAAGTAAACAGGGTA | 61 |
| FGFR3 | 2261 | CTGAAATTACGGGTACCTGAA | 6 | ACCCTACGTTACCGTGCTCAA | 34 | CCGATGTTATTAGATGTTACA | 62 |
| FGR | 2268 | CAGACCTTGTCTAGTTATTTA | 7 | TTGATTCTGTAAATAAGTAAA | 35 | CACGTGGAACGGCAGCACTAA | 63 |
| FYN | 2534 | AAGACATGTGGTTGTATATAA | 8 | GTGGCCCTTTATGACTATGAA | 36 | AAGAAGCAGGATGCTGATCTA | 64 |
| GALK2 | 2585 | TGCGCGAGTGCTCCAGTTTAA | 9 | CTGGAGGAACTCCGAACCCAA | 37 | ATCAATGGTACCTGCGACAA | 65 |
| IKBKE | 9641 | CAGAAGCATCCAGCAGATTCA | 10 | CCGCATCATCGAACGGCTAAA | 38 | CAAGATGAACTTCATCTACAA | 66 |
| ILK | 3611 | AAGGAAGAGGCAGGGACTTCAA | 11 | TAGCCGTAGTGTAATGATTGA | 39 | CAGCCCGAGTCCCGAGGATAA | 67 |
| MAP3K2 | 10746 | TGCCATGTTTGCTCTAAATTA | 12 | AATGATGTCCGAGTCAAATTT | 40 | CAAGATAATAGAGTAGCCTAA | 68 |
| MAP3K6 | 1326 | TAGGGATGCTCTAACGAATTA | 13 | CCGGCCAGTCTCTTTCTGTTTA | 41 | CGGGATGAGCCTCATCCGGAA | 69 |
| MAPK13 | 5603 | TTCGCTATTATGAAAGGCAAA | 14 | CCGGAGTGGCATGAAGCTGTA | 42 | CCCGACGAGATCAGCCAGATT | 70 |
| MPP3 | 4356 | TAGGAGGTATATGCAGTATTT | 15 | CACGTTGGAGATGAGCTCCGA | 43 | CTGGGTCTGTGAGCAGTTCAA | 71 |
| NEK4 | 6787 | CAGCAAGATCGTGATCGTCAT | 16 | CTCATCTAGGGTATATACAAA | 44 | GACCATAAGATCCTAGTGAAA | 72 |
| NUAK2 | 81788 | TCGGCTGATAGTTGGCATGATT | 17 | TACCTAATGGTCTCTACCTAA | 45 | TGGCGACATGTTCAACTACTA | 73 |
| PI4KB | 5298 | TACAATGACGTTAAGTCTTAA | 18 | CGACATGTTCAACTACTATAA | 46 | CACGGAAACACCCGTACCTTA | 74 |
| PRKCE | 5581 | GAGGATGAAGGCTCAGCTCAA | 19 | CCCGACCATGGTAGTGTTCAA | 47 | CTGGAGTGCCTGACATGACA | 75 |
| RPS6KL1 | 83694 | CGGCTCCCTATTTATACAATA | 20 | CCGGATGTTAGTGAGGACTAT | 48 | TTGGGTGAGTTCACGAATTA | 76 |
| STK32B | 55351 | ATGCCAGAAGTGGACTATGTA | 21 | CTTGGGAGGCGGTGTTCAAGAA | 49 | CCGGCCCGACTCGCAAAGAA | 77 |
| TK2 | 7084 | CACGTGGACTCTAGTATGTAA | 22 | CGGGATCGAATATTAACTCCA | 50 | TAGAGACAAGCGGGAAGGATA | 78 |
| TRIB2 | 28951 | CAGCAATACCTTGGATGATTA | 23 | CAGGTTGTCCCACATGTATAA | 51 | CAGAAATAGGTTACCGAATT | 79 |
| TTK | 7272 | CCCGGTGACATTCTATTTCCA | 24 | TCCGACTTTATGATTATGAAA | 52 | TAGGTGAATGGCGGTCACATA | 80 |
| TXK | 7294 | TCGGACGAAGTTCATCTTCTA | 25 | TACAATGAACACGGCACGCAA | 53 | TACAAGCAAGCGTACCATCTA | 81 |
| UCKL1 | 54963 | CACTAGTCTCTCAGCATTCAGTAT | 26 | CAAGACCTGCTAAGAGAATTA | 54 | ACAATTACGAATAGAATTCAA | 82 |
| WEE1 | 7465 | CACTAGTGTCTCAGACCAGAA | 27 | CAGCTTGTTGGGCGTTTCCAA | 55 | CAGGAGGAGCCAGCACCATTA | 83 |
| WNK4 | 65266 | CACTAGTGTCTCAGACCAGAA | 28 | CAGCTTGTTGGGCGTTTCCAA | 56 | CAGGAGGAGCCAGCACCATTA | 84 |

Secondary Validation siRNAs

| Gene Symbol | Gene ID | siRNA Target Sequence 1 | SEQ ID No. | siRNA Target Sequence 2 | SEQ ID No. | siRNA Target Sequence 3 | SEQ ID No. |
|---|---|---|---|---|---|---|---|
| ALK | 238 | CTCGACCATCATGACCGACTA | 85 | CTCCTCGGTTCTAGGGCTAAA | 105 | CACCTACGTATTTAAGATGAA | 125 |
| AMHR2 | 269 | CAGAATGTGCTCATTCGGGAA | 86 | ATGGCCAATATAAACCAGGTA | 106 | CACGACCACATTGTCCGATTT | 126 |
| AURKA | 6790 | CACCTTCGGCATCCTAATATT | 87 | TCCCAGCGCATTCCTTTGCAA | 107 | CAGGGCTGCCATATAACCTGA | 127 |
| CAMK2B | 816 | CCCGGAAGCAGGAGATCATTA | 88 | CACGACCATCCTGAACCCACA | 108 | — | — |
| CHEK1 | 1111 | TTGGAATAACTCACAGGGATA | 89 | AACTGAAGAAGCAGTCGCAGT | 109 | CCCGCACAGGTCTTTCCTTAT | 128 |
| EPHA3 | 2042 | TCGGATATGATTGTTTCTCAA | 90 | TTGGATAGTTTCCTACGTAAA | 110 | CCGCTGGATATGGGACGAACA | 129 |
| ERBB3 | 2065 | ACCACGTATCTGGTCATAAAA | 91 | CTTCGTCATGTTGAACTATAA | 111 | CCCAGTGAGAAGGCTAACAAA | 130 |
| FGFR3 | 2261 | CTGAAATTACGGGTACCTGAA | 92 | ACCCTACGTTACCGTGCTCAA | 112 | CCGATGTTATTAGATGTTACA | 131 |
| FLT1 | 2321 | TCGCCGAAGTTGTATGGTTA | 93 | CTGCCGGGTTACGTCACCTAA | 113 | TAGACCTTTCGTAGAGATGTA | 132 |
| FYN | 2534 | AAGACATGTGGTTGTATAAA | 94 | GTGGCCCTTTATGCCATATGAA | 114 | AAGAAGCAGGATGCTGATCTA | 133 |
| GK2 | 2712 | GACGAACTGAATATTGATATA | 95 | CTCGGGTGTGCCATAATAATA | 115 | TACGTTAGAAGAGACACTGTAA | 134 |
| ILK | 3611 | AAGGAAGAGCAGGGACTTCAA | 96 | TAGCCGTAGTGTAATGATTGA | 116 | CAGCCCGAGTCCGAGGATAA | 135 |
| NEK4 | 6787 | CTCATCTAGGGTATATACAAA | 97 | CTGGGTCTGTGAGCAGTTCAA | 117 | — | — |
| P4KB (PIK4CB) | 5298 | TCGGCTGATAGTGGCATGATT | 98 | CGACATGTTCAACTACTATAA | 118 | TGGCGACATGTTCAACTACTA | 136 |
| PIK3CB | 5291 | CCCTTCGATAAGATTATTGAA | 99 | TCGGGAAGCTACCATTTCTTA | 119 | CGGAAAGACTACAGATCTTAA | 137 |
| PIP5K1B | 8395 | TACACTCTATTCAAACAGCAA | 100 | AAGGGTTACCTTCCAGTTCAA | 120 | AAGGCTCAACGTATAAGCGAA | 138 |
| TRIB2 | 28951 | CACGTGGACTCTAGTATGTAA | 101 | CAGGTTGTCCCACATGTATAA | 121 | TAGAGACAAGCGGGAAGGATA | 139 |
| TTK | 7272 | CAGCAATACCTTGGATGATTA | 102 | TCCGACTTTATGATTATGAAA | 122 | CAGAAATAGGTTACCGGAATT | 140 |
| TXK | 7294 | CCCGGTGACATTCTATTTCCA | 103 | CAGCTGGGTTTAGCTACGAAA | 123 | TAGGTGAATGGCCGGTCACATA | 141 |
| WEE1 | 7465 | CACTGGTAAAGCATTCAGTAT | 104 | CAAGACCTGCTAAGAGAATTA | 124 | — | — |

METHODS FOR IDENTIFYING THERAPEUTIC TARGETS AND TREATING MONITORING CANCERS

CROSS REFERENCE TO RELATED APPLICATIONS

This application is a U.S. National Phase Application of International Patent Application No. PCT/US2014/066884, filed Nov. 21, 2014, now expired; which claims the benefit under 35 U.S.C. § 119(e) of U.S. Provisional Application No. 61/907,943, filed on Nov. 22, 2013, now expired, each of which is incorporated by reference herein in its entirety.

STATEMENT REGARDING GOVERNMENT INTEREST

This invention was made with government support under CA176303 awarded by the National Institutes of Health. The government has certain rights in the invention.

STATEMENT REGARDING SEQUENCE LISTING

The Sequence Listing associated with this application is provided in text format in lieu of a paper copy, and is hereby incorporated by reference into the specification. The name of the text file containing the Sequence Listing is FHCR_028_01WO_ST25.txt. The text file is 21 KB, was created on Nov. 21, 2014, and is being submitted electronically via EFS-Web.

FIELD OF THE INVENTION

This invention relates to methods of treating cancers associated with mutation of the p53 gene, including but not limited to head and neck squamous cell carcinomas (HNSCC), as well as methods of monitoring the progression of cancers and the response of cancers to treatment. In addition, the invention related to methods of identifying therapeutic targets and therapeutic agents for the treatment of cancers and other diseases.

BACKGROUND OF THE INVENTION

Patients with head and neck squamous cell carcinoma (HNSCC) are treated aggressively with surgery followed by radiation, often together with cisplatin (1). Although these treatments increase loco-regional control, they are frequently disfiguring and induce high-grade toxicities limiting their effectiveness (2). Furthermore, resistance to cisplatin and radiation contributes to tumor recurrence, and options for those who do not respond are limited to palliative care. Targeted therapies for HNSCC are scarce, limited to experimental agents targeting the epidermal growth factor receptor (3).

Mutations in the tumor suppressor gene p53 are very common in HNSCC, with an estimated frequency of >50% (4, 5). Disruptive p53 mutations have been associated with metastasis, resistance to radiation, and poor patient survival (6-8). Despite the strong implication of p53 in the biology and clinical outcome of HNSCC, there are no available therapies that specifically target p53 mutant cancer cells.

The present invention addresses this shortcoming by providing new therapies for the treatment of p53 mutant cancer cells, including HNSCC, as well as new methods for identifying therapeutic targets in cancers and other diseases.

BRIEF SUMMARY OF THE INVENTION

The present invention provides, inter alia, methods of treating and preventing diseases, including cancers, as well as related methods of monitoring the progression of a disease, and methods of identifying therapeutic targets and therapeutic agents for use in treating or preventing disease.

In one embodiment, the present invention includes a method for treating or preventing a cancer in a subject in need thereof, wherein the cancer comprises a mutation in a tumor suppressor gene, the method comprising providing to the subject an inhibitor of a G2/M, SFK, PI3K or FAK pathway. In particular embodiments, the tumor suppressor gene is a DNA-PKcs, Atm, $p19^{Arf}$, p53, Hras, Kras or Prkdc gene, or wherein the cancer comprises a mutation in both a p53 tumor suppressor gene and one or more of a Hras or Kras gene. In one embodiment, the tumor suppressor gene is a p53 gene. In various embodiments, the inhibitor inhibits the expression of a gene in the G2/M, SFK, PI3K or FAK pathway. In certain embodiments, the gene encodes a kinase. In certain embodiments, the kinase is listed in FIG. 1C, FIG. 7, or FIG. 8.

In particular embodiments, the inhibitor inhibits an activity of a protein in the G2/M, SFK, PI3K or FAK pathway. In certain embodiments, the protein is a kinase. In particular embodiments, the kinase functions in the G2/M transition. In certain embodiments, the kinase is listed in FIG. 1C, FIG. 7, or FIG. 8. In certain embodiments, the inhibitor is a G2/M checkpoint inhibitor. In one embodiment, the G2/M checkpoint inhibitor is MK-1775. In certain embodiments, the kinase inhibitor is MK-1775, TAE684, PI828, PIK93, PP2, PF-562271, or AZD7762. In particular embodiments, any of these methods further comprise providing to the subject cisplatin. In certain embodiments, the kinase is NEK4, WEE1, ILK, CAM2 KB, FGFR3, FYN, PI4KB, TRIB2, TTK or TXK. In certain embodiments, the kinase is WEE1, ALK, PI3K, PIK4CB, FYN, or FAK. In certain embodiments, the kinase is WEE1, NEK4 or AURKA. In certain embodiments, the kinase is WEE1, CHEK1, GK2, PIP5K1B, EPHA2, RPS6KL1, MPP3, EPHA3, or AURKA. In one embodiment, the kinase is WEE1 and the inhibitor is MK-1775 or 681640. In one embodiment, the kinase is ALK and the inhibitor is TAE684. In one embodiment, the kinase is PI3K and the inhibitor is PI828. In one embodiment, the kinase is PIK4CB and the inhibitor is PIK93. In one embodiment, the kinase is FYN and the inhibitor is PP2. In one embodiment, the kinase is FAK and the kinase inhibitor is PF-562271. In particular embodiments, the inhibitor comprises a small molecule, a polynucleotide, or a polypeptide. In certain embodiments, the polynucleotide is an antisense RNA, an siRNA, or an miRNA. In certain embodiments, the polypeptide is an antibody or functional fragment thereof.

In a related embodiment, the present invention includes a method for treating or preventing a cancer in a subject in need thereof, wherein the cancer comprises a mutation in a tumor suppressor gene, the method comprising providing to the subject an inhibitor of a kinase selected from NEK4, TRIB2, TXK, CAMK2B, NUAK2, EPHA3, ALK, PIP5K1B, RPS6KL1, FGFR3, WEE1, and PRKCE.

In particular embodiments, the methods further comprise determining a level of expression or activity of a kinase gene or its encoded gene product in cancer cells obtained from the subject. In some embodiments, determining the level of expression comprises determining an amount of mRNA expressed by the kinase gene. In other embodiments, determining the level of expression comprises determining an amount of polypeptide encoded by the kinase gene. In particular embodiments, the kinase gene is listed in FIG. 1C, FIG. 7 or FIG. 8. In particular embodiments, the level of expression or activity of the kinase gene or its encoded gene product is determined prior to providing the subject with the inhibitor. In other embodiments, the level of expression or activity of the kinase gene or its encoded gene product is determined at about the same time as providing the subject with the inhibitor. In other embodiments, the level of expression or activity of the kinase gene or its encoded gene product is determined after providing the subject with the inhibitor.

In another embodiment, the present invention includes a method of monitoring the progression or regression of a tumor in response to a treatment, comprising: (a) determining a level of expression or activity of a kinase gene or its encoded gene product in cancer cells obtained from the subject prior to or at about the same time as providing the subject with the inhibitor; and (b) determining a level of expression or activity of a kinase gene or its encoded gene product in cancer cells obtained from the subject following a time period after providing the subject with the inhibitor; wherein a reduced level of expression or activity determined for (b) as compared to the level of expression of activity determined for (a) indicates that the treatment is effective. In particular embodiments, the kinase gene is listed in FIG. 1C, FIG. 7 or FIG. 8.

In a further related embodiment, the present invention includes a method of identifying a therapeutic drug target in a diseased cell, comprising: (a) screening a plurality of siRNAs for their ability to inhibit growth or reduce viability of a human diseased cell or a human cell having a defined mutation; (b) identifying one or more genes targeted by one or more siRNAs of (a) that inhibit growth or reduce viability of the human cell; (c) screening a plurality of siRNAs for their ability to inhibit growth or reduce viability of a non-human diseased cell or a non-human cell having a defined mutation; (d) identifying one or more genes targeted by one or more siRNAs of (c) that inhibit growth or reduce viability of the non-human cell; and (e) determining one or more genes identified according to both (b) and (d), wherein the human diseased cell and the non-human disease cell share the same disease or the mutation in the human cell is in the same gene as the mutation in the non-human cell, and wherein the one or more genes determined according to (e) or their encoded products are identified as therapeutic drug targets. In certain embodiments, the pluralities of siRNAs target kinases. In certain embodiments, the non-human cell is a mammalian cell. In particular embodiments, the diseased cell is a tumor cell, e.g., a primary tumor cell or a metastic or relapsed tumor cell. In particular embodiments, the cell comprises a mutation in a tumor suppressor gene, e.g., a DNA-PKcs, Atm, p19$^{Arf}$, p53, or Prkdc gene.

In a further embodiment, the present invention includes a method for treating or preventing a cancer in a subject in need thereof, comprising: (a) screening a plurality of siRNAs for their ability to inhibit growth or reduce viability of a cancer cell obtained from the subject; (b) identifying one or more genes targeted by one or more siRNAs of (a) that inhibit growth or reduce viability of the cancer cell; and (c) providing to the subject an inhibitor of one or more of the genes identified in (b). In certain embodiments, the method further comprises obtaining a biological sample comprising a cancer cell from the subject. the plurality of siRNAs target kinases.

In yet another related embodiment, the present invention includes a method for treating or preventing a cancer in a subject in need thereof, comprising: (a) obtaining or requesting the results of a test comprising: (i) screening a plurality of siRNAs for their ability to inhibit growth or reduce viability of a cancer cell obtained from the subject; and (ii) identifying one or more genes targeted by one or more siRNAs of (a) that inhibit growth or reduce viability of the cancer cell; and (b) providing to the subject an inhibitor of one or more of the genes identified according to (a). In particular embodiments, the plurality of siRNAs target kinases.

In particular embodiments of any of the methods described herein, the cancer is a squamous cell carcinoma, e.g., a head and neck squamous cell carcinoma. In particular embodiments, the cancer is a p53 mutant squamous cell carcinoma. In certain embodiments, the tumor is a primary tumor, while in other embodiments, the tumor is a recurrent or metastatic tumor. In particular embodiments, the cancer is a head or neck cancer, a breast cancer, a prostate cancer, a brain cancer, a thyroid cancer, a lung cancer, an ovarian cancer, a stomach cancer, a pancreatic cancer, a liver cancer, a skin cancer, a leukemia, a lymphoma, a colon cancer, a cervical cancer, a uterine cancer, an esophageal cancer, or a bladder cancer.

In particular embodiments, of any of the methods described herein, the inhibitor inhibits one of the following kinases: NEK4, WEE1, ILK, CAM2 KB, FGFR3, FYN, PI4 KB, TRIB2, TTK or TXK. In certain embodiments, the kinase is WEE1, ALK, PI3K, PIK4CB, FYN, or FAK. In certain embodiments, the kinase is WEE1, NEK4 or AURKA. In certain embodiments, the kinase is WEE1, CHEK1, GK2, PIP5K1B, EPHA2, RPS6KL1, MPP3, EPHA3, or AURKA.

In various embodiments of any of the methods of treatment described herein, the inhibitor is provided to the subject in combination with another therapeutic agent.

This summary is provided to introduce a selection of concepts in a simplified form that are further described below in the Detailed Description. This summary is not intended to identify key features of the claimed subject matter nor is it intended to be used as an aid in determining the scope of the claimed subject matter.

BRIEF DESCRIPTION OF THE DRAWINGS

FIG. 7. Primary validation siRNAs used for various target genes.

FIG. 8. Secondary validation siRNAs used for various target genes.

DETAILED DESCRIPTION OF THE INVENTION

Figure 1A:
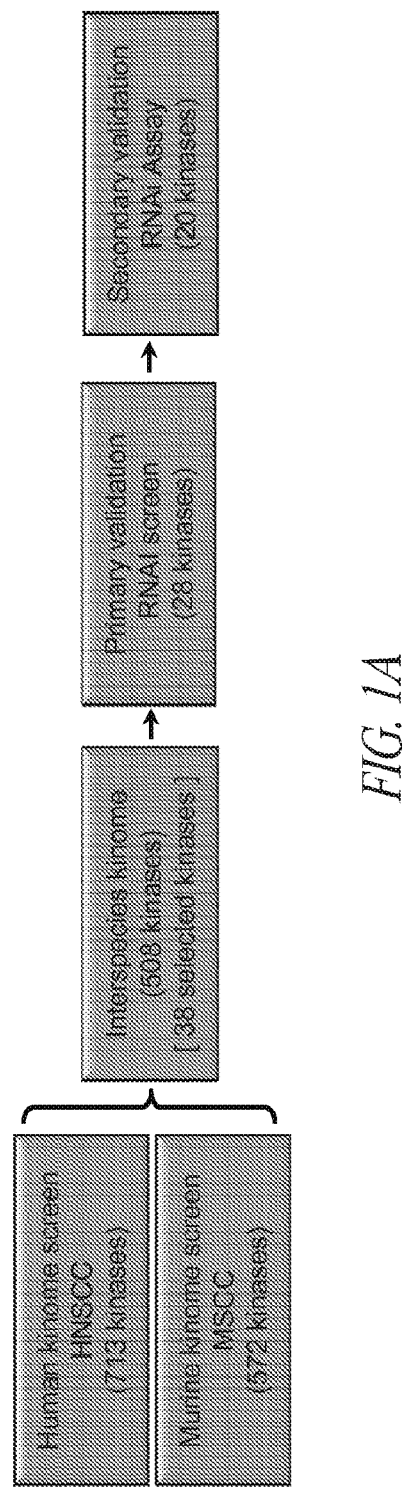
FIG. 1 provides diagrams showing the comparative functional kinomics approach to identify survival kinases in squamous cell carcinoma. A. Flow chart schematic of functional kinomic approach for discovery of kinase targets. RNAi screen hits from both murine (MSCC) and human (HNSCC) cells were prioritized by cross-species comparison. B. Cartesian plots of Zscores from interspecies kinome (508 kinases) to identify kinase targets which had the highest shared impact on cell viability. Human and mouse cell lines were sorted into each of three comparisons: all cells (left), p53 mutant cells (middle), and metastatic cells (right). Candidate kinase targets with Zscores greater than one standard deviation from the mean cell viability per comparison are shown in gray. C. Venn diagram of selection of 38 kinase targets from interspecies comparison; inclusion in diagram represents kinases targets that met a certain threshold in each comparison.

The present invention is based, in part, on the development of a novel approach to identify therapeutic target genes and biological pathways associated with diseases, such as cancers, and the use of this approach to identify new therapeutic target genes and pathways in cancers associated with p53 mutations, such as HNSCC.

As described in the accompanying Examples, a functional kinomics approach and human-murine interspecies comparison of high-throughput siRNA viability screens were employed to identify conserved survival pathways in squamous cell carcinoma, in order to address the unmet need to find novel therapies for p53 mutant head and neck squamous cell. The rationale for targeting kinases in cancer was significant, and as such, efforts were focused on the kinome to identify druggable and clinically relevant survival kinases in HNSCC. These studies revealed vulnerabilities of p53 mutant HNSCC cells to inhibition of G2/M, SFK, PI3K and FAK pathways. Preclinical validation studies performed on the kinase target, WEE1, demonstrated proof of concept and mechanism. Preclinical data demonstrated the vulnerability of p53 mutant HNSCC cells to deregulation of G2/M transition, and support initiation of clinical trials with MK-1775 or other G2/M checkpoint inhibitors for the treatment of HNSCC, alone or in combination with cisplatin.

Definitions and Abbreviations

The words "a" and "an" denote one or more, unless specifically noted.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length. In any embodiment discussed in the context of a numerical value used in conjunction with the term "about," it is specifically contemplated that the term about can be omitted.

Unless the context requires otherwise, throughout the present specification and claims, the word "comprise" and variations thereof, such as, "comprises" and "comprising" are to be construed in an open, inclusive sense, that is as "including, but not limited to".

By "consisting of" is meant including, and limited to, whatever follows the phrase "consisting of." Thus, the phrase "consisting of" indicates that the listed elements are required or mandatory, and that no other elements may be present.

By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

An "increased" or "enhanced" amount is typically a "statistically significant" amount, and may include an increase that is 1.1, 1.2, 1.3, 1.4, 1.5, 1.6, 1.7, 1.8, 1.9, 2, 2.5, 3, 3.5, 4, 4.5, 5, 6, 7, 8, 9, 10, 15, 20, 30, 40, or 50 or more times (e.g., 100, 500, 1000 times) (including all integers and decimal points in between and above 1, e.g., 2.1, 2.2, 2.3, 2.4, etc.) an amount or level described herein.

A "decreased" or "reduced" or "lesser" amount is typically a "statistically significant" amount, and may include a decrease that is about 1.1, 1.2, 1.3, 1.4, 1.5, 1.6 1.7, 1.8, 1.9, 2, 2.5, 3, 3.5, 4, 4.5, 5, 6, 7, 8, 9, 10, 15, 20, 30, 40, or 50 or more times (e.g., 100, 500, 1000 times) (including all integers and decimal points in between and above 1, e.g., 1.5, 1.6, 1.7. 1.8, etc.) an amount or level described herein.

A "composition" can comprise an active agent, e.g., a kinase inhibitor, and a carrier, inert or active, e.g., a pharmaceutically acceptable carrier, diluent or excipient. In particular embodiments, a composition is sterile, substantially free of endotoxins or non-toxic to recipients at the dosage or concentration employed.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent or emulsifier which has been approved by the United States Food and Drug Administration as being acceptable for use in humans or domestic animals.

The terms "mammal" and "subject" includes human and non-human mammals, such as, e.g., a mouse, rat, rabbit, monkey, cow, hog, sheep, horse, dog, and cat.

"Pharmaceutically acceptable salts" include sulfate, citrate, acetate, oxalate, chloride, bromide, iodide, nitrate, bisulfate, phosphate, acid phosphate, lsomcotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, pamoate, phenylacetate, trifluoroacetate, acrylate, chlorobenzoate, dimtrobenzoate, hydroxybenzoate, methoxybenzoate, methylbenzoate, o-acetoxybenzoate, naphthalene-2-benzoate, isobutyrate, phenylbutyrate, alpha-hydroxybutyrate, butyne-1,4-dicarboxylate, hexyne-1,4-dicarboxylate, caprate, caprylate, cinnamate, glycollate, heptanoate, hippurate, malate, hydroxymaleate, malonate, mandelate, mesylate, mcotinate, phthalate, teraphthalate, propiolate, propionate, phenylpropionate, sebacate, suberate, p-bromobenzenesulfonate, chlorobenzenesulfonate, ethylsulfonate, 2-hydroxyethylsulfonate, methylsulfonate, naphthalene-1-sulfonate, naphthalene-2-sulfonate, naphthalene-1,5-sulfonate, xylenesulfonate, and tartarate salts. The term "pharmaceutically acceptable salt" also refers to a salt of an antagonist of the present invention having an acidic functional group, such as a carboxylic acid functional group, and a base. Suitable bases include, but are not limited to, hydroxides of alkali metals such as sodium, potassium, and lithium, hydroxides of alkaline earth metal such as calcium and magnesium, hydroxides of other metals, such as aluminum and zinc, ammonia, and organic amines, such as unsubstituted or hydroxy-substituted mono-, di-, or tri-alkylamines, dicyclohexylamine, tributylamine, pyridine, N-methyl, N-ethylamine, diethylamine, triethylamine, mono-, bis-, or tris-(2-OH-lower alkylamines), such as mono-, bis-, or tris-(2-hydroxyethyl)amine, 2-hydroxy-tert-butylamine, or tris-(hydroxymethyl)methylamine, N,N-di-lower alkyl-N-(hydroxyl-lower alkyl)-amines, such as N,N-dimethyl-N-(2-hydroxyethyl)amine or tri-(2-hydroxyethyl)amine, N-methyl-D-glucamine, and amino acids such as arginine, lysine, and the like. The term "pharmaceutically acceptable salt" also includes a hydrate of a compound of the invention.

"Optional" or "optionally" means that the subsequently described event of circumstances may or may not occur, and that the description includes instances where said event or circumstance occurs and instances in which it does not.

"Pharmaceutical composition" refers to a composition or formulation of an active agent, e.g., a kinase inhibitor, and a medium generally accepted in the art for the delivery of the biologically active agents to mammals, e.g., humans. Such a medium may include any pharmaceutically acceptable carriers, diluents or excipients therefore.

"Small molecule" refers to natural or synthetic small organic or inorganic compounds having a molecular weight of more than 50 and less than about 2,500 Daltons.

"Therapeutically effective amount" refers to that amount of an active agent, e.g., a kinase inhibitor, that, when administered to a mammal, preferably a human, is sufficient to effect treatment, as defined below, of a disease or condition in the mammal, preferably a human. The amount of an active agent that constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

"Treating" or "treatment" as used herein covers the treatment of the disease or condition of interest, e.g., tissue injury, in a subject or mammal, e.g., a human, having the disease or condition of interest, and includes: (i) preventing or inhibiting the disease or condition from occurring in the subject or mammal, in particular, when such subject or mammal is predisposed to the condition but has not yet been diagnosed as having it; (ii) inhibiting the disease or condition, i.e., arresting its development; (iii) relieving the disease or condition, i.e., causing regression of the disease or condition; or (iv) relieving the symptoms resulting from the disease or condition. As used herein, the terms "disease," "disorder," and "condition" may be used interchangeably or may be different in that the particular malady, injury or condition may not have a known causative agent (so that etiology has not yet been worked out), and it is, therefore, not yet recognized as an injury or disease but only as an undesirable condition or syndrome, wherein a more or less specific set of symptoms have been identified by clinicians.

Methods of Treating, Preventing and Monitoring Disease

As demonstrated in the accompanying Examples, certain methods of the present invention are used to identify therapeutic targets for a disease. Accordingly, the present invention also provides methods of treating a disease based on the identification of a therapeutic target. In particular embodiments, the therapeutic target is overexpressed in disease cells. In certain embodiments, inhibition of the therapeutic target results in reduced growth, proliferation or viability of the disease cell. In particular embodiments, inhibition of the therapeutic target results in death of the disease cell. In particular embodiments, inhibition of the therapeutic target induces apoptosis of the disease cell.

In one aspect, the present invention provides methods for inhibiting the growth and/or proliferation of diseased cells, e.g., cancer cells, comprising contacting the cells with an inhibitor of a kinase or kinase pathway. In related embodiments, the present invention provides methods for reducing viability or inducing apoptosis of diseased cells, e.g., cancer cells, comprising contacting the cells with an inhibitor of a kinase or kinase pathway. In one embodiment, the diseased cell is contacted in vitro. In another embodiment, the diseased cell is contacted in vivo, e.g., in a mammalian subject. In particular embodiments, the kinase is any of those described herein, e.g., WEE1, ALK, PIK4CB, FAK, NEK4, AURKA, CHK1, or a SRC family member or related kinase, such as SFK, FYN, TXK or CAM2 KB. In particular embodiments, the kinase is NEK4, TRIB2, TXK, CAMK2B, NUAK2, EPHA3, ALK, PIP5K1B, RPS6KL1, FGFR3, WEE1 or PRKCE. In certain embodiments, the present invention provides methods for inducing apoptosis of cancer cells, comprising contacting the cells with an inhibitor of WEE1, NEK4 or AURKA. In particular embodiments, the disease cells are contacted with two or more inhibitors of a kinase or kinase pathway, e.g., an inhibitor of WEE1 and an inhibitor of CHK1.

In another aspect, the invention provides a method of treating or preventing a disease in a subject in need thereof, comprising providing to or administering to the subject an amount of a composition comprising an effective amount of an inhibitor of a kinase or kinase pathway. In particular embodiments, the composition is a pharmaceutical composition further comprising one or more pharmaceutically acceptable carriers, diluents or excipients. In particular embodiments, the subject has been diagnosed with or identified as being at risk of having a cancer, e.g., a squamous cell carcinoma. In particular embodiments, the subject has been diagnosed with a tumor having a mutation in p53, or another gene in the p53 pathway. In particular embodiments, the kinase is any of those described herein, e.g., WEE1, ALK, PIK4CB, FAK, NEK4, AURKA, CHK1, or a SRC family member or related kinase, such as SFK, FYN, TXK or CAM2 KB. In particular embodiments, the subject is provided with or administered two or more inhibitors of a kinase or kinase pathway, e.g., an inhibitor of WEE1 and an inhibitor of CHK1. In particular embodiments of these and other methods of the present invention, the diseased cells are cancer cells, or the subject is diagnosed with or considered at risk for cancer. In particular embodiments, the cancer cell is a primary tumor or a secondary or metastatic tumor. In certain instances, the tumor is a solid tumor; in other instances, the tumor is a liquid tumor. In certain embodiments, the cancer cells have a mutation in a tumor suppressor gene, e.g., a DNA-PKcs, Atm, $p19^{Arf}$, p53, Hras, Kras, or Prkdc gene. In certain embodiments, a subject is considered at risk of cancer if the subject has a mutation in a tumor suppressor gene, including any of those described herein, such as p53.

In certain embodiments, the cancer cells have a mutation in a p53 tumor suppressor gene. In certain embodiments, the cancer cells have a mutation in both a p53 tumor suppressor gene and one or more of a Hras or Kras gene. p53 mutations have been associated with a number of different types of cancer, including but not limited to lung cancer, stomach cancer, breast cancer, colon cancer, liver cancer, prostate cancer, cervical cancer, uterine cancer, head and neck cancer, esophageal cancer, leukemia, lymphoma, ovarian cancer, and bladder cancer. Any of these and other types of cancer may be treated or prevented according to the methods described herein. In certain embodiments, the cancer is a head or neck cancer, a breast cancer, a prostate cancer, a brain cancer, a thyroid cancer, a lung cancer, an ovarian cancer, a stomach cancer, a pancreatic cancer, a liver cancer, a skin cancer, a leukemia, a lymphoma, a colon cancer, a cervical cancer, a uterine cancer, an esophageal cancer, or a bladder cancer. In particular embodiments, the cancer is a squamous cell carcinoma, e.g., a head and neck squamous cell carcinoma. In certain embodiments, the cancer is a squamous cell carcinoma of the lung, cervix, skin or bladder.

In one embodiments, the present invention includes a method for treating or preventing a cancer in a subject in need thereof, the method comprising providing to the subject an effective amount of a composition comprising an inhibitor of a G2/M, SFK, PI3K or FAK pathway. In particular embodiments, the cancer comprises a mutation in a tumor suppressor gene, e.g., p53. In particular embodiments, the inhibitor inhibits expression of a gene in the G2/M, SFK, PI3K or FAK pathway. In certain embodiments, the inhibitor inhibits an activity of a protein the G2/M, SFK, PI3K or FAK pathway.

In other embodiments of any of the methods described herein, the cancer is human papilloma virus (HPV) positive. In certain embodiments, the HPV positive cancer is p53 wild-type, while in certain embodiments, the HPV positive cancer comprises a mutation in a tumor suppressor gene.

In particular embodiments, the disease cell, e.g., a tumor cell, comprises a mutation in p53, and the kinase is WEE1, CDKN1B, PRKCE, GK2, or FGFR3. Thus, in certain embodiments wherein the tumor cell comprises a mutation in p53, the subject is treated using an inhibitor of WEE1, CDKN1B, PRKCE, GK2, or FGFR3. In particular embodiments, the tumor is a squamous cell carcinoma, e.g., a head and neck squamous cell carcinoma. In particular embodiments, the subject is treated with the inhibitor in combination with cisplatin.

In particular embodiments, the disease cell, e.g., a tumor cell, comprises a mutation in p53, and the kinase is WEE1, CHEK1, GK2, PIP5K1B, EPHA2, RPS6KL1, MPP3, EPHA3 or AURKA. Thus, in certain embodiments wherein the tumor cell comprises a mutation in p53, the subject is treated using an inhibitor of WEE1, CHEK1, GK2, PIP5K1B, EPHA2, RPS6KL1, MPP3, EPHA3 or AURKA. In particular embodiments, the tumor is a squamous cell carcinoma, e.g., a head and neck squamous cell carcinoma. In particular embodiments, the subject is treated with the inhibitor in combination with cisplatin.

In certain embodiments, the disease cell, e.g., a tumor cell, comprises a mutation in $p19^{Arf}$, and the kinase is GK2, MAP2K7RIPK1, PLK1, or PRKCE. Thus, in certain embodiments wherein the tumor cell comprises a mutation in $p19^{Arf}$, the subject is treated using an inhibitor of GK2, MAP2K7RIPK1, PLK1, or PRKCE. In particular embodiments, the tumor is a squamous cell carcinoma, e.g., a head and neck squamous cell carcinoma. In particular embodiments, the subject is treated with the inhibitor in combination with cisplatin.

In certain embodiments, the disease cell, e.g., a tumor cell, comprises a mutation in Atm, and the kinase is AK1, STK22B, CLK1, PRKCE or GK2. Thus, in certain embodiments wherein the tumor cell comprises a mutation in Atm, the subject is treated with an inhibitor of AK1, STK22B, CLK1, PRKCE or GK2. In particular embodiments, the tumor is a squamous cell carcinoma, e.g., a head and neck squamous cell carcinoma. In particular embodiments, the subject is treated with the inhibitor in combination with cisplatin.

In certain embodiments, the disease cell, e.g., a tumor cell, comprises a mutation in both KRAS and p53, and the kinase is WEE1, CHEK1, CAMK2B, or GK2. Thus, in certain embodiments wherein the tumor cell comprises a mutation in KRAS and/or p53, the subject is treated using an inhibitor of WEE1, CHEK1, CAMK2B, or GK2. In particular embodiments, the tumor is a squamous cell carcinoma, or a pancreatic cancer. In particular embodiments, the subject is treated with the inhibitor in combination with cisplatin.

In certain embodiments, the disease cell, e.g., a tumor cell, comprises a mutation in KRAS, and the kinase is FGFR3, NUAK2, ABL1, NEK4, AURKA, WEE1 or CHEK1. Thus, in certain embodiments wherein the tumor cell comprises a mutation in KRAS, the subject is treated using an inhibitor of FGFR3, NUAK2, ABL1, NEK4, AURKA, WEE1 or CHEK1. In particular embodiments, the tumor is a squamous cell carcinoma, or a pancreatic cancer. In particular embodiments, the subject is treated with the inhibitor in combination with cisplatin.

In certain embodiments of the methods described herein, the gene that is inhibited encodes a kinase, or the protein that is inhibited is a kinase. In certain embodiments, the kinase is listed in FIG. 1, FIG. 2, FIG. 3, FIG. 7 or FIG. 8. In particular embodiments, the kinase is selected from serine/threonine kinase 32B (STK32B); aurora kinase A (AURKA); galactokinase 2 (GALK2); thymidine kinase 2 (TK2), mitochondrial NUAK family, SNF1-like kinase 2 (NUAK2); calcium/calmodulin dependent protein kinase II beta (CAMK2B); membrane protein, palmitoylated 3 (MAGUK) (MPP3); serine/arginine rich protein specific kinase 3 (STK23); phosphatidylinositol-4-phosphate 5-kinase, type 1, beta (PIP5K1B); glycerol kinase 2 (GK2); ribosomal protein S6 kinase-like 1 (RPS6KL1); phosphatidylinositol 4-kinase, catalytic, beta (PIK4CB); FYN oncogene related to SRC, FGR, YES (FYN); eukaryotic translation-initiation factor 2 alpha kinase 3 (EIF2AK3); inhibitor of kappa light polypeptide gene enhancer in B cells, kinase epsilon (IKBKE); Gardner-Rasheed feline sarcoma viral (v-fgr) oncogene homolog (FGR); mitogen-activated protein kinase kinase kinase 8 (MAP3K8); uridine-cytidine kinase 1-like 1 (UCKL1); tribbles homolog 2 (*Drosophila*) (TRIB2); eukaryotic translation-initiation factor 2 alpha kinase 4 (EIF2AK4); TXK tyrosine kinase (TXK); EPH receptor 3 (EPHA3); anti-Mullerian hormone receptor, type II (AMHR2); Wee1 homolog (*S. pombe*) (WEE1); Chk1 checkpoint homolog (*S. pombe*) (CHK1); mitogen-activated protein kinase 13 (MAPK13); TTK protein kinase (TTK); fms-related tyrosine kinase 1 (FLT1); phosphoinositide-3-kinase, catalytic, beta polypeptide (PIK3CB); Integrin-linked kinase (ILK); anaplastic lymphoma receptor tyrosine kinase (ALK); NIMA (never in mitosis gene a)-related expressed kinase 4 (NEK4); WNK lysine deficient protein kinase 4 (WNK4); c-abl oncogene 1, non-receptor tyrosine kinase (ABL1); v-erb-b2 erythroblastic leukemia viral oncogene homolog 3 (avian) (ERBB3); mitogen-activated protein kinase kinase kinase 2 (MAP3K2); fibroblast growth factor receptor 3 (FGFR3); or Protein kinase C, Epsilon (PKCE). In certain embodiments, two or more of these genes are inhibited according to a method of the invention.

In particular embodiments, the kinase is WEE1, CDKN1B, PRKCE, GK2, FGFR3, GK2, MAP2K7RIPK1, PLK1, PRKCE, AK1, STK22B, CLK1, PRKCE or GK2. In particular embodiments, the kinase is NEK4, WEE1, ILK, CAM2 KB, FGFR3, FYN, PI4 KB, TRIB2, TTK or TXK. In certain embodiments, the kinase is WEE1, ALK, PI3K, PIK4CB, FYN, or FAK. In certain embodiments, the kinase is WEE1, NEK4 or AURKA. In certain embodiments, the kinase is WEE1.

In certain embodiments, the kinase functions in the G2/M transition, e.g., WEE1, NEK4, TTK, AURKA and CHK1. In particular embodiments, the inhibitor is a G2/M checkpoint inhibitor. One example of a G2/M checkpoint inhibitor is MK-1775. In other embodiments, the kinase is implicated in focal adhesion and integrin signaling, e.g., CAMK2B, FYN, ILK, EPHA3, EIF2AK4, and TRIB2. In certain embodiments, the kinase is implicated in phosphoinositide 3-kinase (PI3K) signaling, e.g., PIK4B, PIK3CB, PIP5K1B, TRIB2, FGFR3 and ALK. In certain embodiments, the kinase is implicated in SRC signaling, e.g., FYN, TXK and CAM2 KB.

In particular embodiments of methods of the present invention, the inhibitor is MK-1775, TAE684, PI828, PIK93, PP2, PF-562271, or AZD7762. In certain embodiments, the inhibitor is MK-1775. The method of claim 22, wherein the kinase is WEE1 and the inhibitor is MK-1775 or 681640.

In certain embodiments, the kinase is ALK, and the inhibitor is TAE684.

In certain embodiments, the kinase is PI3K, and the inhibitor is PI828.

In certain embodiments, the kinase is PIK4CB, and the inhibitor is PIK93.

In certain embodiments, the kinase is FYN, and the inhibitor is PP2.

In certain embodiments, the kinase is FAK, and the kinase inhibitor is PF-562271.

In particular embodiments, the disease is a cancer comprising a p53 mutation, or comprising both a p53 mutation and a mutation in one or both of Hras or Kras, and the kinase is listed in FIG. 1, FIG. 2, FIG. 3, FIG. 7 or FIG. 8. In particular embodiments, the kinase is NEK4, WEE1, ILK, CAM2 KB, FGFR3, FYN, PI4 KB, TRIB2, TTK or TXK. In certain embodiments, the kinase is WEE1, ALK, PI3K, PIK4CB, FYN, or FAK. In certain embodiments, the kinase is WEE1, NEK4 or AURKA. In certain embodiments, the kinase is WEE1. In particular embodiments, the kinase is FGFR3, NUAK2, ABL1, NEK4, AURKA, WEE1 or CHEK1. In certain embodiments, the kinase is WEE1, and the inhibitor is MK-1775 or 681640. In particular embodiments, the subject is treated with the inhibitor in combination with cisplatin.

In particular embodiments, the cancer is a head and neck cancer or a squamous cell carcinoma, e.g., a head and neck squamous cell carcinoma, and the kinase is listed in FIG. 1, FIG. 2, FIG. 3, FIG. 7 or FIG. 8. In particular embodiments, the kinase is NEK4, WEE1, ILK, CAM2 KB, FGFR3, FYN, PI4 KB, TRIB2, TTK or TXK. In certain embodiments, the kinase is WEE1, ALK, PI3K, PIK4CB, FYN, or FAK. In certain embodiments, the kinase is WEE1, NEK4 or AURKA. In certain embodiments, the kinase is WEE1. In particular embodiments, the head and neck cancer comprises a p53 mutation. In certain embodiments, the kinase is WEE1 and the inhibitor is MK-1775 or 681640.

In one embodiment, the method comprises treating or preventing a head and neck squamous cell carcinoma in a mammal, e.g., a human, in need thereof, comprising providing or administering to the mammal an effective amount of a pharmaceutical composition comprising MK-1775. In certain embodiments, the carcinoma comprises a p53 mutation. In certain embodiments, the mammal is also provided with an effective amount of a pharmaceutical composition comprising paclitaxel.

In certain embodiments, methods of the present invention further comprise providing or administering to the subject another therapeutic agent, in addition to the inhibitor. The inhibitor and the other therapeutic agent may be provided concurrently or one may be provided before or after the other. In particular embodiments wherein the disease is a cancer, the other therapeutic agent is, e.g., a chemotherapeutic agent or a genotoxic agent. In certain embodiments, the chemotherapeutic agent or genotoxic agent is cisplatin.

In certain embodiments of the method for treating or preventing a cancer, e.g., a p53 mutant cancer, in a mammal, e.g., a human, in need thereof, the method comprises providing or administering to the mammal an effective amount of an inhibitor of WEE1 and an effective amount of a genotoxic agent, such as cisplatin. In particular embodiments, the cancer is a squamous cell carcinoma, e.g., an HNSCC or a pancreatic cancer. In one embodiment, the method comprises treating or preventing a head and neck squamous cell carcinoma in a mammal, e.g., a human, in need thereof, comprising providing or administering to the mammal an effective amount of a pharmaceutical composition comprising MK-1775 and an effective amount of the genotoxic agent, e.g., cisplatin. In certain embodiments, the carcinoma comprises a p53 mutation. In a particular embodiment, the method comprises administered to a subject having a p53-mutant cancer, e.g., a squamous cell carcinoma, such as a HNSCC, cisplatin in combination with an inhibitor of WEE1, such as MK-1775. In particular embodiments, such methods further comprising performing surgery and/or treating the subject with radiation therapy. In particular embodiments, the method further comprises determining that the subject has a mutation in a tumor suppressor gene.

In a related embodiment, the present invention includes a method of reducing the toxicity of cisplatin, comprising administering to a subject in need thereof cisplatin in combination with an inhibitor of a kinase as described herein, e.g., an inhibitor of WEE1, such as MK-1775. In particular embodiments, the cancer comprises a mutation in a tumor suppressor gene, e.g., p53. In particular embodiments, the method further comprises determining that the subject has a mutation in a tumor suppressor gene.

In a related embodiment, the present invention includes a method of increasing the efficacy of cisplatin, comprising administering to a subject in need thereof cisplatin in combination with an inhibitor of a kinase as described herein, e.g., an inhibitor of WEE1, such as MK-1775. In particular embodiments, the cancer comprises a mutation in a tumor suppressor gene, e.g., p53. In particular embodiments, the method further comprises determining that the subject has a mutation in a tumor suppressor gene.

In certain embodiments of any of the methods described herein comprising the administration of cisplatin, the amount of cisplatin administered is less than the amount recommended for treatment using cisplatin without the kinase inhibitor. In particular embodiments, the amount of cisplatin administered in a single treatment or administration is less than 100 $mg/m^2$, less than 50 $mg/m^2$, less than 20 $mg/m^2$, less than 10 $mg/m^2$, less than 5 mg/m2, less than 1 m $g/m^2$, less than 0.5 $mg/m^2$, less than 0.2 mg/m2, less than 0.1 $mg/m^2$, or less than 0.05 $mg/m^2$, or in any range that may be derived between these values. In certain embodiments of any of the methods described herein comprising the administration of cisplatin, the amount of cisplatin administered is a normal amount recommended for treatment using cisplatin without the kinase inhibitor, while in other embodiments, it is a reduced amount, including any of those amounts described above.

In certain embodiments of any of the methods described herein, the subject may also be treated via surgery and/or radiation therapy.

In some embodiments, the methods further comprise the step of determining whether the tumor in the subject comprises a mutation in a tumor suppressor gene, e.g., a p53 mutation, before providing to the subject an inhibitor. The step of determining whether the tumor in the subject comprises a mutation in a tumor suppressor gene, e.g., a p53 gene, may be carried out by accessing a database, requesting the results of appropriate diagnostic or genetic testing, or by assaying cells obtaining from the subject (such as a biopsy sample from said subject) for the presence or absence of a p53 mutation, using standard methods known in the art and as further described herein. A variety of specific p53 mutations associated with cancers are known in the art and may be detected using routine methods. For example, a subject's p53 gene may be sequenced, or probes specific for known mutations may be used to selectively amplify sequences comprising the mutations. In particular embodiments, a subject is treated with the inhibitor if the subject's tumor has the mutation in the tumor suppressor gene, and in other embodiments, the subject is not treated with the inhibitor if the subject does not have the mutation in the tumor suppressor gene, e.g., p53. In certain embodiments of any of the methods herein that comprise determining whether a subject has a mutation in a tumor suppressor gene, such as p53, the subject is administered the inhibitor if the subject has said mutation but not if the subject does not have said mutation. Accordingly, in certain embodiments, the present invention provides methods for distinguishing between whether to treat a particular tumor in a particular subject with an inhibitor of a kinase, as described herein, based upon whether or not the tumor has a mutation in a tumor suppressor gene, such as p53.

In some embodiments, any of the methods further comprise determining a level of expression or activity of a tumor suppressor gene or a kinase gene (or their encoded gene product) in disease cells, e.g., cancer cells, obtained from the subject. In certain embodiments, determining the level of expression comprises determining an amount of mRNA expressed by the tumor suppressor or kinase gene. In certain embodiments, determining the level of expression comprises determining an amount of polypeptide encoded by the tumor suppressor or kinase gene. In particular embodiments, the kinase gene is listed in FIG. 1C, FIG. 7 or FIG. 8. In particular embodiments, the level of expression or activity of the tumor suppressor or kinase gene (or its encoded gene product) is determined prior to providing the subject with the inhibitor. In certain embodiments, the level of expression or activity of the tumor suppressor or kinase gene (or its encoded gene product) is determined at about the same time as providing the subject with the inhibitor. In certain embodiments, the level of expression or activity of the tumor suppressor or kinase gene (or its encoded gene product) is determined after providing the subject with the inhibitor. In particular embodiments, a subject is treated with the inhibitor if the subject's tumor has a reduced level of expression of the tumor suppressor gene or its encoded protein as compared to the level in a normal control cell, and in other embodiments, the subject is not treated with the inhibitor if the subject has a normal or higher level of expression the tumor suppressor gene, e.g., p53, as compare to the level in a normal control cell, e.g., a cell with wild-type p53.

The present invention further provides methods of determining an appropriate treatment or monitoring the therapeutic effect of an inhibitor or treatment, which may be practiced alone or in combination with any of the methods described herein.

In one embodiment, the present invention includes a method of identifying a subject suitable for treatment with an inhibitor according to a method described herein, comprising: (a) determining a level of expression or activity of a kinase gene or its encoded gene product in disease cells, e.g., cancer cells, obtained from the subject; and (b) comparing the level of expression or activity of the kinase gene or its encoded gene product determined in (a) to a control level of expression, wherein a higher level of expression or activity in the disease cells as compared to the control level of expression or activity indicates that the subject is a candidate for the treatment. In particular embodiments, a control level is a level determined in non-disease cells, e.g., non-disease cells of the same cell type, optionally obtained from the same subject, or a reference standard, e.g., a level previously determined for non-disease cells. In certain embodiments, the method further comprises providing to the subject an inhibitor of the kinase gene or encoded kinase, if the subject is determined to be a candidate for the treatment. In particular embodiments, the kinase gene is listed in FIG. 1C, FIG. 7 or FIG. 8. In one embodiment, the kinase gene is WEE1.

In another embodiment, the present invention includes a method of monitoring the progression or regression of a disease, e.g., a tumor, in response to a treatment, comprising: (a) determining a level of expression or activity of a kinase gene or its encoded gene product in disease cells, e.g., cancer cells, obtained from the subject prior to or at about the same time as providing the subject with the inhibitor; and (b) determining a level of expression or activity of a kinase gene or its encoded gene product in disease cells, e.g., cancer cells obtained from the subject following a time period after providing the subject with the inhibitor; wherein a reduced level of expression or activity determined for (b) as compared to the level of expression of activity determined for (a) indicates that the treatment is effective. In particular embodiments, the kinase gene is listed in FIG. 1C, FIG. 7 or FIG. 8. In one embodiment, the kinase gene is WEE1.

In certain embodiment, the reduction in kinase activity is determined by comparing the activity to a reference standard. In a further embodiment, the reference standard is a similar disease cell that is not contacted with the inhibitor agent. In another embodiment, the reference standard is the same disease cell before it is contacted with the inhibitor agent.

A person of skill in the art will understand that kinase expression or activity levels, e.g., a reduction in kinase activity or expression, can be ascertained at the DNA, mRNA, and protein levels. Accordingly, in one embodiment, the reduction in kinase expression can be determined based on monitoring the transcriptional activity of the reduction in kinase, i.e., the relative abundance of RNA gene product. For example, commonly known methods can by applied to measure abundance of mRNA gene product, such as PCR, quantitative RT PCR. Another method is a nuclease protection assay, wherein an antisense probe (labeled with, e.g., radiolabeled or nonisotopic) hybridizes in solution to an RNA sample. Following hybridization, single-stranded, unhybridized probe and RNA are degraded by nucleases and intensity of antisense probe is determined for double stranded molecules. In yet another embodiment, Northern blot assays are used to detect and ascertain the relative amounts of RNA, such as mRNA, in a sample according to conventional Northern hybridization techniques known in the art.

In additional embodiments, RNA need not be extracted from the disease cell or control cell. For example, fluorescent in situ hybridization can be used to determine the presence, relative quantity, and spatial distribution of target mRNA in a cell. In an illustrative example, Single Molecule RNA FISH (Biosearch Technologies, Novato, Calif.) uses multiple short singly labeled oligonucleotide probes complementary to distinct portions of the target sequence. When each probe binds to the single stranded mRNA template, it causes cooperative unwinding of the mRNA, promoting the binding of the additional probes. The net result is the binding of a large multitude of fluorescent labels to a single molecule of mRNA template, providing sufficient fluorescence to reliably locate each target mRNA in a wide-field fluorescent microscopy image.

Detectable probes, RNA interference molecules and the like useful for any of the methods described herein may be constructed according to well-known techniques based on the sequence of the kinase gene, or naturally occurring variants thereof.

In another embodiment, the reduction in kinase activity can be determined based on monitoring the amount of the polypeptide kinase in the sample. For example, immunoassays such as Western blot involve immunoprecipitation of protein from a sample according to methods well-known in the art. This is followed by sodium dodecyl sulfate polyacrylamide gel electrophoresis (SDS-PAGE) of the protein sample. After separation of the proteins, immunocytochemistry and the like can by used to determine the amount of the kinase present in the sample. A preferred agent for detecting a protein of interest is detectable antibody, or fragment thereof, capable of binding to the kinase.

Antibodies can be generated utilizing standard techniques well known to those of skill in the art. Such antibodies can be polyclonal, or more preferably, monoclonal. An intact antibody, or an antibody fragment (e.g., Fab or F(ab')2), can be used. Detectable probes, such as antibodies and the like, useful for any of the methods described herein may be constructed according to well-known techniques utilizing polypeptide moieties containing aspects of the polypeptide sequence of the kinase, or naturally occurring variants or derivatives thereof.

Additionally, antibodies, or fragments thereof can be employed histologically, as in immunofluorescence or immunoelectron microscopy, for in situ detection of kinase protein. In situ detection can be accomplished by obtaining a histological specimen (e.g., a biopsy specimen or immobilized cell culture) and applying thereto a labeled antibody that is directed to the kinase polypeptide. The antibody (or fragment) is preferably applied onto a biological sample. Through the use of such a procedure, it is possible to determine not only the presence of the protein of interest, but also its distribution within the sample. A wide variety of well-known histological methods (such as staining procedures) can be utilized in order to achieve such in situ detection.

Antibodies can be detected via direct labeling of the antibody via, e.g., coupling (i.e., physically linking) a detectable substance to the antibody, or indirect labeling of the antibody by reactivity with another reagent that is directly labeled. Examples of indirect labeling include detection of a primary antibody using a fluorescently labeled secondary antibody. In some embodiments, the biological sample can be brought in contact with and immobilized onto a solid phase support or carrier such as nitrocellulose, or other solid support which is capable of immobilizing cells, cell particles or soluble proteins. The support can then be washed with suitable buffers followed by treatment with the detectably labeled fingerprint gene-specific antibody. The solid phase support can then be washed with the buffer a second time to remove unbound antibody. The amount of bound label on solid support can then be detected by conventional means. A wide variety of known signaling mechanisms are also available for the described immunoassays, such as fluorescein isothiocyanate, rhodamine, phycoerythrin, phycocyanin, allophycocyanin, o-phthaldehyde fluorescamine, and the like.

In another embodiment, the reduction in kinase activity can be determined based on monitoring the enzymatic activity levels of the kinase in a standard kinase assay.

In some embodiments, the composition comprising an inhibitor is effective to selectively inhibit the growth and/or proliferation of the disease cells, while not inhibiting the growth and proliferation of non-disease cells.

Administration of the composition comprising an inhibitor effective to inhibit the growth and/or proliferation of the disease cells can be performed according to a variety of well-known methods, which can include providing the inhibitor in a pharmaceutical composition, e.g., comprising a pharmaceutically acceptable diluent, carrier, or excipient. The inhibitor or pharmaceutical composition comprising the inhibitor may be provided to a cell in vitro (in cell culture), or administered to a mammalian subject in vivo by any mode known in the art which retains inhibitor activity and provides access to the disease cells. These include, without limitation, oral, parenteral, intravenous, intraperitoneal, subcutaneous, intramuscular, and intrathecal routes of administration.

Inhibitors that may be used are described in detail infra. However, in certain embodiments, the inhibitor comprises a small molecule, a polynucleotide, or a polypeptide. In certain embodiments, the polynucleotide is an antisense RNA, an siRNA, or an miRNA. In certain embodiments, the polypeptide is an antibody or functional fragment thereof, or an aptamer. In certain embodiments, the inhibitor is a small molecule.

Kinase Inhibitors

Inhibitors of any of the kinase therapeutic targets described herein may be used to practice various embodiments of the present invention, e.g., to treat or prevent a tumor is a subject. In particular embodiments, a kinase inhibitor acts through any of a variety of mechanisms that are either direct or indirect. Accordingly, kinase inhibitors can inhibit kinases at the DNA, mRNA, or polypeptide levels, targeting transcription, translation, or functional enzyme (kinase) activity. Kinase inhibitors may be polynucleotides (e.g., DNA or RNA, single-stranded, double-stranded or triple-stranded), polypeptides (e.g., peptides, proteins, or antibodies or fragments thereof), or small molecules, or a mixture thereof. These types of inhibitors may be prepared according to methods known and available in the art.

In one embodiment, the inhibitor reduces the expression of a target kinase, thus reducing the levels of polypeptide product, i.e., the kinase. For example, inhibition of expression can be performed by an agent that physically binds to the DNA encoding the kinase, thus preventing access to the gene for transcription of the full length mRNA. Inhibition of transcription can also be accomplished, for example, by modification of the chromatin structure corresponding to the kinase gene locus. In another embodiment, the inhibitory agent binds to or modifies the kinase mRNA molecules to prevent translation into the kinase polypeptide. This can be accomplished, for example, using RNA interference. In particular embodiments, inhibitors are siRNAs, shRNAs or miRNAs. Such agents that selectively inhibit a target gene may be identified and prepared using methods known and available in the art, including various publicly available algorithms and software to select preferential binding sites on a target gene or mRNA. Sequences of illustrative siRNAs that may be used according to the methods of the present invention are provided in FIGS. 7 and 8.

In another embodiment, the kinase inhibitor inhibits kinase enzyme activity by binding to the kinase, e.g., the kinase domain, or interfering with its ability to bind or phosphorylate its substrate. In certain embodiments, kinase inhibitors are antibodies, or fragments thereof, that bind to a target kinase. Antibodies that specifically bind a target can be generated utilizing standard techniques well known to those of skill in the art, e.g., utilizing polypeptide moieties containing aspects of the polypeptide sequence of the target kinase. Such antibodies can be polyclonal or monoclonal. An intact antibody, or an antibody fragment (e.g., Fab or F(ab')2), can be used.

In certain embodiments, a kinase inhibitor is a small molecule. Illustrative, non-limiting examples of such kinase inhibitors include small molecules, such as IC261, PF-4800567, and PF-670462. The structures of these inhibitors are provided in PCT Publication No. 2011/127202. Additional kinase inhibitors include the WEE1 inhibitors, MK-1775 (also referred to as AZD1775) and 681640; the ALK inhibitor, TAE684; the PI3K inhibitor, PI828; the PIK4CB inhibitor, PIK93; the FYN inhibitor, PP2; the FAK inhibitor, PF-562271; and the CHK1 inhibitor, AZD7762; and pharmaceutically acceptable salts thereof. Illustrative structures of these kinase and other inhibitors or pharmaceutically acceptable salts thereof are provided below:

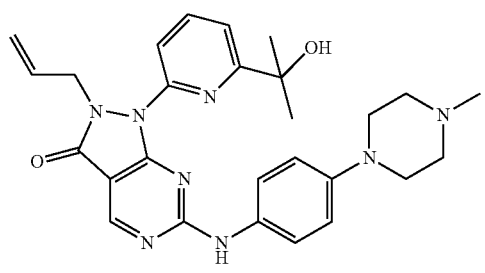

MK-1775

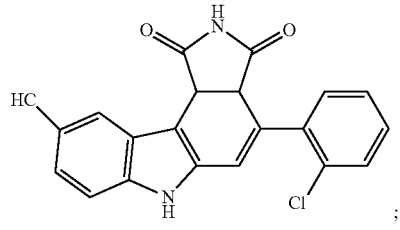

681640

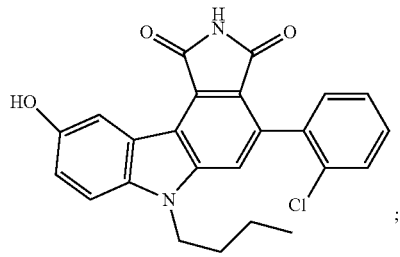

681641

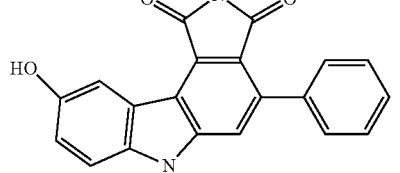

681637

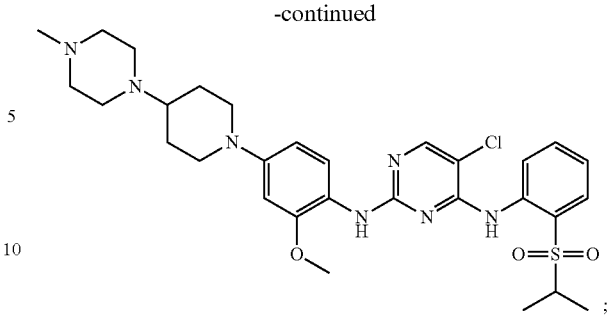

TAE684

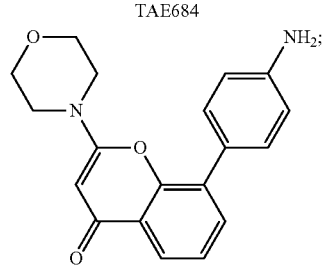

PI828

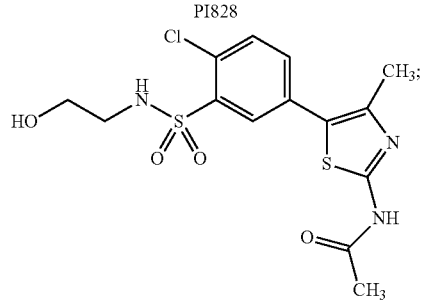

PIK93

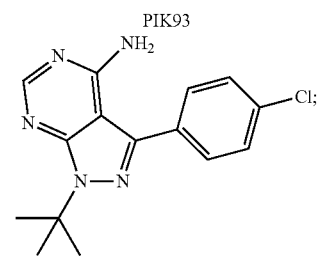

PP2

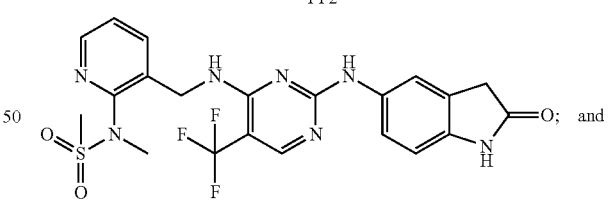

PF-562271 benzenesulfonate salt

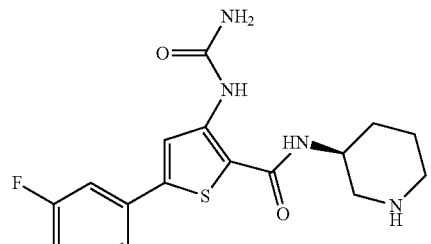

AZD7762

These kinase inhibitors, as well as other kinase inhibitors known in the art, can be used as therapeutic agents, e.g., in the treatment of cancers with p53 mutations, including head and neck squamous cell carcinomas, in vivo and in vitro, in accordance with the methods described herein. In particular embodiments, a kinase inhibitor is used to treat a cancer where the kinase it inhibits has been identified as a therapeutic target according to a method described herein.

Methods of Identifying Therapeutic Targets and Therapeutic Agents and Treating and Preventing Diseases As described in the accompanying Examples, the present invention includes novel methods of identifying therapeutic targets for various diseases. In particular embodiments, these methods utilize one or more of: (i) high throughput screening to identify therapeutic targets in a disease cell; (ii) target confirmation by high throughput screening of candidate therapeutic targets in disease cells of a different species; and (iii) in vitro and/or in vitro functional target validation. In certain embodiments, these methods are used to identify one or more therapeutic targets common to a particular type of disease, e.g., a particular type of cancer. In addition, in particular embodiments, these methods are used to identify one or more therapeutic targets for a particular disease cell in a particular subject, in a form of personalized medicine. Knowledge of therapeutic targets allows the selection of active agents to use to treat the disease. In certain embodiments, the active agents inhibit the expression or activity of a therapeutic target, while in other embodiments, they inhibit the expression or activity of another gene or protein in the same biological pathway as the therapeutic target.

In certain aspects, methods of identifying a therapeutic target for the treatment or prevention of a disease comprise: (a) screening a plurality of inhibitory agents, e.g., siRNAs, for their ability to inhibit growth or reduce viability of a diseased cell; and (b) identifying one or more genes targeted by one or more inhibitory agents of (a) that inhibit growth or reduce viability of the disease cell. In particular embodiments, the inhibitory agents inhibit the expression or activity of a gene or its encoded polypeptide. In certain embodiments, methods further comprise the step of obtaining a biological sample comprising a disease or mutant cell from a subject. In particular embodiments, the subject has been diagnosed with or is considered at risk of developing a disease or mutation.

In one embodiment, a method of identifying a therapeutic drug target in a diseased cell comprises: (a) screening a plurality of inhibitory agents, e.g., siRNAs, for their ability to inhibit growth or reduce viability of a mammalian diseased cell, or a mammalian cell having a defined mutation, of a first species; (b) identifying one or more genes targeted by one or more inhibitory agents of (a) that inhibit growth or reduce viability of the mammalian cell of the first species; (c) screening a plurality of inhibitory agents, e.g., siRNAs, for their ability to inhibit growth or reduce viability of a mammalian diseased cell, or a mammalian cell having a defined mutation, of a second species; (d) identifying one or more genes targeted by one or more inhibitory agents of (c) that inhibit growth or reduce viability of the mammalian cell of the second species; and (e) determining one or more genes identified according to both (b) and (d), wherein the diseased cell of the first species and the diseased cell of the second species share the same disease, or the mutation in the cell of the first species is in the same gene as the mutation in the cell of the second species, and wherein the one or more genes determined according to (e) or their encoded products are identified as therapeutic drug targets. In certain embodiments, the first species is human, and the second species in a non-human mammal, such as a non-human primate or a mouse.

In certain embodiments, the methods further comprise validating the therapeutic targets that are identified either in vitro or in vivo, e.g., by determining the ability of an inhibitor of an identified therapeutic target to inhibit growth of other related or unrelated disease cells. In certain embodiments, this includes determining the ability of an inhibitor of an identified therapeutic target to inhibit non-diseased cell, in order to identify and optionally eliminate targets that are not specific to diseased cells, or which have an undesired effect on non-diseased cells. In vivo validation methods include, e.g., the use of animal models of disease, including non-human animal xenograft models of disease, such as non-human animals having human tumor cells grafted to them.

In certain embodiments, the inhibitory agents are screened by contacting the disease cell or mutated cell with the inhibitory agents, e.g., by infecting or transfecting cells with the inhibitory agent or a vector that expresses the inhibitory agent. In particular embodiment, the screening is performed using cells in a microarray. In certain embodiments, the effect of the plurality of inhibitors is determined by examining one or more cell phenotype using a microscope or plate reader. In certain embodiments, the one or more phenotype includes cell growth or proliferation (e.g., growth rate), cell death (e.g., apoptosis), or secretion of one or more growth factors or cytokines.

Although any types of inhibitors may be used, in particular embodiments, the inhibitory agents are polynucleotides that each selectively inhibit expression of a target gene. In certain embodiments, the inhibitory agents are RNA interference agents, siRNAs, shRNAs, or miRNAs. In certain embodiments, the plurality of inhibitory agents target genes of a particular class or that encode a particular class of proteins, such as, e.g., kinases, transcription factors, transcriptional activators, transcriptional repressors, G protein coupled receptors, apoptosis inhibitors, oncogenes, or tumor suppressor genes. In certain embodiments, the inhibitory agents are peptides or proteins, such as antibodies or fragments thereof, or haptens, including those that bind to kinases, transcription factors, transcriptional activators, transcriptional repressors, G protein coupled receptors, apoptosis inhibitors, oncogenes, or tumor suppressor genes, including any of the kinase targets identified herein (see, e.g., FIGS. 1C, 2, 7 and 8). In other embodiments, the inhibitory agents are small molecules. Candidate compounds useful in the screening method include compounds from chemical libraries. Representative useful chemical libraries include libraries of structurally diverse compounds, libraries of therapeutic drug-like compounds, and libraries of therapeutic drugs approved by the Food and Drug Administration (FDA).

In certain embodiments, the disease cell or mutant cell is a tumor cell, such as a primary tumor cell. In particular embodiments, the tumor cell comprises a mutation in a tumor suppressor gene. In particular embodiments, the tumor suppressor gene is a DNA-PKcs, Atm, $p19^{Arf}$, p53, Hras, Kras, or Prkdc gene. In certain embodiments, the tumor cell has a mutation in both a p53 tumor suppressor gene and one or more of a Hras or Kras gene. In various embodiments, the tumor is a solid tumor or a liquid tumor. In particular embodiments, the tumor is a head or neck cancer, a breast cancer, a prostate cancer, a brain cancer, a thyroid cancer, a lung cancer, an ovarian cancer, a stomach cancer, a pancreatic cancer, a liver cancer, a skin cancer, a leukemia, a lymphoma, a colon cancer, a cervical cancer, a uterine cancer, an esophageal cancer, or a bladder cancer.

In related embodiments, the present invention includes methods of treating or preventing a disease in a subject that involve determining the therapeutic agent to use based on the results obtained by a methods described herein for identifying therapeutic targets. Thus, in certain embodiments, methods for treating or preventing a disease, e.g., a cancer, in a subject in need thereof, comprise: (a) screening a plurality of inhibitory agents, e.g., siRNAs, for their ability to inhibit growth or reduce viability of a disease cell obtained from the subject; (b) identifying one or more genes targeted by one or more inhibitory agents of (a) that inhibit growth or reduce viability of the disease cell; and (c) providing to the subject an inhibitor of one or more of the genes identified in (b). In particular embodiments, the methods further comprises: (d) obtaining a biological sample comprising a disease cell from the subject.

In other related embodiments, methods for treating or preventing a disease, e.g., a cancer, in a subject in need thereof, comprise: (a) obtaining, ordering or requesting the results of a test comprising: (i) screening a plurality of inhibitory agents, e.g., siRNAs, for their ability to inhibit growth or reduce viability of a disease cell obtained from the subject; and (ii) identifying one or more genes targeted by one or more inhibitory agents of (i) that inhibit growth or reduce viability of the disease cell; and (b) providing to the subject an inhibitor of one or more of the genes identified according to (a).

In particular embodiments, the disease is a cancer, e.g., a head or neck cancer, a breast cancer, a prostate cancer, a brain cancer, a thyroid cancer, a lung cancer, an ovarian cancer, a stomach cancer, a pancreatic cancer, a liver cancer, a skin cancer, a leukemia, or a lymphoma.

In certain embodiments, the plurality of inhibitory agents target kinases, transcription factors, transcriptional activators, transcriptional repressors, G protein coupled receptors, apoptosis inhibitors, oncogenes, or tumor suppressor genes.

In particular embodiments, the inhibitor is provided to the subject in combination with another therapeutic agent, e.g., another therapeutic agent used for treatment of the subject's disease.

EXAMPLES

Example 1

Identification of Therapeutic Drug Targets for p53 Mutant Head and Neck Squamous Cell Carcinoma Briefly, and as described in more detail below, RNAi kinome viability screens were performed on HNSCC cells including autologous pairs from primary tumor and recurrent/metastatic lesions, and in parallel on murine squamous cell carcinoma (MSCC) cells derived from tumors of inbred mice bearing germline mutations in Trp53, and p53 regulatory genes: Atm, Prkdc, and p19$^{Arf}$. Cross-species analysis of cell lines stratified by p53 mutational status and metastatic phenotype was utilized to select 38 kinase targets. Both primary and secondary RNAi validation assays were performed on additional HNSCC cell lines to credential these kinase targets utilizing multiple phenotypic endpoints. Kinase targets were also examined via chemical inhibition utilizing a panel of kinase inhibitors. A preclinical study was conducted on the WEE1 kinase inhibitor, MK-1775.

This functional kinomics approach identified novel survival kinases in HNSCC involved in G2/M cell cycle checkpoint, SFK, PI3K and FAK pathways. RNAi mediated knockdown and chemical inhibition of the WEE1 kinase with a specific inhibitor, MK-1775, had a significant effect on both viability and apoptosis. Sensitivity to the MK-1775 kinase inhibitor is in part determined by p53 mutational status, and due to unscheduled mitotic entry. MK-1775 displays single-agent activity and potentiates the efficacy of cisplatin in a p53 mutant HNSCC xenograft model.

This study demonstrated that WEE1 kinase is a potential therapeutic drug target for HNSCC, and also supports the application of a functional kinomics strategy to identify novel therapeutic targets for cancer.

Experimental Design

For this study, we hypothesized that HNSCC cancer cells, in particular those with p53 mutations, are dependent on particular kinases for survival and that targeting these kinases could have therapeutic potential. To identify these cancer-specific survival kinases, we utilized an unbiased and genome scale high-throughput (HT) siRNA gene silencing strategy. We surveyed the entire human kinome to identify those kinases that are required for survival of HNSCC cells stratified by p53 mutational status and metastatic propensity. We included pairs of HNSCC cells derived from primary tumors and either recurrent or metastatic lesions. The cell lines derived from the recurrent or metastatic tumors have been shown by us and others to have more aggressive features than their primary tumor autologous pairs, as measured by migration, avoidance of anoikis, and metastatic potential in mouse orthotopic xenografts (Methods for details) (9).

Recurrent/metastatic tumors are generally resistant to standard of care therapies and so are most in need of targeted therapies. The rationale for targeting kinases in human cancer is significant. These enzymes regulate multiple cellular processes that contribute to tumor development and progression, and many human tumors display aberrant activation of kinases caused by genetic alterations. For tumors that are dependent on kinase activity for survival, targeted drugs could be effective.

Understanding that human cancer cell lines exhibit genetic and phenotypic heterogeneity, which can hamper the identification of robust drug targets, we performed a parallel siRNA kinome screen using a set of low passage murine squamous cell carcinoma (MSCC) cells. These cancer cells were derived from tumors of inbred mice bearing germline mutations in p53 and p53 regulatory genes Atm, Prkdc, and p19$^{Arf}$ (10-13).

This set of p53 pathway deficient cancer cells share the same culture history and genetic background and were derived from tumors sharing the same etiology. The ability to query a set of cells with defects in key regulators of the p53 response facilitates the nomination of kinase targets against p53 deficient cancers. Finally, comparative analysis of siRNA screen results between mouse and human cells points to survival kinases that are conserved between species and likely represent the most robust drug targets. Through an efficient in vitro and in vivo prioritization and validation scheme, we identified the G2/M cell cycle regulatory kinase WEE1 as one of several clinically promising targets, and show that inhibition of WEE1 with a highly specific small molecule inhibitor impaired growth of p53 mutant HNSCC tumors in vivo.

Materials and Methods

Cell Lines

The following human HNSCC cell lines were used: UM-SCC14A, UM-SCC14C, PCI-15A, PCI-15B, JHU-019, UM-SCC22A, UM-SCC22B; UM-SCC38; UM-SCC17A and UM-SCC47 (5, 14-18). Three cell line pairs were derived from primary tumors and subsequent recurrences or metastatic cervical lymph nodes from the same patients: UM-SCC14A, and UM-SCC14C; PCI-15A and PCI-15B; and UM-SCC22A and UM-SCC22B. Cell line JHU-019 was derived from a late-stage OSCC patient (19, 20). The cell lines had the following characteristics.

TABLE 1

Characteristics of HSNCC Cell Lines

| Cell Line | Site of Origin in Patient | Metastasis Status of Patient | Form Tumor in Xenograft | Metastasize to Neck Lymph Node in Xenograft | P53 Status and Mutation |
|---|---|---|---|---|---|
| JHU-019 | Tongue | Positive lymph node | yes | yes | mutated frameshift and early termination at 169 caused by deletion at 138 |
| PCI-15A* | Oral cavity | Positive lymph node | yes/no | no | mutated T126Stop |
| PCI-15B* | 3$^{rd}$ recurrence | Positive lymph node | yes | yes | mutated R273C |
| UM-SCC14A* | Floor of mouth | Negative lymph node | yes | no | mutated R280S |
| UM-SCC14C* | 3$^{rd}$ recurrence | Negative lymph node | yes | n/a | mutated R280S |
| UM-SCC22A* | Hypopharynx | Positive lymph node | n/a | yes | mutated Y220C |
| UM-SCC22B* | Lymph node metastasis | Positive lymph node | n/a | yes | mutated Y220C |
| UM-SCC17A | Larynx | Negative lymph node | n/a | n/a | wild-type |
| UM-SCC47 | Oral cavity | Positive lymph node | n/a | n/a | wild-type |

*Cell line pairs derived from the primary tumors and subsequent recurrences or metastasis
NM = no mutation For the paired lines, wound-healing assays revealed that the migration rate of cell lines derived from metastatic HNSCC (i.e. UM-SCC-14C and PCI-15B) was higher than those derived from the primary tumor (i.e., UM-SCC-14A and PCI-15A) and that JHU-019 had the fastest migration rate (Xu, C. et al., PLoS Genet 2013; 9:e1003169). In addition, JHU-019 and PCI-15B cell lines tested in mouse xenografts by orthotopic injection into the tongue produced squamous carcinoma at the sites of injection and cervical lymph node metastasis (Xu, C. et al., PLoS Genet 2013; 9:e1003169).

To determine p53 mutational status, we designed primers to amplify exons 2-11 using Primer3 software (Whitehead Institute, Cambridge, Mass.). Primer specificity was confirmed by gel electrophoresis. PCR-amplified fragments were purified and sequenced using an ABI 3730xl DNA Analyzer with ABI's BigDye Terminator Cycle Sequencing method. Sequencing results are aligned to GenBank TP53 sequence NG_017013.1 using Sequencher 4.10.1 (Gene Codes, Ann Arbor, Mich.). Cell lines were characterized for metastatic potential as described (Xu, C. et al., PLoS Genet 2013; 9:e1003169). To determine if a p53 mutation is disruptive, we used criteria established by Poeta et al. (Poeta, M L et al., N Engl J Med 2007; 357:2552-61).

Murine squamous cell carcinoma (MSCC) cells were derived from NIH/Ola strain mice with germline mutations in p53 pathway genes and included: MSCC-CK101 (Hras$^{Q61L}$ Trp53$^{+/+}$), MSCC-CK102 (Hras$^{Q61L}$ Trp53$^{+/-}$), MSCC-CK103 (Hras$^{wt}$ p19Arf$^{-/-}$), MSCC-CK104 (Kras$^{G13R}$ Atm$^{-/-}$), MSCC-CK1 (Hras$^{Q61L}$ p53$^{+/+}$) and MSCC-CK4 (Hras$^{Q61L}$ p53$^{-/-(Cre+}$ $^{p53}$ $^{lox/lox)}$) (10-12). MSCC-CK105 (Hras$^{Q61L}$ Prkdc$^{mu/mu}$) cells were from SCID mutant mice of a mixed C3H/Balb/c background (13) The cell lines had the following characteristics.

TABLE 2

Characteristics of MSCC Cell Lines with Germline Mutations in the p53 Pathway

| Cell Line | Genotype (Germline Mutation) | Treatment | Strain Background | Ras status | P53 Status and Mutation |
|---|---|---|---|---|---|
| MSCC-CK101 | Wild-type | DMBA/TPA | NIH/Ola | Hras Q61L (CAA → CTA) | Trp53 +/+ Exons 5-8 (NM) |
| MSCC-CK102 | Trp53 +/− | DMBA/TPA | NIH/Ola | Hras Q61L (CAA → CTA) | Trp53 +/− Exons 5-8 (NM) Δexon 5 (106 bp) |
| MSCC-CK103 | P19Arf −/− | DMBA/TPA | NIH/Ola | Hras wt | Trp53 +/+ Exons 5-8 (NM) |
| MSCC-CK104 | Atm −/− | DMBA/TPA | NIH/Ola | Kras G13R (GGC → CGC) | Trp53 +/+ Exons 5-8 (NM) |
| MSCC-CK105 | Prkdc mu/mu | DMBA/TPA | CH3/Balb/c F1 | Kras Q61L (CAA → CTA) | Trp53 +/+ Exons 5-8 (NM) |
| MSCC- | Wild-type | DMBA/TPA | NIH/Ola | Kras Q61L | Trp53 +/+ |

TABLE 2-continued

Characteristics of MSCC Cell Lines with Germline Mutations in the p53 Pathway

| Cell Line | Genotype (Germline Mutation) | Treatment | Strain Background | Ras status | P53 Status and Mutation |
|---|---|---|---|---|---|
| CK1 | (Trp53 +/+) | | | (CAA → CTA) Kras Q61L | Exons 2-11 (NM) |
| MSCC-CK4 | Trp53 −/− (Cre + Trp53 lox/lox) | DMBA/TPA | NIH/Ola | (CAA → CTA) | Trp 53 −/− n/a |

NM = no mutation

All mice were subjected to the identical DMBA/TPA two-stage carcinogen protocol to induce squamous cell carcinoma. Tumors induced by this protocol principally harbor an activating mutation in the Hras oncogene, but mutations in Kras have also been noted. Carcinomas arising from both p19$^{Arf}$ and p53 deficient mice are highly aggressive and metastatic. Mouse SCC lines were derived using a standard outgrowth explant method. Briefly, carcinoma tissue was washed in sterile PBS, sliced into 2 mm pieces using a sterile razor blade, and placed into a 60 mm tissue culture plate with DMEM media, 10% FCS and Pen/Strep. Media was replaced every 72 hours until cell outgrowths reached 70-90% confluence, and were subsequently passaged and/or frozen at low passage number. Total RNA was isolated from the MSCC-CK1 line with TrIzol and cDNA generated utilizing Superscript 3 reverse transcriptase (Life Technologies). The p53 cDNA transcript spanning exons 2-11 was PCR amplified as previously described (Wang et al., Cancer Cell 2009; 16:33-43), and cloned into a TOPO TA vector (Life Technologies), competent cells transformed, and several colonies sequenced using an ABI 3730xl DNA Analyzer with ABI's BigDye Terminator Cycle Sequencing method for mutations in the p53 gene.

High-Throughput RNA Interference Kinome Screens

Kinome-wide siRNA screens were performed with viability as the phenotypic endpoint on five HNSCC lines: JHU-019; PCI15A and 15B; UM-SCC14A and 14C; and five MSCC lines: MSCC-CK101, MSCC-CK102, MSCC-CK103, MSCC-CK104, MSCC-CK105. Normal human foreskin fibroblasts were screened to control for nonspecific cell toxicity. Briefly, culturing of normal human foreskin fibroblasts was performed as previously described (Kiyono, T. et al., Nature 1998; 396:84-8). Kinome-wide RNA interference screens were performed on two cultures of human foreskin fibroblasts (HFF1, HFF3) utilizing the Ambion kinome library (Ambion-Life Technologies, Grand Island, N.Y., USA). An HFF exclusion plot was generated using this kinome screen information to determine whether RNAi mediated knockdown of kinase targets compromised cell viability in both HFF cultures, with <70% viability (>30% cell death) as a threshold. siRNA libraries targeting 713 human (MISSION® siRNA Human Gene Family Set, Sigma-Aldrich, St. Louis, Mo., USA; also available through the Quellos High Throughput Facility at the University of Washington Institute for Stem Cell and Regenerative Medicine, Seattle, Wash. USA) and 572 murine kinases (Ambion-Life Technologies) were constructed and utilized in pools of 3 independent siRNAs targeting each gene, in a one gene per well approach. RNAi screens were performed in 384-well format utilizing robotics instrumentation (Toyoshima, M. et al., Proc Natl Acad Sci USA 2012; 109:9545-50). Transfection feasibility of each cell line was established using a factorial optimization. Mock condition and a non-targeting universal siRNA control were utilized as negative controls, while a siRNA directed at KIF11 (kinesin-like protein), which arrests cells in mitosis was utilized as a positive control. All reagent conditions were statistically evaluated using a simple Z-factor score to evaluate differentials and variability of replicates (i.e. potent cell killing with KIF11 at the lowest toxicity possible in the mock universal controls) to select an optimized transfection condition for each cell line (Zhang, J H et al., J Biomol Screen 1999; 4:67-73). All kinases were tested in triplicate to establish experimental variability and statistical validity. Scrambled siRNA negative controls were used to monitor dynamic range and off-target effects and the results were standardized to mock-transfected cells. Viability and apoptosis were quantified utilizing an Envision Multilabel detector/plate reader (Perkin Elmer) with either a CellTiterGlo assay (Promega), or Apotox assay (Promega), the former measures metabolic ATP via a standard curve to mock/universal siRNA at all conditions. Raw luminescence values were then Z transformed per cell line and plotted for distribution and data mining (Miner 3D software, version 7.3). All HT kinome screens and subsequent validation screens on MSCC and HNSCC cells were statistically evaluated using published methods (Birmingham, A. et al., Nat Methods 2009; 6:569-75).

Comparison of Human and Mouse Kinome Screens

The 713 human and 572 murine kinase sets were cross-referenced utilizing mouse genome informatics (MGI) (http://wwwdotinformaticsdotjaxdot.org/) and National Center for Biotechnology Information (NCBI) (http://wwwdotncbidotnlmdotnihdotgov/) database nomenclature to generate a common list of 508 kinases referred to as the interspecies kinome. Using this common list, prioritization of screen results then followed based on the viability scores from the 5 HNSCC cells and 5 MSCC cell lines. Mean viabilities ($\mu_{i2}$) from 5 HNSCC cell lines [$\mu i_{2\ All\ (human)} = \mu_i$ (O19)+$\mu_i$ (14A)+$\mu_i$ (14C)+$\mu_i$ (15A)+$\mu_i$ (15B)] and from 5 MSCC cell lines were calculated [$\mu_{i2\ All\ (murine)} = \mu_i$ (WT)+$\mu_i$ (Trp53+/−)+$\mu_i$ (p19$^{Arf}$−/−)+$\mu_i$ (Atm−/−)+$\mu_i$ (Prkdc mu/mu)] for each of 508 kinases {i=1, 2, 3, 4 ... 508}, where $\mu_i$ is the triplicate of pooled siRNAs (3 distinct siRNAs) average normalized viability for each individual gene per cell line. Mean viabilities ($\mu_{i2}$) for each gene were then Z transformed using the equation, $Z = \mu_{i2} - \mu/\sigma$ where $\mu$ is the mean viability and $\sigma$ the standard deviation for all siRNAs/wells for all 5 HNSCC cell lines and all 5 MSCC cell lines, respectively. Mean viabilities ($\mu_{i2\ All}$, $\mu_{i3\ p53\ mutant}$, $\mu_{i4\ metastatic}$) and Z score transformations were calculated for both human and murine lines per genotype and phenotype for: (1) all human and murine cell lines; (2) p53 mutant/deficient human and murine cell lines; and (3) metastatic human and murine cell lines. Cartesian plots (Z-score$_{murine}$, Z-score$_{human}$) of all 508 kinases in common with murine and human kinomes were then generated for each of the three comparisons. Population mean viabilities (Mean$_{All}$, Mean$_{p53\ mutant\ All}$, Mean$_{Metastatic}$)

and Z-score transformations (Z-score$_{Mean\ All}$, Z-score$_{p53\ mutant\ All}$, Z-score$_{Mean\ Met}$) were calculated for specific genotypic and phenotypic comparisons and utilized in the color-coded overlay on the cartesian plots for selection per comparison. Kinase targets were selected based on Z-score threshold from each of the cartesian plots: Z-score$_{Mean\ All}$<−1.0; Z-score$_{p53\ mutant\ All}$<−2.0, Z-score$_{Mean\ Met}$<−1.5, where kinases were data mined from more then one comparison and duplicates were removed for a final selection of 38 kinase targets from all three comparisons, kinase targets (38 kinases)=kinase targets$_{All}$+kinase targets$_{p53\ mutant}$+kinase targets$_{Met}$ (FIGS. 1B and 1C). These kinases included serine/threonine kinase 32B (STK32B); aurora kinase A (AURKA); galactokinase 2 (GALK2); thymidine kinase 2 (TK2), mitochondrial NUAK family, SNF1-like kinase 2 (NUAK2); calcium/calmodulin dependent protein kinase II beta (CAMK2B); membrane protein, palmitoylated 3 (MAGUK) (MPP3); serine/arginine rich protein specific kinase 3 (STK23); phosphatidylinositol-4-phosphate 5-kinase, type 1, beta (PIP5K1B); glycerol kinase 2 (GK2); ribosomal protein S6 kinase-like 1 (RPS6KL1); phosphatidylinositol 4-kinase, catalytic, beta (PIK4CB); FYN oncogene related to SRC, FGR, YES (FYN); eukaryotic translation-initiation factor 2 alpha kinase 3 (EIF2AK3); inhibitor of kappa light polypeptide gene enhancer in B cells, kinase epsilon (IKBKE); Gardner-Rasheed feline sarcoma viral (v-fgr) oncogene homolog (FGR); mitogen-activated protein kinase kinase kinase 8 (MAP3K8); uridine-cytidine kinase 1-like 1 (UCKL1); tribbles homolog 2 (*Drosophila*) (TRIB2); eukaryotic translation-initiation factor 2 alpha kinase 4 (EIF2AK4); TXK tyrosine kinase (TXK); EPH receptor 3 (EPHA3); anti-Mullerian hormone receptor, type II (AMHR2); Wee1 homolog (*S. pombe*) (WEE1); Chk1 checkpoint homolog (*S. pombe*) (CHK1); mitogen-activated protein kinase 13 (MAPK13); TTK protein kinase (TTK); fms-related tyrosine kinase 1 (FLT1); phosphoinositide-3-kinase, catalytic, beta polypeptide (PIK3CB); Integrin-linked kinase (ILK); anaplastic lymphoma receptor tyrosine kinase (ALK); NIMA (never in mitosis gene a)-related expressed kinase 4 (NEK4); WNK lysine deficient protein kinase 4 (WNK4); c-abl oncogene 1, non-receptor tyrosine kinase (ABL1); v-erb-b2 erythroblastic leukemia viral oncogene homolog 3 (avian) (ERBB3); mitogen-activated protein kinase kinase kinase 2 (MAP3K2); fibroblast growth factor receptor 3 (FGFR3); and Protein kinase C, Epsilon (PKCE). Kinases were further prioritized based on those whose expression or activity was increased in squamous cell carcinoma (SCC) and that play known functions in SCC pathogenesis.

Primary Validation of Kinase Targets with siRNA

Twenty-eight kinases were selected for follow-up and validation based on the interspecies kinome comparison and HFF kinase exclusion, including ABL1, CANK2B, EIF2AK3, EIF2AK4, EPHA2, FGFR3, FGR, FYN, GALK2, IKBKE, ILK, MAP3K2, MAP3K8, MAPK13, MPP3, NEK4, NUAK2, PI4 KB, PRKCE, RPS6KL1, STK32B, TK2, TRIB2, TTK, TXK, UCKL1, WEE1, and WNK4. Two small-scale time-course primary validation RNAi screens were performed in parallel on four HNSCC cell lines (UM-SCC14A, UM-SCC14C, PCI-15A, PCI-15B) in 384-well formats with an independent set of siRNAs (Qiagen, FIG. 7), with three separate siRNAs plus pooled siRNAs per gene target in triplicate for an N=12 for each gene target. All phenotypic endpoints of cell viability and caspase 3/7-dependent apoptosis were measured in parallel screens in a time-course format at 1.5, 3, and 4.5 days post-transfection using the CellTiter-Glo assay (Promega) and Apotox-Glo (Caspase-Glo 3/7 reagent) assay (Promega) per manufacturers specifications and an Envision multilabel plate reader (PerkinElmer). Primary screen "hits" were assessed utilizing a single endpoint for cell viability at 4.5 days post-transfection termed, absolute viability, by both a negative-control independent analysis: triplicate siRNAs versus population mean of the screen, Z-score threshold and unpaired t-test, Z-score<−1.0, P<0.1 scored as hit, as well as a negative-control dependent analysis: triplicate siRNAs versus universal negative control siRNAs, ANOVA with Dunnetts post-test, mean difference>0 and P<0.05 scored as hit. Comparing post-transfection effects on absolute viability (day 4.5) for each kinase target with either the universal negative control siRNA or the population mean yielded similar results. Differential viabilities (day 4.5-1.5) based on the mean of both the N=12 data (i.e., all three distinct siRNAs per target plus pooled siRNAs in triplicate) and N=3 data (i.e., pooled siRNAs alone) were calculated for all 28 kinase targets listed in FIG. 7. AUC (area under the curve) estimates of caspase-dependent apoptosis (AUC$_{estimate}$) utilizing all three data points with both the N=12 data and N=3 pooled siRNAs were calculated for all kinase targets. Statistical significance of RNA interference mediated knockdown of the 28 kinases was assessed via ANOVA with Dunnetts post-test for multiple comparisons (P<0.05 as significant) on differential viability (day 4.5-day 1.5), and area under the curve (AUC) analysis of caspase 3/7 dependent apoptosis versus universal negative siRNA control (UNI).

Secondary Validation of Kinase Targets with siRNA

Ten kinase targets were further validated in a 96 well format in five additional HNSCC cell lines (UM-SCC22A, UM-SCC22B, UM-SCC38, UM-SCC47A, JHU-019). In addition, the ten HFF exclusion kinase targets were included in the low-throughput assay (i.e., 20 kinase targets listed in FIG. 8). This assay consisted of three independent siRNAs per well (pooled siRNAs) assayed in triplicate (Qiagen, FIG. 8) for cell viability and apoptosis measured at 1.5, 3, and 4.5 days post-transfection utilizing the Apotox-Glo assay (Promega, Madison, Wis.) as per manufacturers specifications utilizing a Synergy H4 Hybrid Multi-Mode microplate reader (Biotek). Statistical significance of RNA interference mediated knockdown of the 20 kinases was assessed via ANOVA with Dunnetts post-test for multiple comparisons on absolute viability (day 4.5), differential viability (day 4.5-day 1.5), and area under the curve (AUC) analysis of caspase dependent apoptosis versus the negative siRNA control (SINC).

Dose-Response Curves with Kinase Inhibitors

Kinase inhibition dose response curves were performed with six kinase inhibitors (MK-1775 (a.k.a., AZD-1774), TAE684, PI828, PIK93, PP2, PF-562271) against kinase targets (WEE1, ALK, PI3K, PIK4CB, FYN, FAK (ILK surrogate)), respectively. Kinase inhibitors: MK-1775 (S1525), PIK93 (S1489), TAE684 (S1108) were obtained from Selleck Chemicals (Houston, Tex.); PI828 (2814), PP2 (1407) from Tocris Bioscience (Mpls, Minn.), and PF-562271 from Synkinase (San Diego, Calif.). All HNSCC (UMSCC-17A, UM-SCC47A, PCI-15A, PCI-15B, UM-SCC14A, UM-SCC14C) and MSCC (CK1: p53+/+ and CK4: p53−/−) cells were plated at ~5-10×10$^3$ cells/100 μl per well, and incubated at 37° C. for ~24 hours on 96-well assay plates (Corning Inc.). Serial dilutions of the kinase inhibitors and vehicle control (DMSO) were prepared in 1 mL assay blocks at 3× working concentration to generate dose-response curves ranging from 100 μM to 0.03 μM. All serial dilutions were prepared using cell culture media.

Approximately 72 hours post-treatment, cells were assessed for metabolic activity via ATP using CellTiterGlo (Promega), following the protocol outlined by the manufacturer utilizing an FLx800, and/or a Synergy H4 Hybrid multi-mode reader (Biotek). All assays were performed in triplicate and normalized to wells with no treatment. Dose-response curves and $IC_{50}$ values were generated using GraphPad Prism Version 5 (Parameters: nonlinear regression fit; equation=log (inhibitor) vs. response–variable slope (four parameters); single constraint).

COSMIC Public Database of Drug Sensitivity Data

Utilizing the catalogue of somatic mutations in cancer (COSMIC) website, TP53 gene mutational status was extracted from the Sanger Cancer Cell Line Project which contains information on 820 cancer cell lines. In addition, the Genomics of Drug Sensitivity Project (Release 2 Jul. 2012) contains 541 cancer cell lines that were treated with a WEE1/CHK1 inhibitor, 681640 (EMD Millipore), a pyrrolocarbazole compound that acts as a potent, ATP-binding site inhibitor of WEE1 ($IC_{50}$=11 nM). Drug sensitivity was measured with 9 different concentrations of 681640 and half maximal inhibitory (50%) values presented as natural log (μM). The sign test was applied to test the median difference in sensitivity by TP53 status. We performed a similar analysis on only the squamous cell carcinoma (SCC) cell lines. Forty-two squamous cell lines were identified from COSMIC annotation, eight were p53 wild type and the remaining 34 had a p53 mutation.

Mitotic Entry, Cell Cycle Analysis, Apoptotic Assays

Mitotic entry was assessed as previously described (Aarts, M. et al, Cancer Discov 2012; 2:524-39). Briefly, HNSCC cells (PCI-15B, UMSCC-17A) were treated with 1 μM MK-1775 for 8 and 24 hours, and all cells were harvested, washed, and incubated with rabbit monoclonal antibody to phospho-histone H3 (Serine10) (Cell Signaling Technology, Cat. No. 3465, Danvers, Mass.) for 2 hours at RT, washed, and DNA stained with 20 μg/ml propidium iodide, RNaseA in PBS (Sigma-Aldrich; Cat. Nos. P4170, R6513). Flow cytometric analysis was performed utilizing a BD FACS Canto II, and profiles analyzed with BD Cell Quest software (Becton Dickinson, CA). Caspase-3/7 dependent apoptosis was assessed as per protocol (Promega, Cat. No. G8091) utilizing a SynergyH4 Hybrid Reader (Biotek, VT). AUCs were calculated for all treatments and vehicle (DMSO) for all cell lines utilizing two measurements over a 48-hour period with three concentrations (30 nm, 100 nm, 1 μM) of MK-1775.

Xenograft Tumor Model

PCI-15B cells were inoculated subcutaneously into the right flanks of 28 eight-week old NOD/SCID IL2 gamma null mice (NSG) provided by the Olson laboratory at the Fred Hutchinson Cancer Research Center. When tumors reached a palpable mass of >50 mm$^3$, mice were randomly assigned into four treatment groups of seven mice each and all measurements and treatment regimens were carried out using a double-blind protocol. The WEE1 inhibitor MK-1775 (S1525-Selleck Chemicals, Houston, Tex.) was delivered by oral gavage (30 mg/kg) twice per week for 4 weeks in dimethylsulfoxide in 0.5% methylcellulose (M0512, Sigma Aldrich) in a 1:14 suspension. Cisplatin (P4394, cis-diammineplatinum (II) dichloride, Sigma Aldrich) was delivered via intra-peritoneal injection (4.0 mg/kg) once a week for 4 weeks. The volume of the implanted tumor was measured weekly with calipers and tumor volumes calculated using the formula: $V=L \times W^2/2$; in which V, volume (mm$^3$); L, largest diameter (mm); W, smallest diameter (mm). All animal protocols were approved by the Fred Hutchinson Cancer Research Center Laboratory Animal Care and Use Committee.

Immunoblotting

Tumor tissues were minced and homogenized on ice in M-PER Mammalian Protein Extraction Reagent supplemented with Halt Protease and Phosphatase Inhibitor Cocktail (Thermo Fisher Scientific). Extracted proteins were quantified by a BCA protein assay (Thermo Fisher Scientific). Fifty μg of each protein specimen was revealed on a NuPAGE® 4-12% Bis-Tris mini gel (Life Technologies) and transferred onto an Immobilon-P PVDF membrane (Millipore, Billerica, Mass.). Anti-WEE1 (Cat. No. 4936), anti-phospho-WEE1 (Ser642) (Cat. No. 4910), anti-CDC2 (Cat. No. 9112), and anti-phospho-CDC2 (Tyr15) (Cat. No. 4539) antibodies were purchased from Cell Signaling Technology (Danvers, Mass.). The secondary antibodies used were ZyMax™ horseradish peroxidase (HRP) conjugated goat-anti-rabbit IgG (Life Technologies). HRP was detected with SuperSignal West Pico Chemiluminescent Substrate kit (Thermo Fisher Scientific).

Statistical Analysis

All column and curve data points presented as mean+/−sem, unless otherwise noted. All statistical analyses were performed using unpaired two-tailed t-tests unless otherwise indicated. All statistical analysis of RNAi interference primary and secondary screening data is described above and all calculations used for significance testing are presented in supplemental tables. Statistical tests were all performed utilizing Graphpad Prism versions 5 & 6 (GraphPad Software Inc., CA).

Results

RNA Interference Kinome Screens of Squamous Cell Carcinoma

We performed kinome wide siRNA viability screens on a set of five HNSCC cell lines (UM-SCC14A; UM-SCC14C; PCI-15A; PCI-15B and JHU-019). Two pairs of these cells (UM-SCC14A UM-SCC14C and PCI-15A, PCI-15B) were derived from primary and subsequent post-treatment recurrences or metastatic cervical lymph nodes from the same patients and all carried disruptive mutations in p53. A total of 713 kinases were interrogated using an arrayed siRNA platform that quantified cell viability following knockdown with a pool of 3 siRNAs/gene/well. All assays were performed in triplicate. Cell viability was monitored 4 days after siRNA transfection using the ATP-based, CellTiterGlo assay (see Methods for details). In parallel, we performed kinome-focused screens on a set of five low passage cancer cells derived from murine squamous cell carcinomas (MSCC). These cells were isolated from carcinoma bearing inbred mice harboring germline mutations in the p53 pathway genes Atm, Prkdc, p19$^{Arf}$, and Trp53.

Figure 1B:
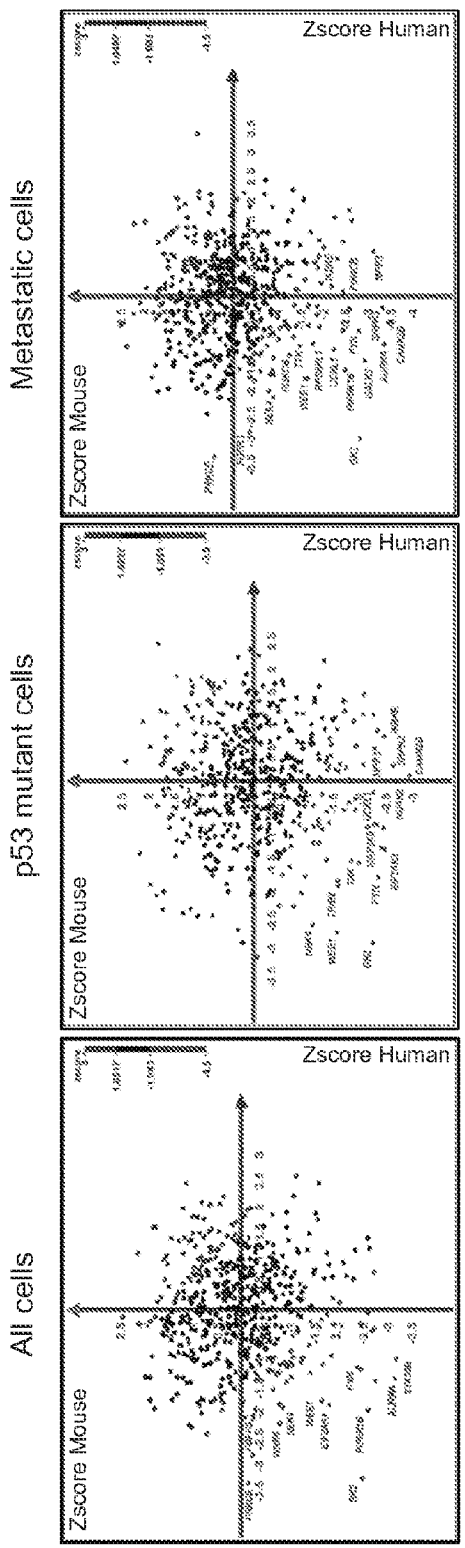
Figure 1C:
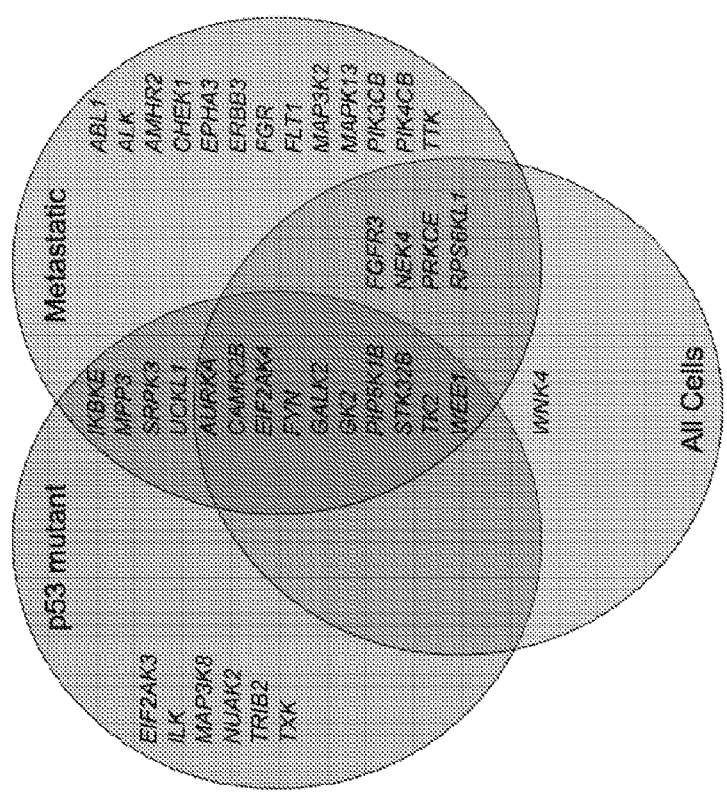

Next, we derived an interspecies kinome (508 kinases shared between both species) to identify kinases in which RNA interference mediated knockdown negatively impacted cell viability in both human and mouse cells (see schematic in FIG. 1A). Cell screens were further stratified by p53 mutant status and metastatic propensity. Cartesian plots with cross-species comparison of viability Z scores for all 508 kinases, for all cell lines (left), p53 mutant cell lines (middle), and metastatic cell lines (right) are shown in FIG. 1B. Thirty-eight kinases were selected for follow up based on several criteria, including shared negative Z scores in both species and specificity to cells with mutant p53 and metastatic phenotype (FIG. 1C). Many of these putative HNSCC survival kinases are implicated in signaling pathways such as focal adhesion and integrin signaling (CAMK2B, FYN, ILK, EPHA3, EIF2AK4, TRIB2), PI3K signaling (PIK4CB, PIK3CB, PIP5K1B, TRIB2, FGFR3, ALK), SRC signaling (FYN, TXK, CAM2 KB), and G2/M cell cycle regulation (WEE1, NEK4, TTK, AURKA, CHK1).

Figure 2A:
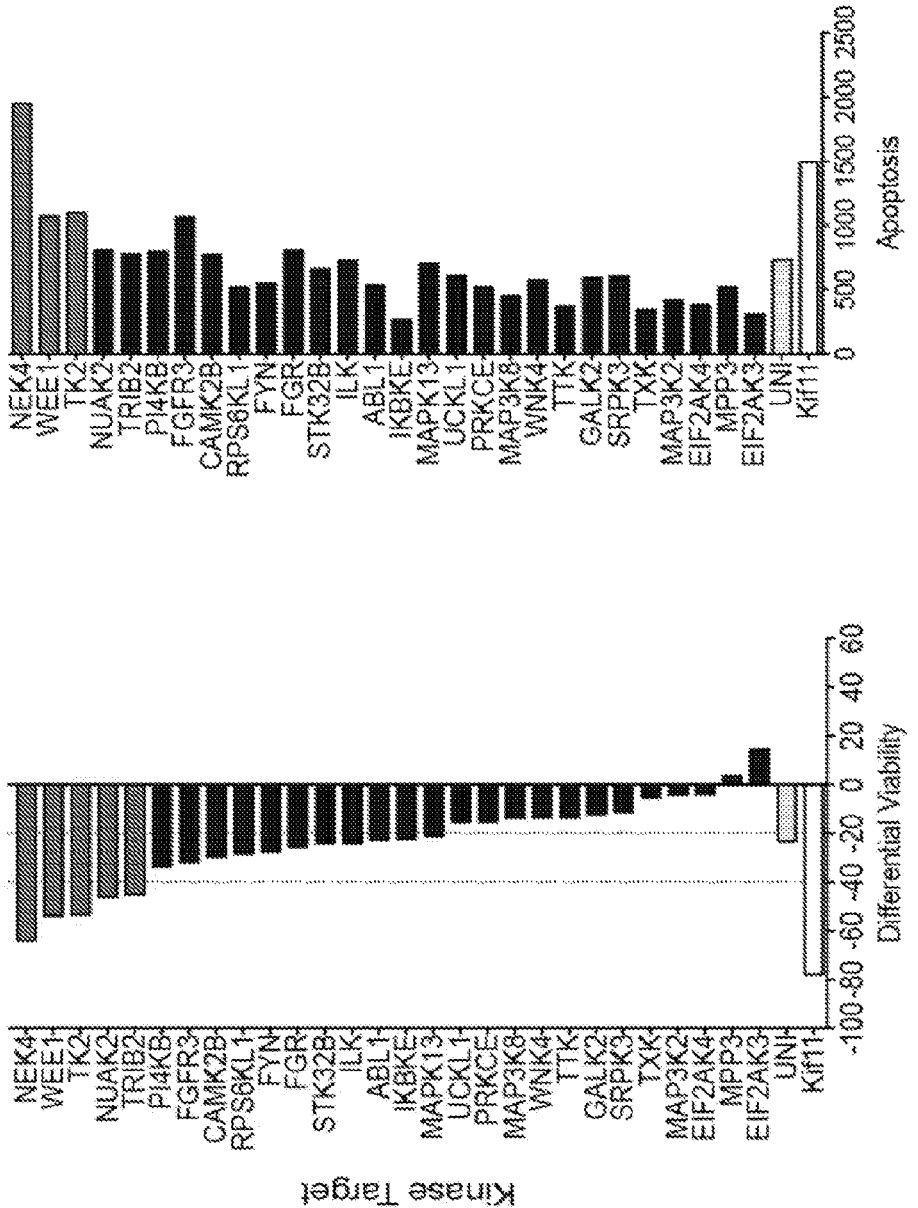
FIG. 2 provides bar graphs showing the results of RNA interference validation screens on kinase targets. A-I. RNAi primary validation screen; left bar graphs show differential cell viability (day 4.5-day 1.5) of RNAi-mediated knockdown of 28 kinase targets in autologous pairs of HNSCC cell lines derived from primary tumor and recurrent/metastatic site (14A, 14C, 15A, 15B); kinase target vs. UNI, P<0.05 (green); right bar graphs show caspase-dependent apoptosis integrated over 4.5 day time-course of RNAi-mediated knockdown of 28 kinase targets, kinase target vs. UNI, P<0.05 (blue); results ranked by differential viability for each kinase target per HNSCC cell line. Cell lines assayed include UMSCC-14A (A); UMSCC-14C (B); PCI-15A (C); and PCI-15B (D). E-I. RNAi secondary validation assays in five additional HNSCC cell lines (22A, 22B, 38, 47, 019); left bar graphs show differential cell viability (day 4.5-day 1.5) of RNAi-mediated knockdown of 20 kinase targets in HNSCC cell lines, kinase target vs. SINC, P<0.05 (J); right bar graphs show caspase-dependent apoptosis integrated over 4.5 day time-course of RNAi-mediated knockdown of 20 kinase targets in HNSCC cell lines, kinase target vs. SINC, P<0.05 (K), results ranked by differential viability for each kinase target per HNSCC cell line. Cell lines assayed include UMSCC-22A (E); UMSCC-22B (F); UMSCC-38 (G); UMSCC-47 (H); and JHU-019 (I). J and K. Kinase target significance in HNSCC. RNAi-mediated knockdown of kinase targets ranked by percentage of HNSCC cell lines in which kinase target reached statistical significance versus universal negative siRNA control. Differential viability (J); caspase 3/7 dependent apoptosis (K).
Figures 9A, 9B:
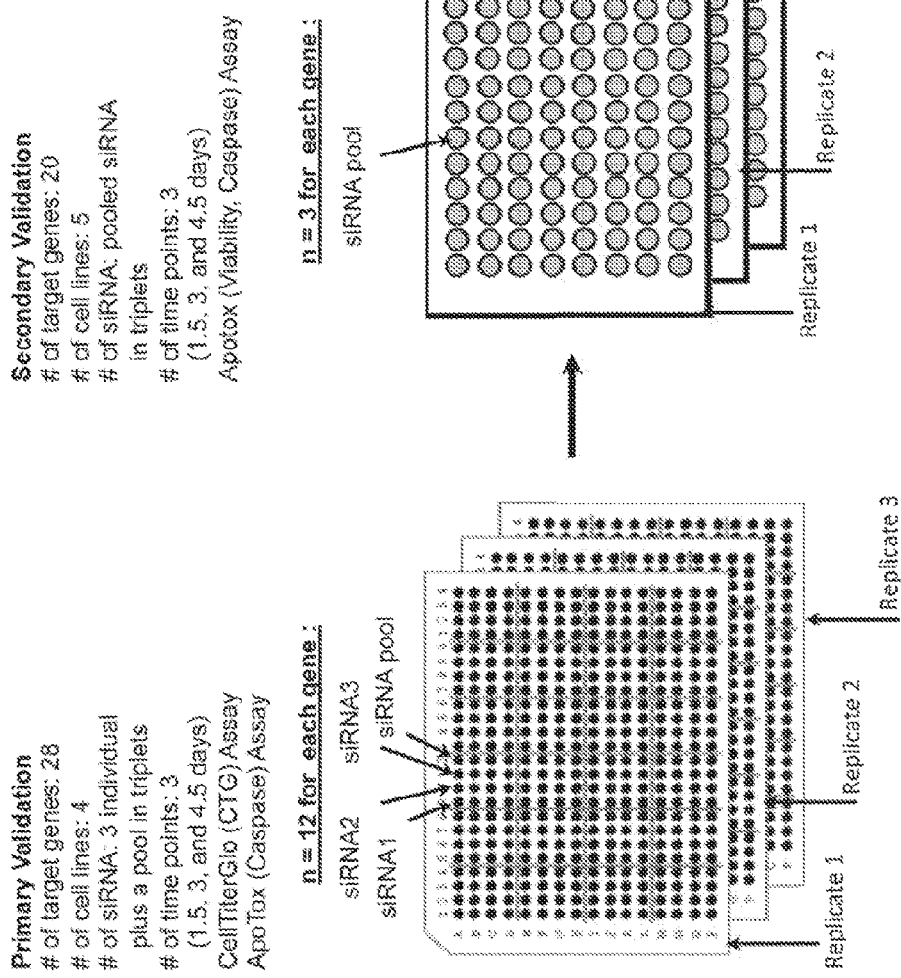
FIG. 9. Plate layouts for RNA interference mediated knockdown in HT RNAI primary validation screen (A) and secondary RNAI validation assay (B). Drawings of 384-well format for primary validation screen and 96-well format for secondary assay. Individual siRNAs and siRNA pooled approach depicted along with replicate plates; CellTiter-Glo assay (Promega) and Apotox-Glo assay (Promega).
Figure 10:
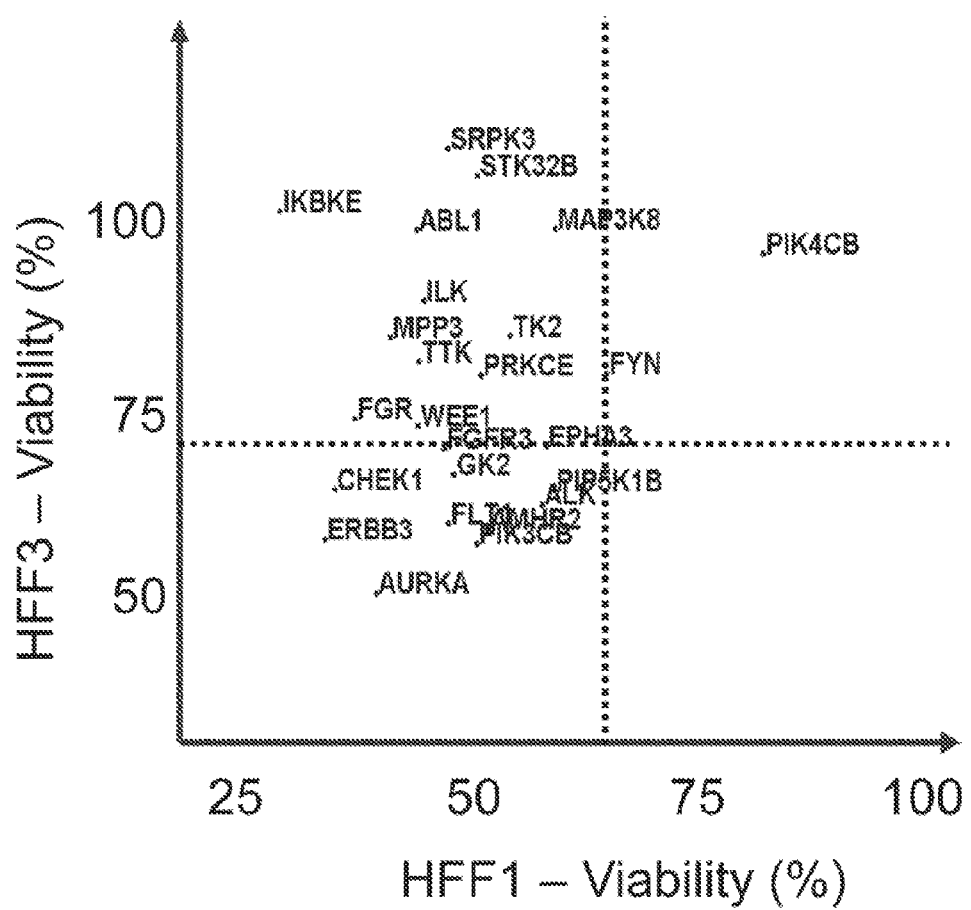
FIG. 10. Human foreskin fibroblast (HFF) kinase exclusion plot. The top 38 kinase targets where evaluated to determine whether RNAi mediated inhibition caused toxicity to normal cells utilizing kinome screening data on two HFFs primary cultures. The common lethal space is depicted in the left lower hand corner of the plot to indicate the kinases whose inhibition caused >30% loss in cell viability in both HFFs screens.

In order to prioritize targets for preclinical validation, we used primary cultures of human foreskin fibroblasts (HFF) to assess whether inhibition of these kinases caused toxicity to normal cells. Ten kinases caused >30% loss in cell viability in both HFF cultures (FIG. 10) and were not included in the primary validation screen. The remaining 28 kinase targets were retested with independent siRNAs on the same two pairs of autologous HNSCC cell lines (UM-SCC14A and 14C; PCI-15A and 15B) using a format of three separate siRNAs per gene plus a pool of all three siRNAs, each in triplicate (i.e., N=12 per gene) (FIG. 9). Both cell viability and caspase 3/7-dependent apoptosis were measured in parallel at 1.5, 3, and 4.5 days post-transfection. Differential viability (day 4.5-1.5), absolute viability (day 4.5), and apoptosis was calculated for each kinase (see Methods for details). Differential viabilities were calculated in order to measure post-transfection effects over time (day 4.5-1.5) and statistically evaluated versus the universal negative control siRNA (FIG. 2A). Differential viabilities calculated utilizing three separate siRNAs per gene plus the pool of all three siRNAs yielded comparable results.

Figure 2B:
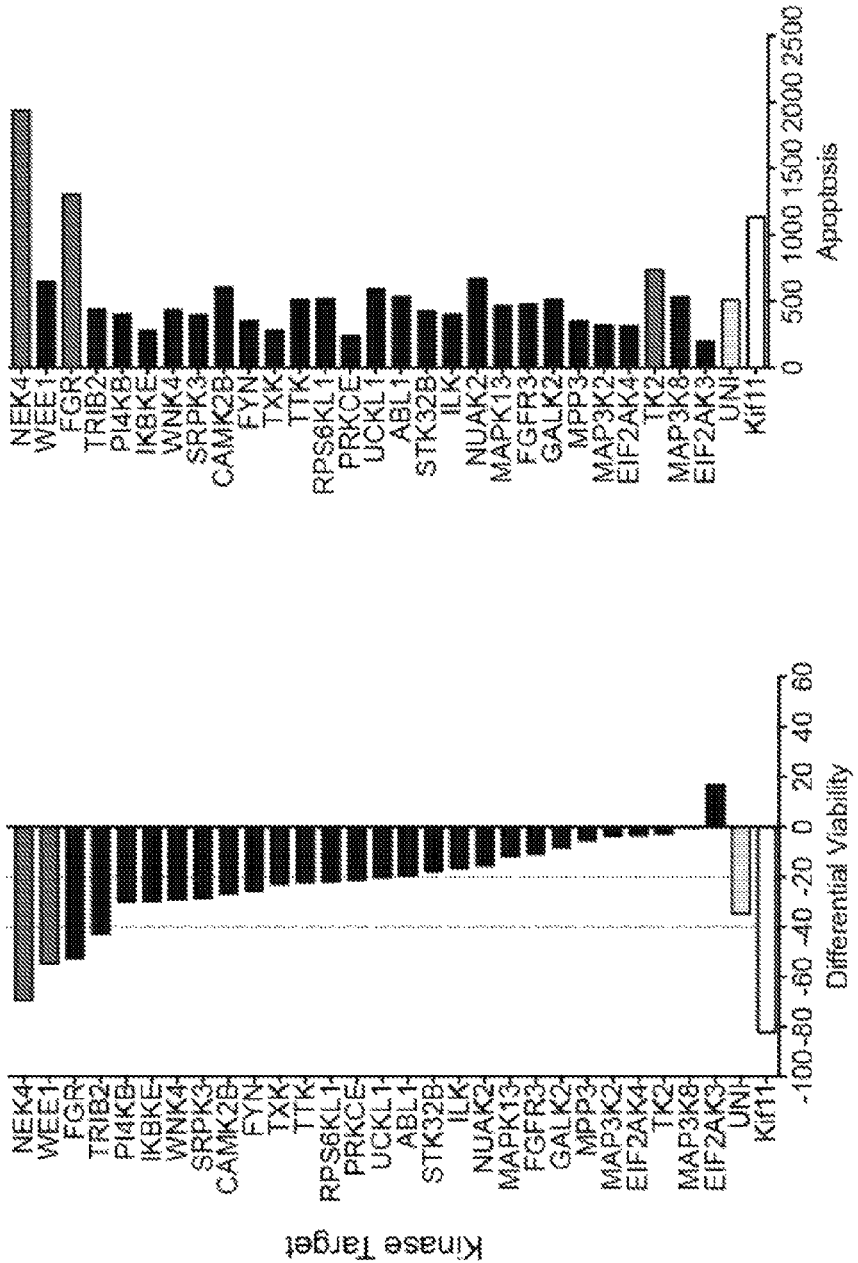

We focused on the pooled analysis to reduce off-target effects (31). Likewise, results obtained utilizing either differential or absolute viability metrics yielded similar prioritized kinase targets (see Methods for details). To measure the cumulative effects of RNAi mediated knock-down on apoptosis, area under the curve estimates of caspase-dependent apoptosis was determined versus the universal negative control siRNA (FIG. 9 and FIG. 2B). Results from this primary validation screen revealed that many of the kinase targets that significantly reduced viability also increased apoptosis (FIG. 2A). RNAi mediated knockdown of NEK4 and WEE1 kinases led to a significant reduction in cell viability in all four cell lines tested, while targeting TRIB2 did so for three of the four lines.

Ten kinase targets (NEK4, WEE1, ILK, CAM2 KB, FGFR3, FYN, PI4 KB (PIK4CB), TRIB2, TTK, TXK) that caused a significant reduction in viability and/or increase in apoptosis following siRNA transfection in at least one cell line were selected for secondary validation on five additional HNSCC lines (UM-SCC22A, UM-SCC22B, UM-SCC17, UM-SCC47 and UM-SCC38), and kinase target metrics were measured and calculated using the same format as above (FIG. 9). UM-SCC22A and UM-SCC22B are an autologous pair of cells derived from a primary tumor and cervical lymph node metastasis from the same patient. We also retested ten kinases from the discovery screen whose siRNAs reduced viability in HFFs (FIG. 2B and FIG. 9).

Figure 2C:
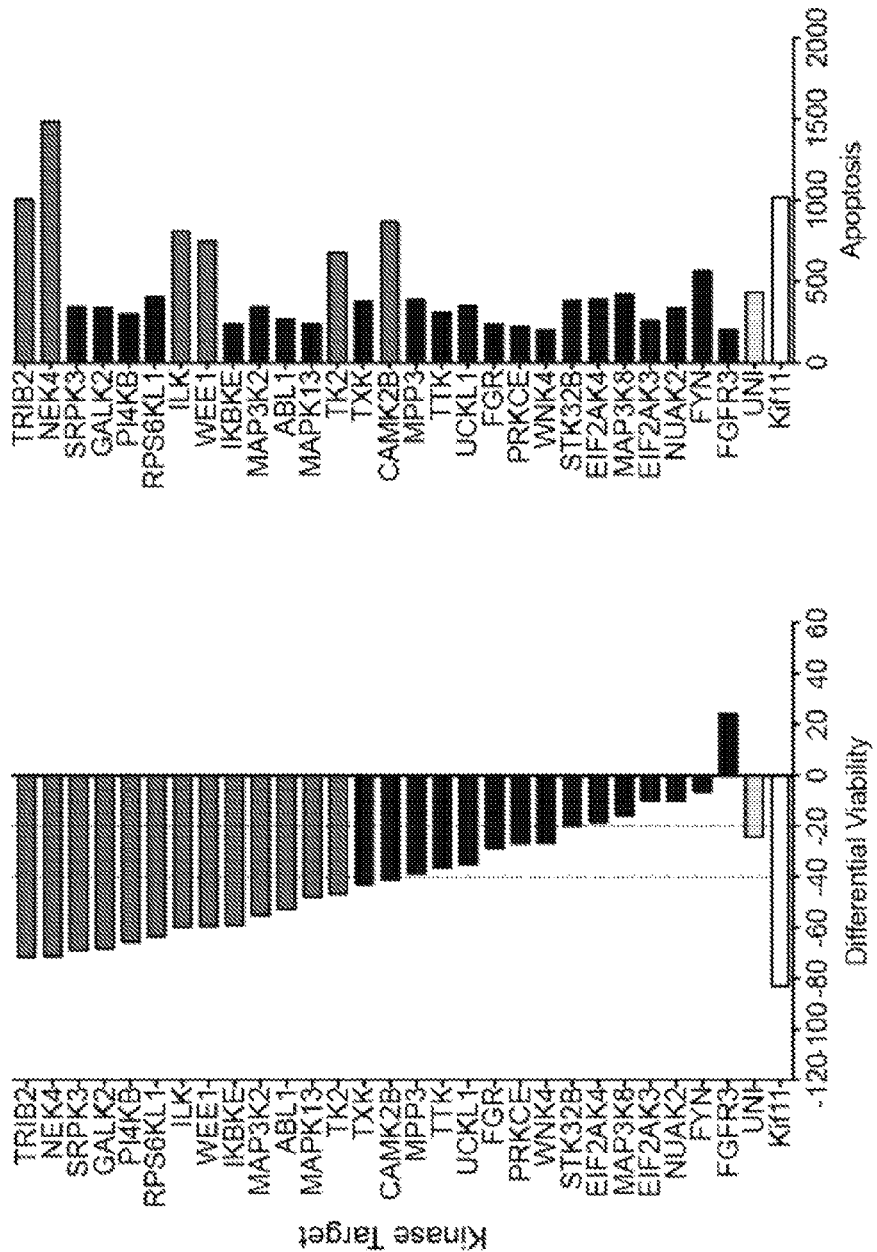
Figure 2D:
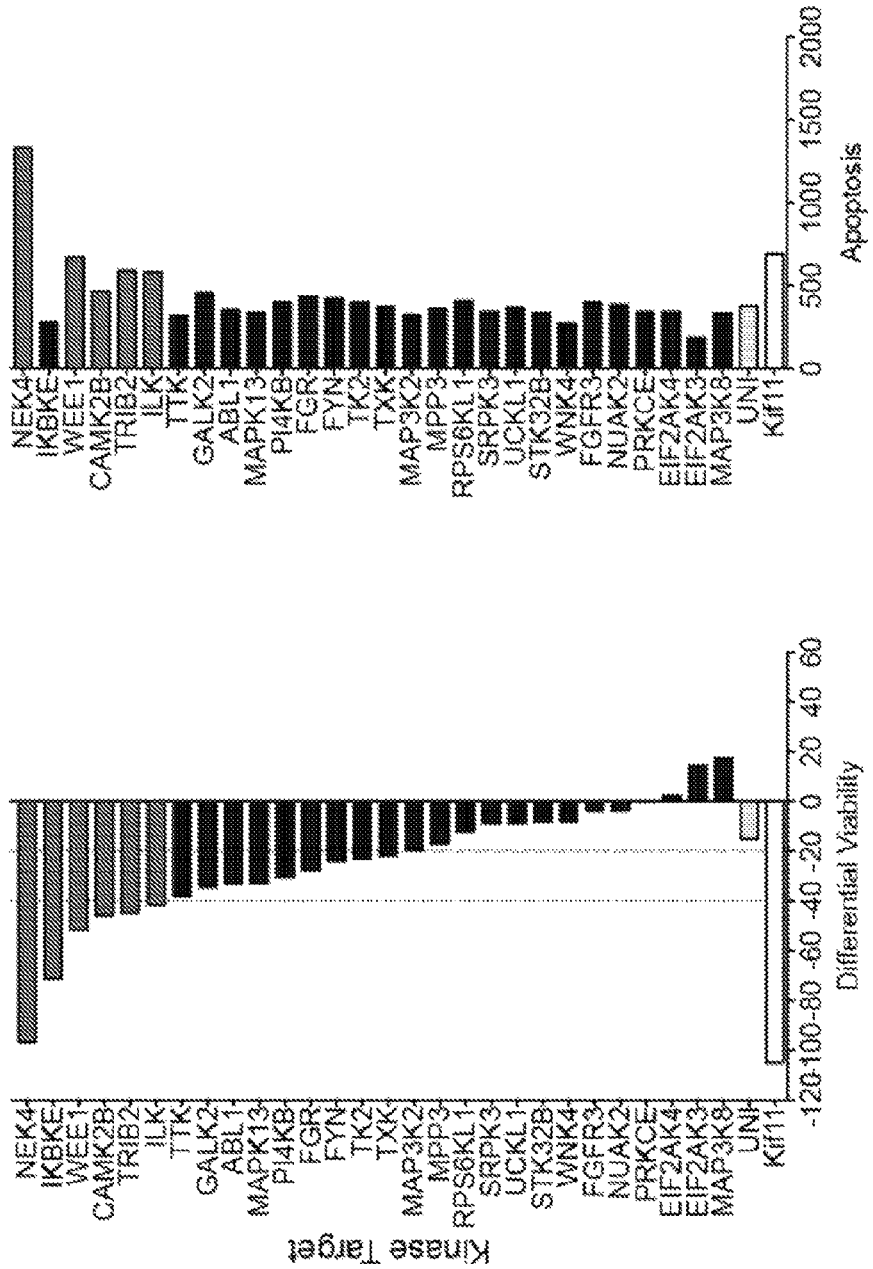
Figure 2E:
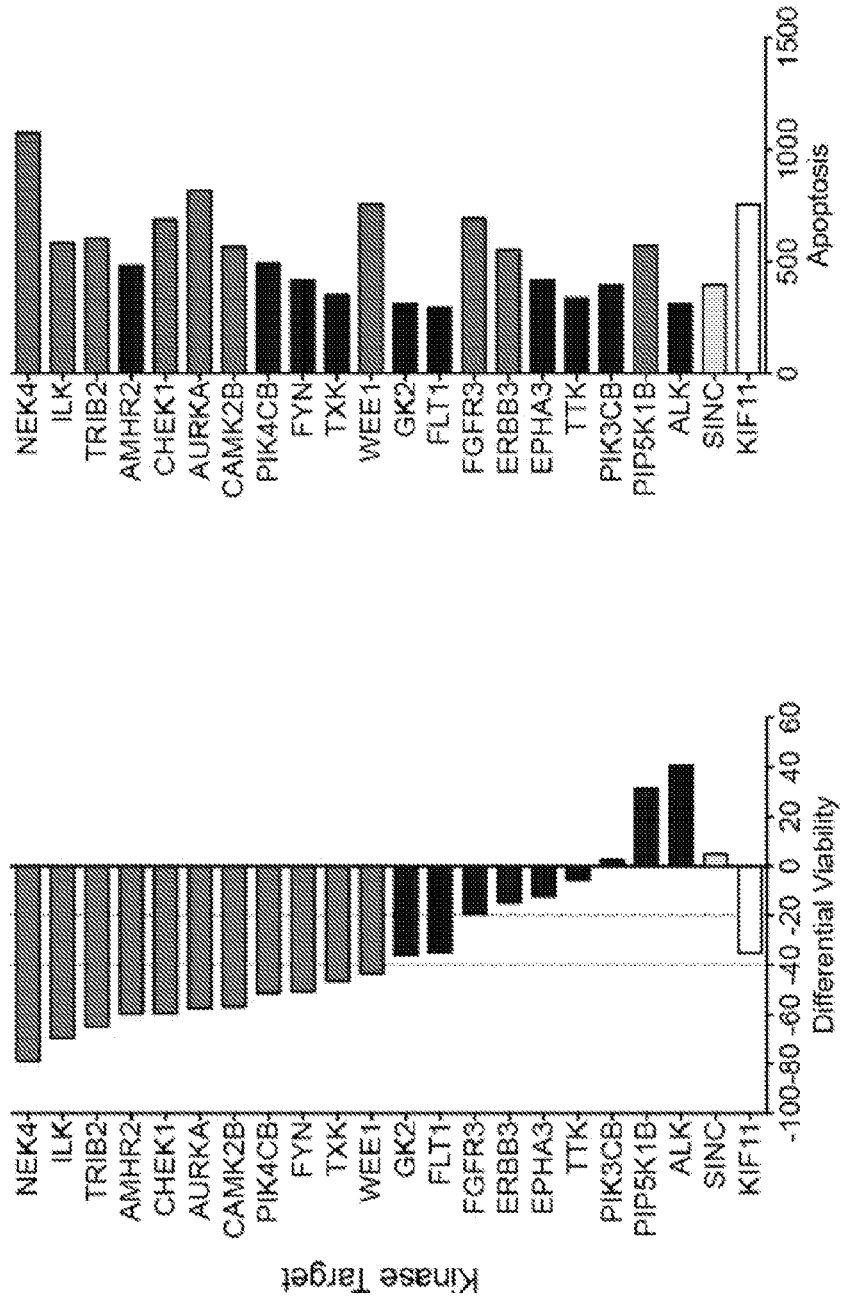
Figure 2F:
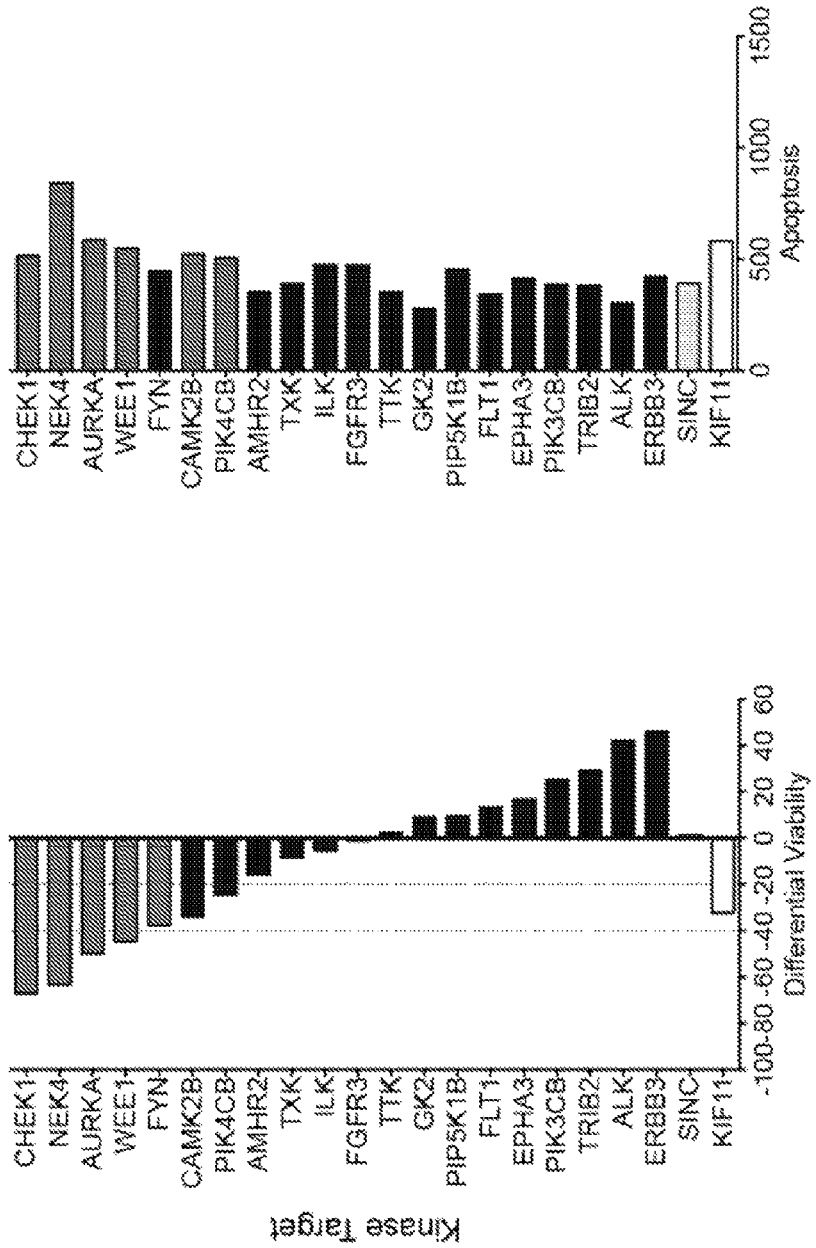
Figure 2G:
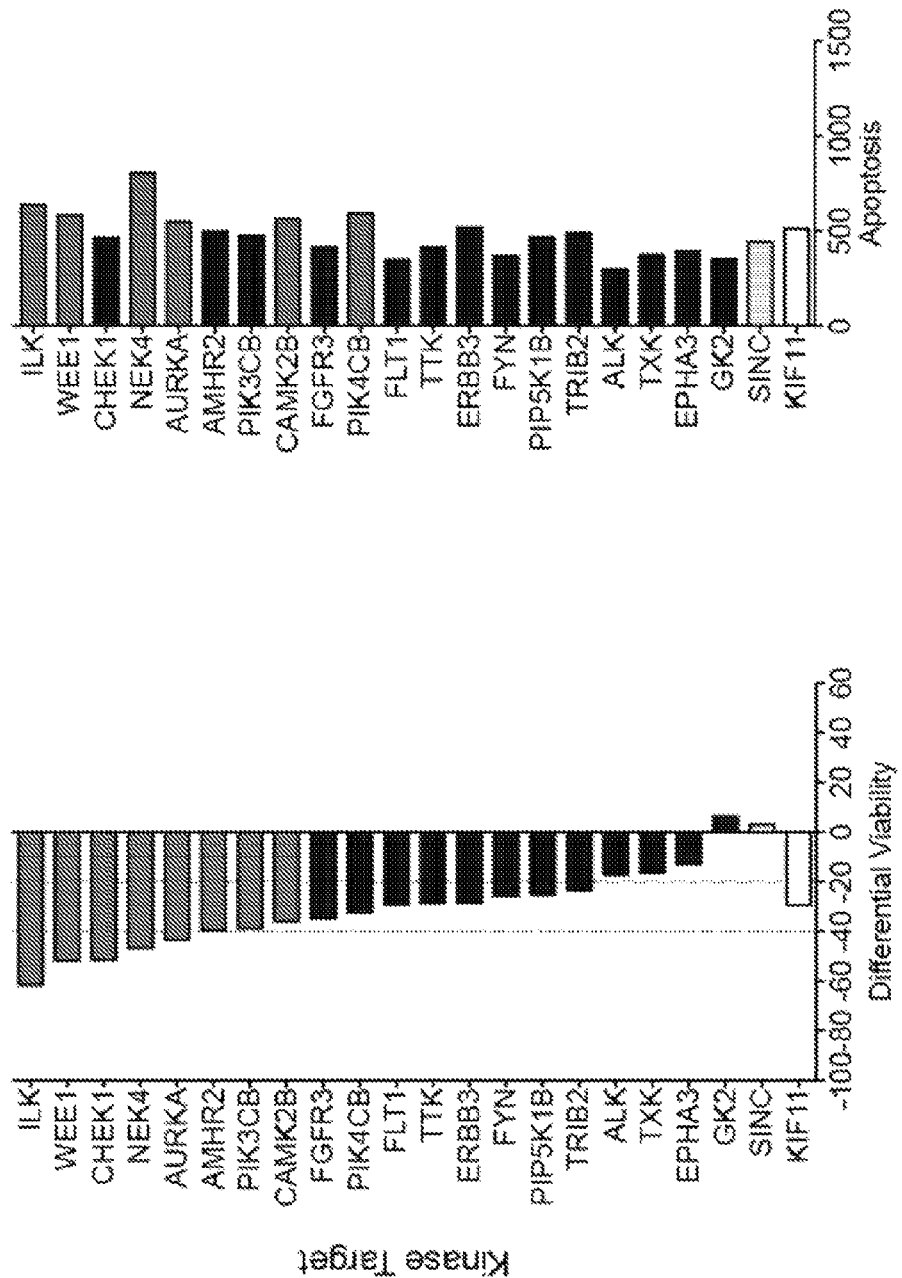
Figure 2H:
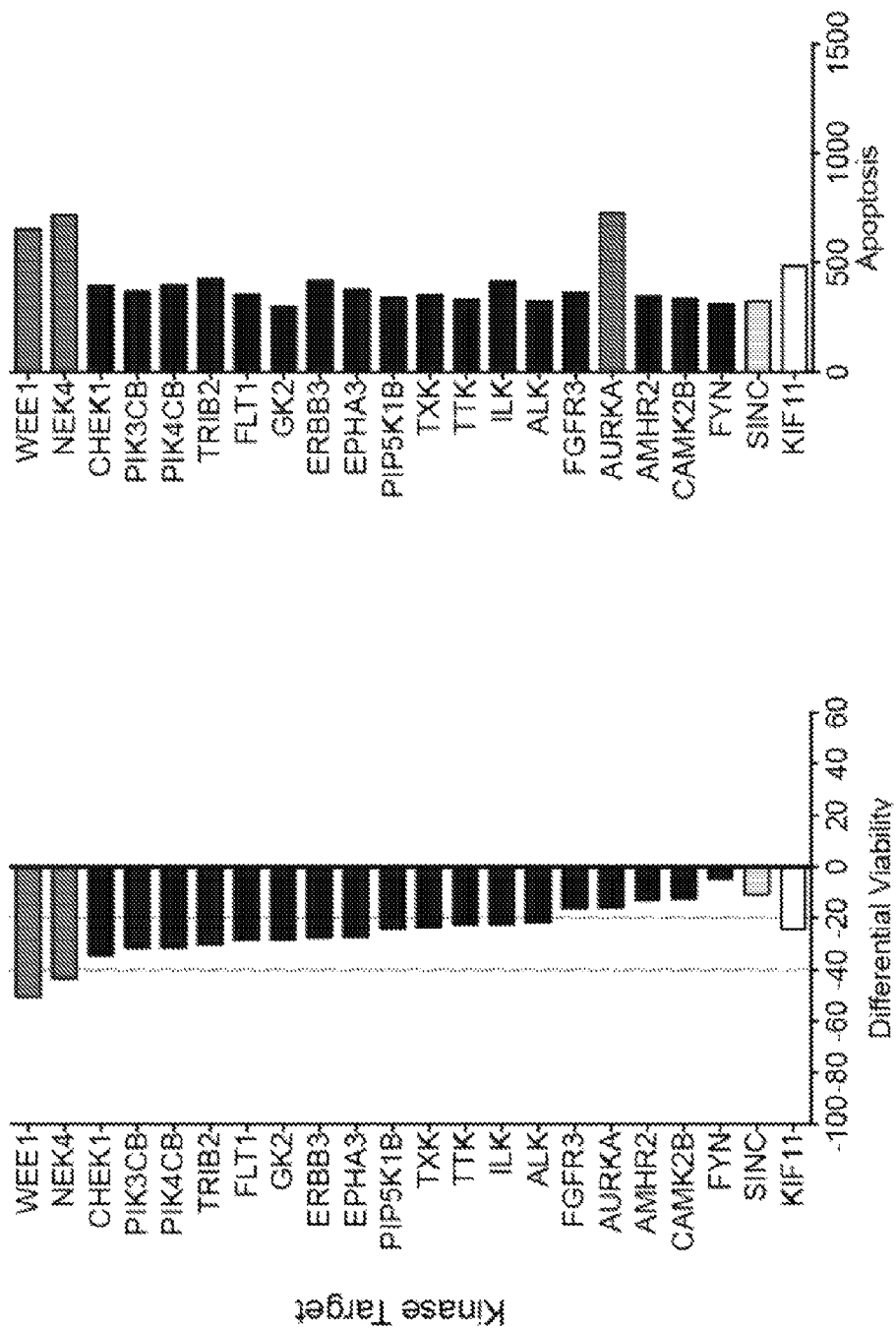
Figure 2I:
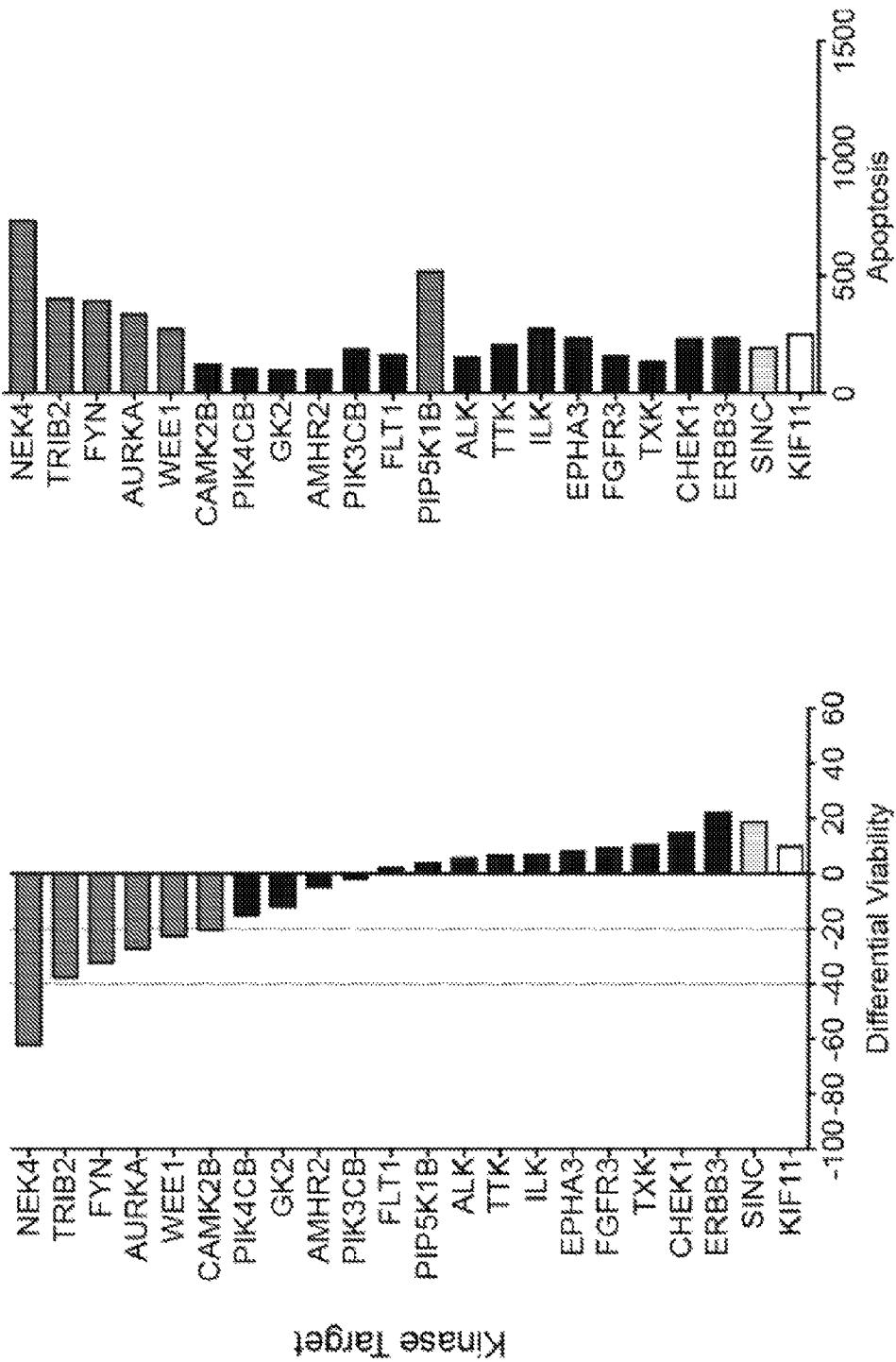
Figure 2J:
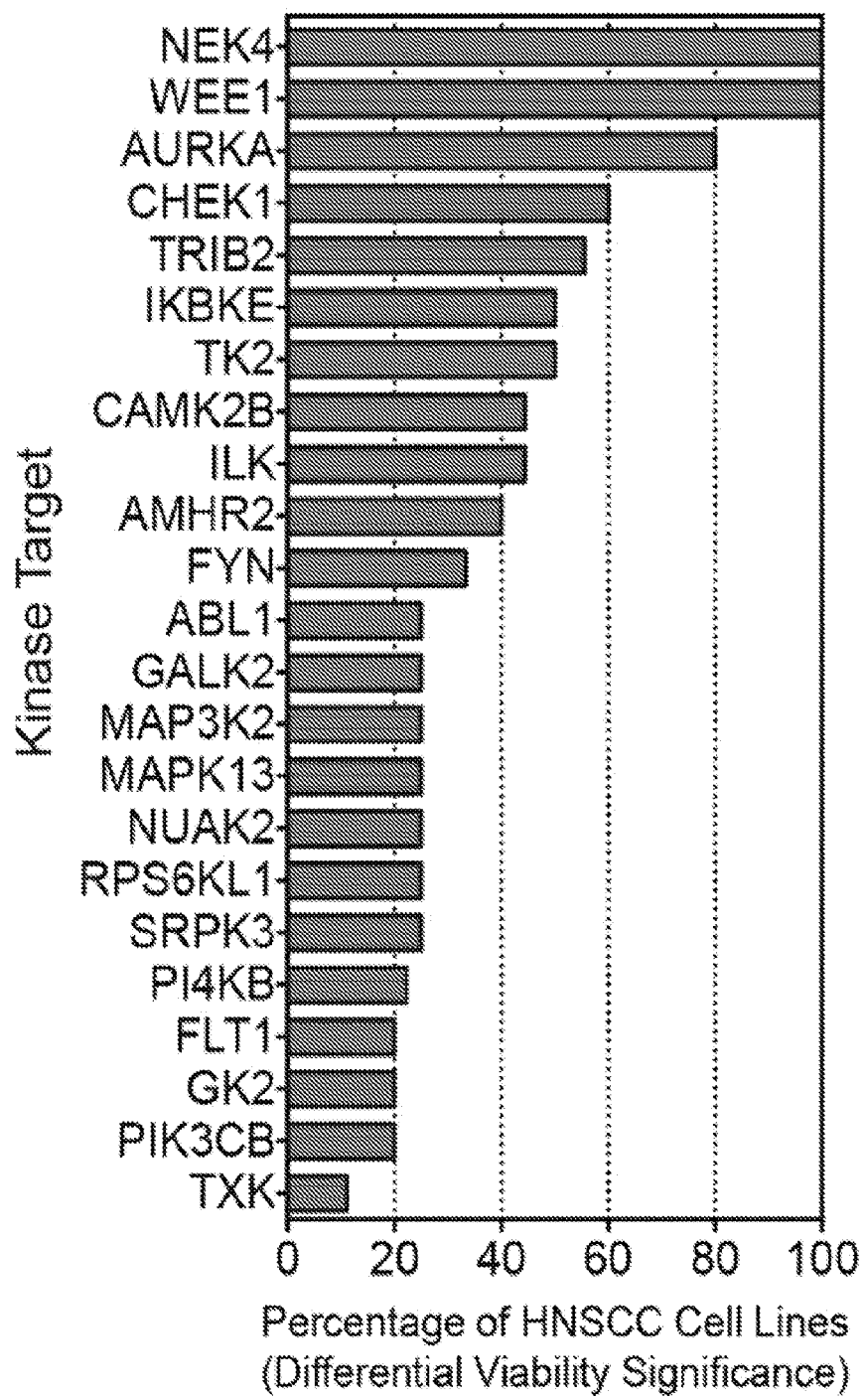
Figure 2K:
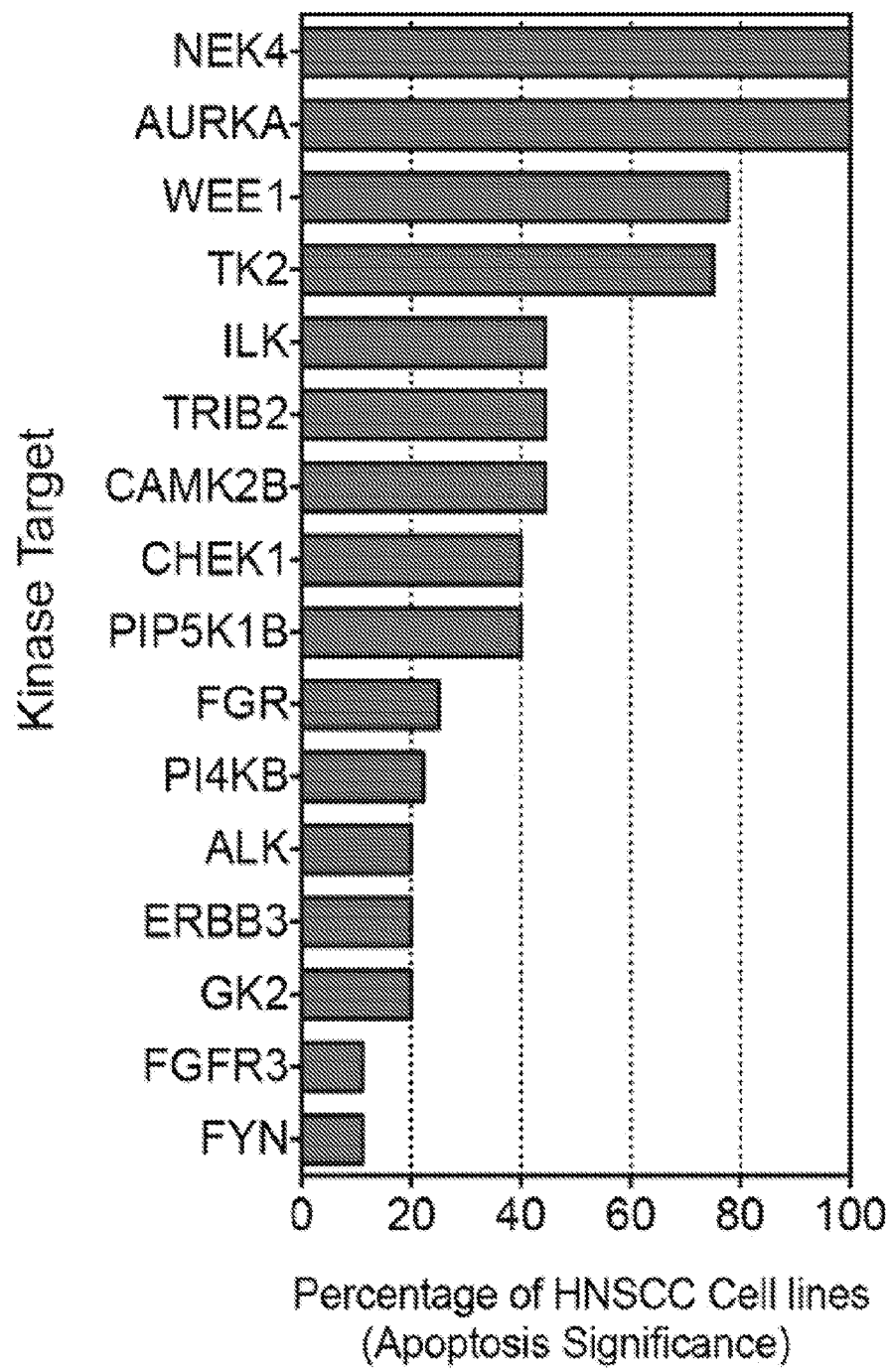
Figure 3A:
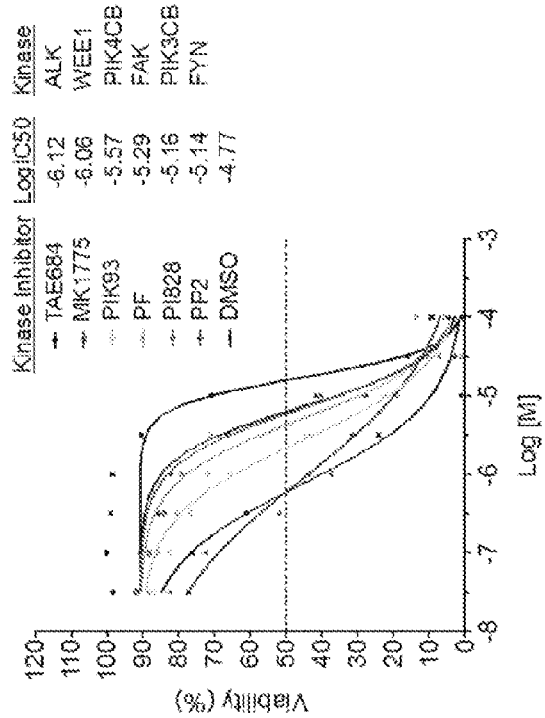
FIG. 3. Chemical inhibition of SRC family kinase (FYN), phosphatidylinositiol kinases (PIK3CB, PIK4CB), focal adhesion kinase (FAK), tyrosine kinase receptor (ALK), and G2/M mitotic kinase (WEE1) impairs viability of autologous pairs of p53 mutant HNSCC cells. Dose-response curves performed with six kinase inhibitors (MK-1775, TAE684, PF-562271, PI828, PIK93, PP2) against kinase targets (WEE1, ALK, PIK3CB, PIK4CB, FYN, FAK; 8-point, mean (N=3), range 100 μM-30 nM, $R^2>0.85$ for all curves. Autologous HNSCC cell pairs (UMSCC-14A (A), UMSCC-14C (B), PCI-15A (C), PCI-15B (D)) derived from primary and recurrent/metastatic site from the same patient.
Figure 3B:
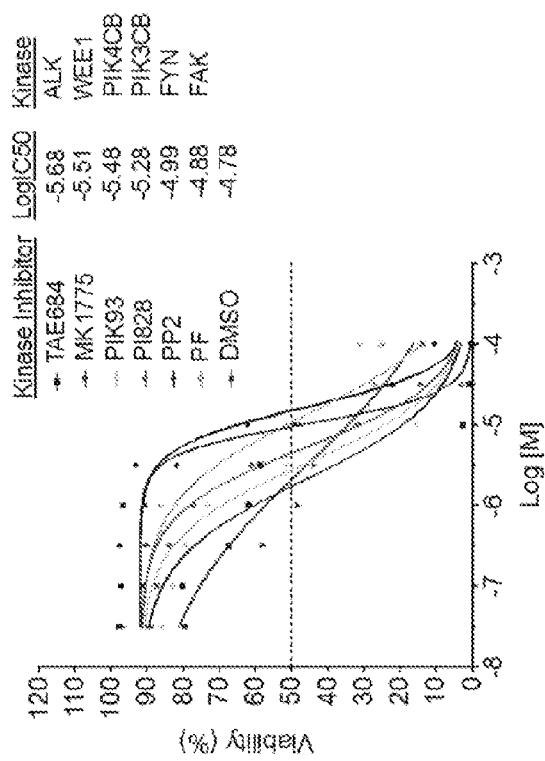
Figure 3C:
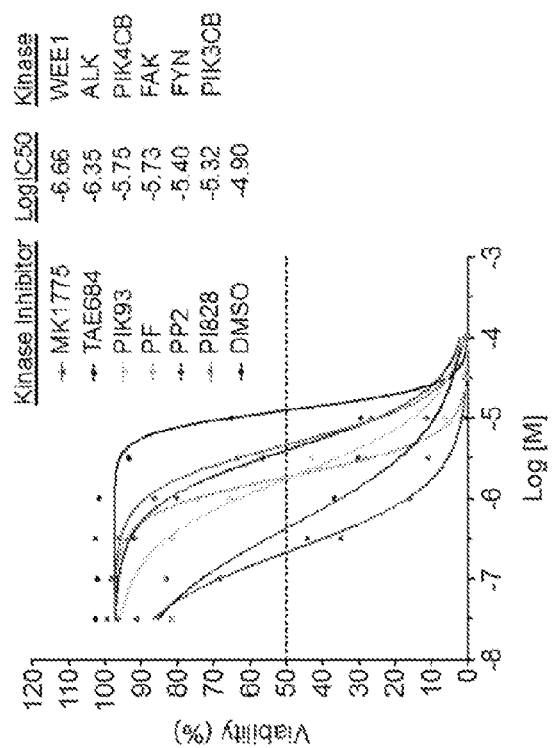
Figure 3D:
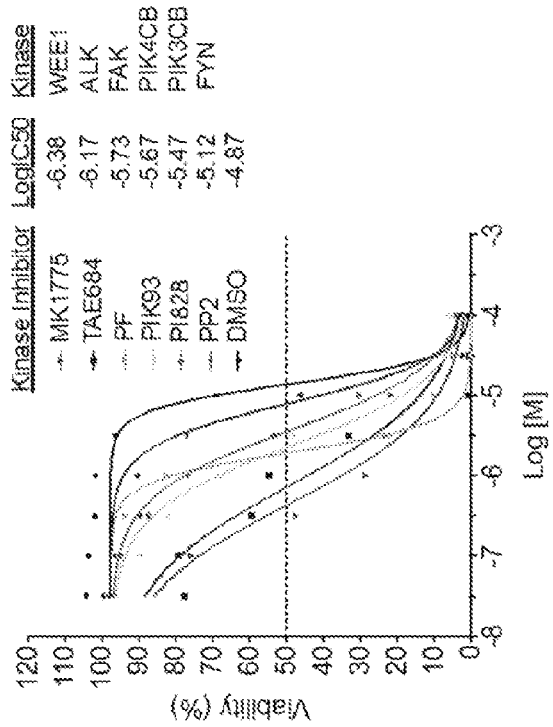

RNAi mediated knockdown of kinases that regulate the G2/M transition, NEK4, WEE1, AURKA, and CHK1, as well as FYN and CAM2 KB significantly impaired viability in three or more of the five cell lines tested (FIG. 2B) while knockdown of the WEE1, NEK4, and AURKA kinases induced the highest levels of apoptosis in all five HNSCC cell lines. Altogether, compiled primary and secondary validation data showed that RNA interference mediated knockdown of WEE1, NEK4, and AURKA kinases significantly reduced viability and increased apoptosis in over 75% of HNSCC cell lines (FIG. 2C).

Figure 11B:
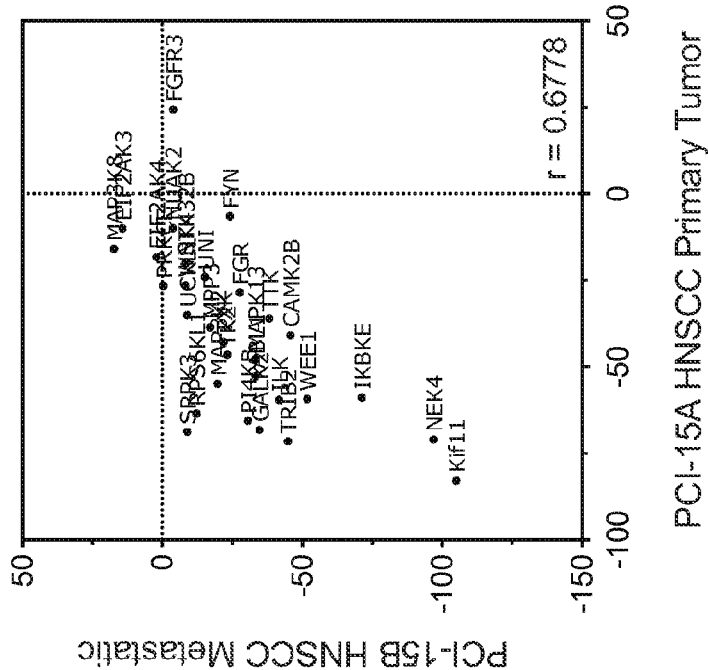
FIG. 11. Correlation plots of autologous HNSCC cell line pairs from primary tumor and recurrent/metastatic site from patients. Correlation plots were generated from differential viability profiles of RNAi mediated knockdown of kinase targets. UM-SCC14A, UM-SCC14C [r=0.7354, P<0.0001] (A); UM-SCC15A, UM-SCC15B [r=0.6778, P<0.0001] (B); and UM-SCC22A, UM-SCC22B [r=0.6424, P<0.0013] (C). Pearson correlation coefficients generated utilizing 30 data points on UMSCC14, UM-SCC15, and 22 data points on UM-SCC22.
Figure 11A:
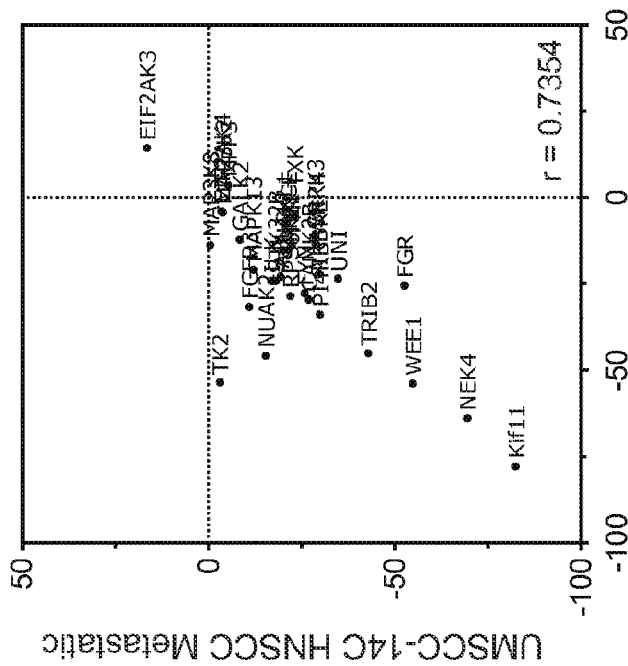
Figure 11C:
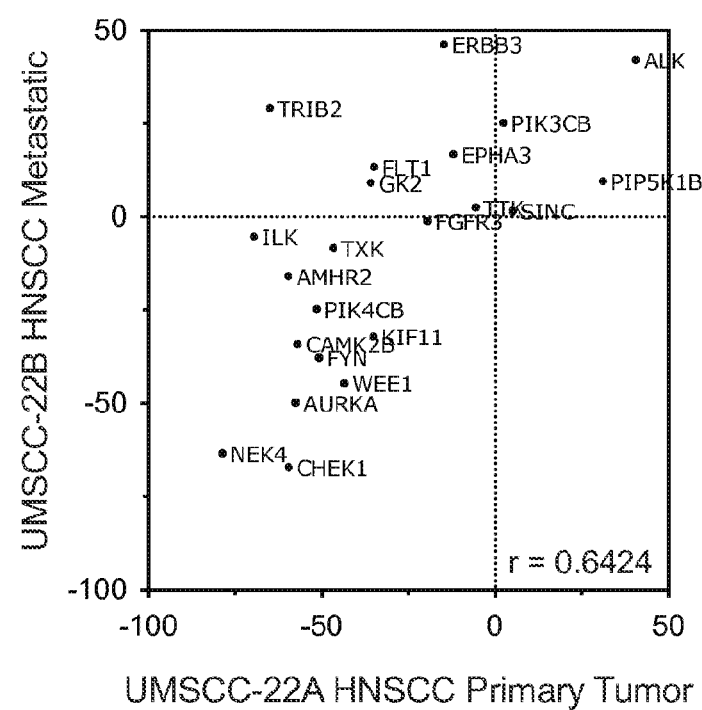

A comparison of functional kinomic profiles between cell line pairs isolated from the same patients showed a high degree of concordance, but with a tendency for the metastatic/recurrent cells to be more resistant to kinase knockdown relative to their primary tumor cell pair (FIG. 2 and FIG. 11). For example, RNAi mediated knockdown of TK2 and TRIB2 was more effective in cells isolated from the primary vs. the recurrent/metastatic lesions (FIG. 2A and FIG. 11). Several kinases, such as WEE1 and NEK4, remained equally effective in both primary and recurrent/metastatic tumors.

Small Molecule Inhibition of Kinases Confirms Role in HNSCC Cell Survival

We further prioritized kinase targets using commercially available small molecule inhibitors. This step not only provides independent chemical confirmation of siRNA results but also provides lead compounds to test in in vivo models. Dose-response curves utilizing kinase inhibitors were performed for WEE1 (MK-1775), ALK (TAE684), PIK4CB (PIK93), FAK (PF-562271), PIK3CB (PI828), and FYN (PP2) (FIG. 3). In agreement with our siRNA knockdown experiments, p53 mutant HNSCC cell lines were sensitive to small molecule inhibitors targeting WEE1, ALK, PIK4CB, and FAK. The WEE1 kinase inhibitor, MK-1775 had the broadest and most significant effect on cell survival in both primary and recurrent/metastasis derived HNSCC cells, with an $IC_{50}$ ranging from 220 nM-3.1 µM (FIG. 3).

Preclinical Validation of WEE1 as a Drug Target for HNSCC In Vitro and In Vivo

Figure 4B:
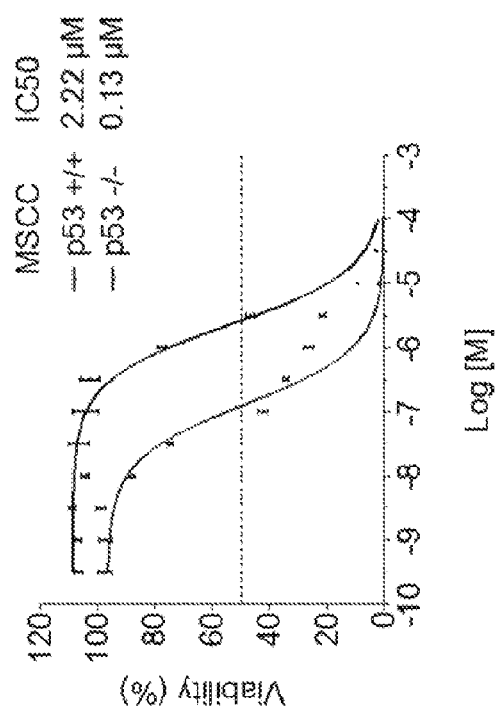
FIG. 4. Drug sensitivity of MSCC and HNSCC cells to chemical inhibition of G2/M mitotic kinases determined by loss-of-function mutational status of p53. A. Differential sensitivity of MSCC p53+/+ and p53−/− cells to WEE1 inhibitor MK-1775 (A) and CHK1/CHK2 inhibitor AZD7762 (B). 12-point dose response curves, mean+/−sem (N=3), range: 100 μM-0.3 nM, R2>0.95 for all curves. C. Differential sensitivity of HNSCC p53+/+ and p53 mutant cell lines to MK-1775.11-point dose response curves, mean+/−sem (N=3), range 100 mM-1 nM, R2>0.86 for all curves. D. Box plots of TP53 mutation status vs. IC50 values following treatment with the dual WEE1/CHK1 inhibitor 681640 based on data from the Genomics of Drug Sensitivity project. Left panel: comparison of TP53 wild type (n=8) and TP53 mutant (n=34) SCC cells. Right panel: comparison of TP53 wild type (n=177) and TP53 mutant (n=322) status across all cell lines excluding SCC lines, representing a diversity of tumor types. E. Bar graph of MK-1775 $IC_{50}$ values for each of the nine cell lines, where * indicates a statistically significant difference in $IC_{50}$ values between p53 wild-type (WT) versus either p53 wild-type, HPV(+) or p53-mutant HNSCC cell cells, ANOVA with the Holm-Sidak posttest; *, P<0.05.
Figure 4A:
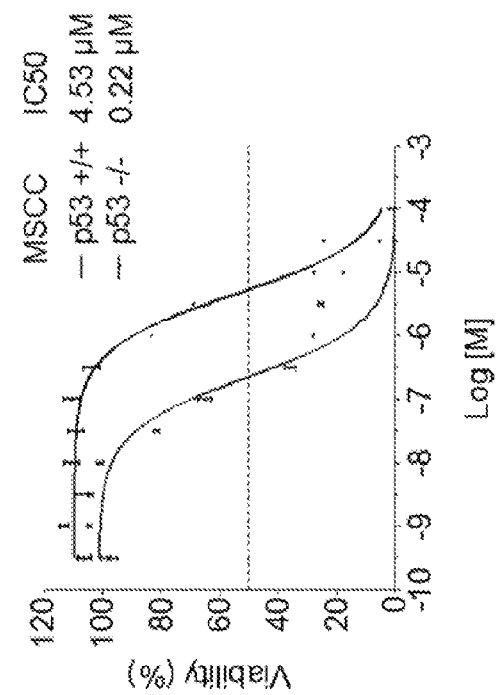

Results from our cross-species comparative analysis of kinome screens, validation assays, and small molecule inhibitor studies nominated WEE1, a G2/M regulator, as a promising target against p53 mutant HNSCC. To further explore the sensitivity of p53 deficient cells to WEE1 inhibition, we performed dose-response curves with MK-1775 in pairs of p53 wild type and p53 mutant/deficient SCC cells. The $IC_{50}$ for MK-1775 was 20-fold lower in p53−/− MSCC cells compared to p53 wild type cells (0.22 µM vs. 4.5 µM) (FIG. 4A). The $IC_{50}$ for MK-1775 in p53 mutant PCI-15A and PCI-15B HNSCC cells (0.14-0.17 µM) and p53 wild type UMSCC-17A cells (4.5 µM) showed a similar differential sensitivity to MK-1775 as the mouse SCC cells, while p53 mutant UMSCC-14A and UMSCC-14C cells and p53 wild type UMSCC-47 cells showed intermediate $IC_{50}$ values of 0.58-1.10 µM (FIG. 4B).

As WEE1 regulates mitotic entry, this suggests p53 deficient cells are sensitive to deregulation of the G2/M transition. CHK1, a kinase required for the DNA damage induced G2/M checkpoint, and AURKA, a kinase involved in spindle assembly during mitosis, were also identified as putative survival kinases (FIG. 2). Consistent with the WEE1 inhibitor results, p53 deficient MSCC cells were also more sensitive to the CHK1 inhibitor, AZD7762 than p53 wild type cells ($IC_{50}$ 0.13 µM vs. 2.2 µM) (FIG. 4A).

Figure 4C:
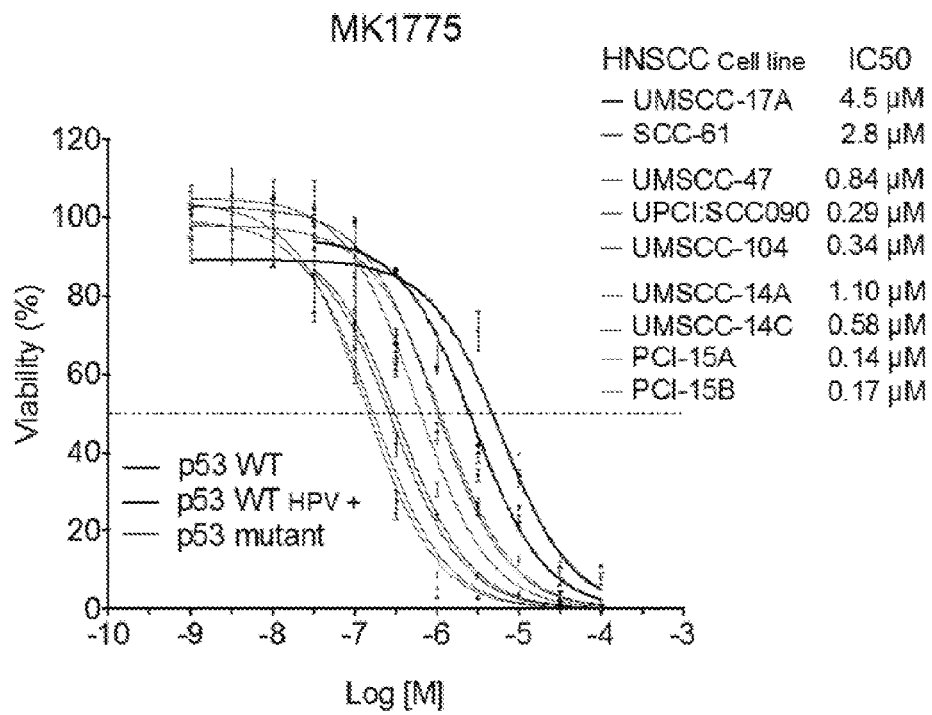

Data from the Genomics of Drug Sensitivity project contains dose-response measurements on 820 genomically characterized cancer cell lines treated with 138 different compounds (32). One compound in this collection, labeled 681640, is a dual WEE1/CHK1 inhibitor (33). We used mutational profiling data from the Sanger Cancer Cell Line Project to classify cell lines based on p53 mutational status and tested for correlation with sensitivity to 681640 (34). Examination of the 42 cells that were derived from squamous cell carcinomas of the head and neck (19), oesophagus (11), lung (5), cervix (3), vulva (3), and skin (1), showed that, despite a broad range of sensitivities in both wild-type and mutant groups, on average p53 mutant SCC cells had increased sensitivity to 681640 compared to p53 wild type cells (median $IC_{50}$: 5.34 µM vs. 29.23 µM, P=0.005) (FIG. 4C). However, the correlation between p53 status and sensitivity to 681640 was not observed in the overall collection of 499 cell lines, which excluded the 42 SCC cell lines and represents a broader variety of tumor types. In fact, the trend between p53 mutant status and 681640 sensitivity was reversed (median $IC_{50}$: 12.83 µM vs. 7.75 µM P=1.348×10$^{-5}$) (FIG. 4C). This analysis emphasizes the importance of validating candidate synthetic lethal interactions or drug sensitivities in specific tumor contexts and it indicates that other factors besides p53 mutational status affect sensitivity to 681640.

Figures 5A, 5B, 5C:
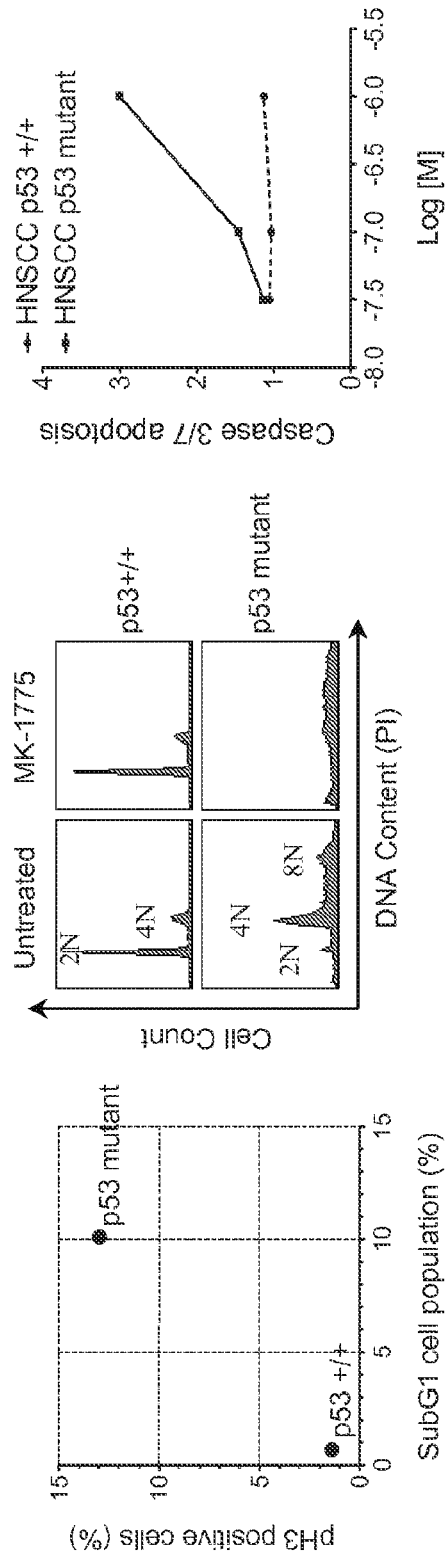
FIG. 5. MK-1775 induces mitotic entry, polyploidy, and apoptosis in HNSCC p53 mutant cells. A. Flow cytometric analysis of HNSCC p53+/+(UM-SCC17A) and p53 mutant (PCI-15B) cells showing % mitotic cells at 8 hours post MK-1775 treatment (y-axis) vs. % cell death at 24 hours (x-axis) normalized to untreated cells. B. Cell cycle profiles at 24 hours post MK-1775 treatment demonstrates abrogation of G2 (4N) cell population and generation of polyploidy in p53 mutant cells. C. Caspase 3/7-dependent apoptosis in HNSCC p53+/+ and HNSCC p53 mutant cells over 48 hours at three different concentrations (30 nm, 100 nm, 1 μM) of MK-1775 (x-axis); fold change AUC ratio=AUC [MK-1775]/AUC [Vehicle] (y-axis).

We next used flow cytometric cell cycle analysis to determine the basis for the enhanced sensitivity of p53 mutant SCC cells to WEE1 inhibition. Treatment of cells with MK-1775 led to unscheduled mitotic entry in p53 mutant but not wild type cells as measured by phospho-histone H3 (serine 10) (FIG. 5A). This was accompanied by an increase in subG1 DNA content, a loss of 4N DNA content, and activation of the apoptotic marker, caspase 3/7 (FIGS. 5B and 5C). This indicates that WEE1 inhibition by MK-1775 in p53 mutant SCC cells caused unscheduled mitotic entry leading to mitotic catastrophe and apoptotic cell death.

Figure 6A:
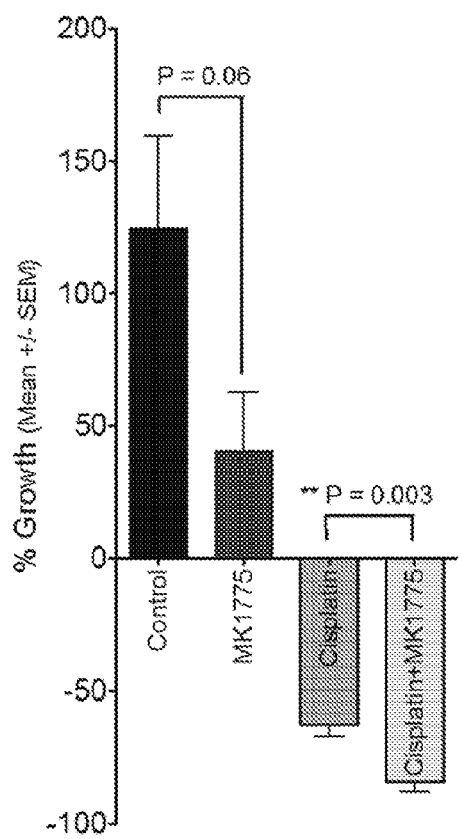
FIG. 6. WEE1 inhibitor MK-1775 potentiates the efficacy of cisplatin in established p53 mutant HNSCC xenografts. A. Percentage growth of PCI-15B xenografts in mice treated with MK-1775 and/or cisplatin. Y-axis represents percentage change (mean+/−SEM) in tumor volume over the course of a 4 week protocol for each group; n=7 per group; unpaired t-tests; control vs. MK1775, P=0.06; cisplatin vs. cisplatin plus MK1775, **P=0.003. B. Bioluminescence images of a representative tumor-bearing mouse from each group at start (Day 1) and end of protocol (Day 28). C. Immunoblot of xenograft tumor lysates from two vehicle and two MK-1775 treated mice with specific antibodies to kinase substrates WEE1, pCdc2, Cdc2, p-Wee1, Wee1, and β-actin loading control. D. Bar graph of relative protein levels of immunoblot analysis of WEE1, CDC2, p-CDC2, mean+SD; normalized values for vehicle versus MK1775 were compared via the unpaired t test, P<0.05 as significant; n=2; WEE1, ns; p=WEE1; *, P=0.02 (one tail); CDC2, ns; p-CDC2; *, P=0.04 (one tail).
Figure 6B:
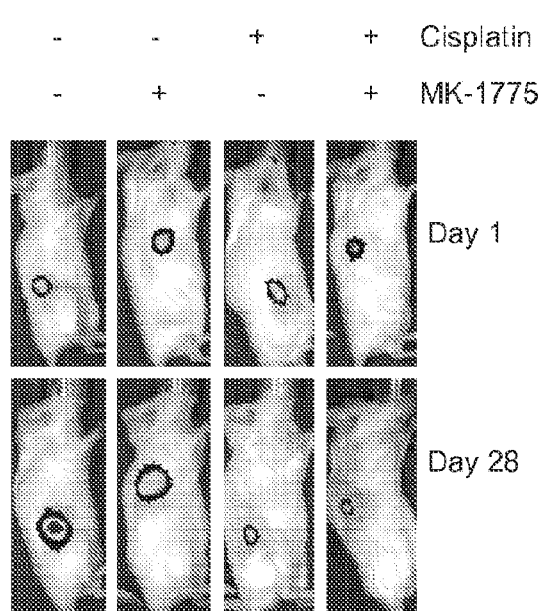
Figure 6C:
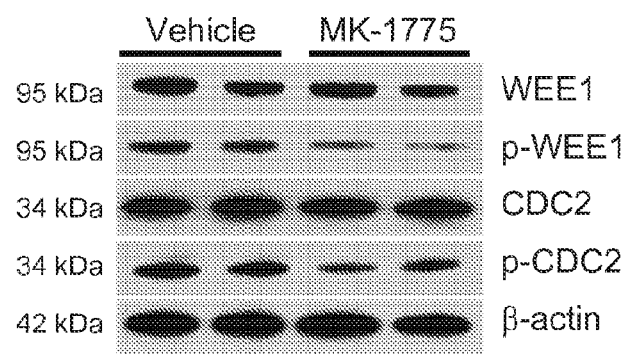
Figure 6D:
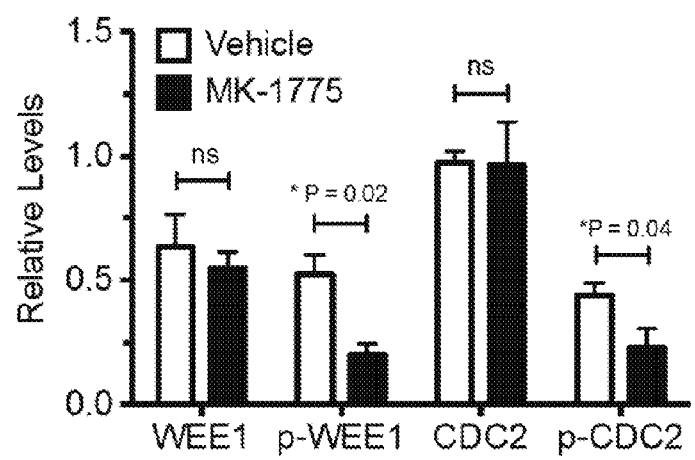
Figure 12:
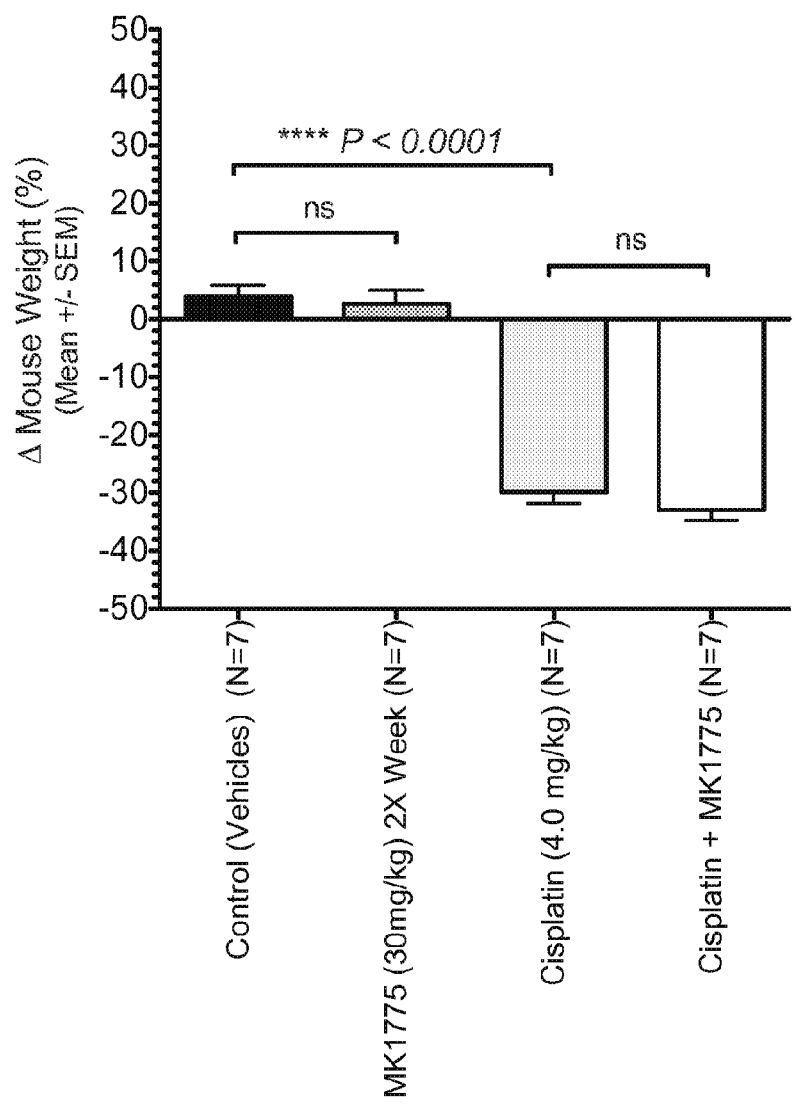
FIG. 12. Body weight of MK-1775 treated mice. Bar graph of percentage change (Mean+/−SEM) in body weight for all treatment groups; unpaired t-tests: control vs. MK-1775, non-significant (ns); cisplatin vs. cisplatin plus MK-1775, ns; control vs. cisplatin, ****P<0.0001.

To determine if WEE1 inhibition was effective against p53 mutant HNSCC in a preclinical tumor model, we performed a four arm double-blind study on PCI-15B xenograft bearing mice. When tumors reached a palpable mass of >50 mm³, mice were randomized into four treatment arms and treated with vehicle, MK-1775, cisplatin, or cisplatin plus MK-1775. Cisplatin is the standard chemotherapeutic agent for HNSCC and cisplatin plus MK-1775 was used to determine if inhibition of WEE1 would synergize with DNA damaging therapy, as p53 mutant tumor cells would be expected to depend on G2/M arrest after DNA damaging treatment to repair DNA. Twice weekly oral gavage of MK-1775 inhibited growth of HNSCC tumors by 66% over the 4-week protocol as compared to vehicle (FIGS. 6A and 6B; P=0.06). Cisplatin alone led to partial tumor regression, but also caused significant weight loss (FIG. 12). However, MK-1775 given 24 hours after cisplatin therapy further augmented tumor regression (60% reduction with cisplatin alone vs. 80% reduction with cisplatin plus MK-1775, P=0.003). Tumor lysates from MK-1775 treated mice probed with WEE1 and CDC2 antibodies showed reduced phosphorylation of WEE1 and its substrate CDC2 indicating that oral administration of MK-1775 effectively blocked WEE1 kinase activity in tumors (FIG. 6C).

Discussion

One of the most significant clinical challenges in the management of HNSCC patients is recurrent disease. In addition to being resistant to radio or chemotherapy, these tumors can present with distant metastases, leaving palliative care as the only option. Here we applied a functional kinomic approach to identify new candidate therapeutic targets for aggressive p53 mutant tumors. To prioritize targets we also screened murine SCC cells, which are defective in the p53 response and have a high propensity to metastasize. We focused on kinase targets that were effective in both species and in more aggressive p53 mutant cells. Retesting of these prioritized targets with independent siRNAs using both viability and apoptosis endpoints pinpointed those that were effective in most or all cells tested, as well as those that were cell line or condition specific.

Comparing siRNA kinome screening results from cells derived from primary and recurrent/metastatic lesions revealed a high degree of concordance, implying that tumor cells isolated at different times or locations from the same patient share common vulnerabilities. In addition, recurrent/metastatic cell lines tended to be less responsive to kinase knockdown relative to cells from the primary lesion, suggesting development of resistance to target knockdown induced cell death. Altogether, these findings indicate this functional kinomic platform can reliably identify profiles of essential survival kinases specific to individual patients.

Figure 4D:
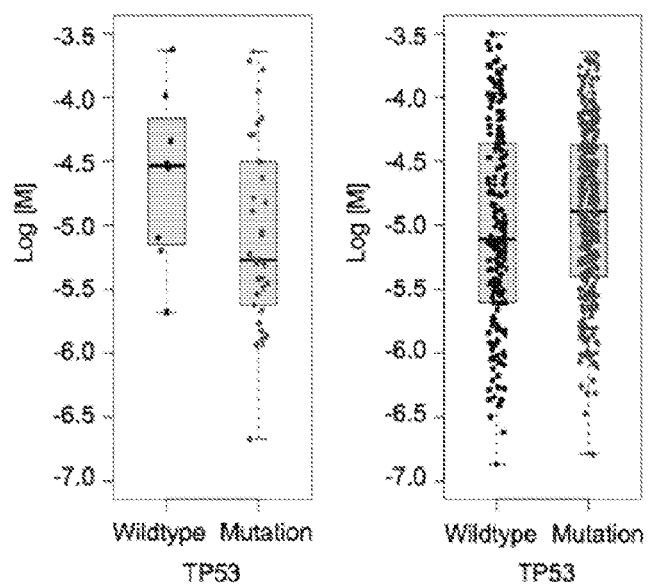
Figure 4E:
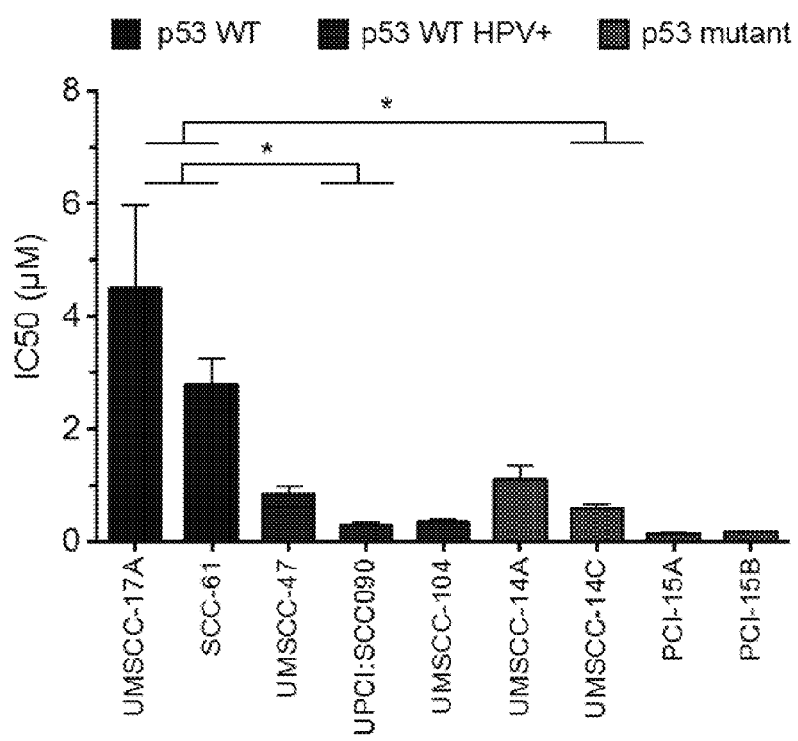

To further validate candidate therapeutic targets we tested several small molecule kinase inhibitors as a confirmatory step to support the RNAi results as well as to identify those inhibitors that might be effective for testing in vivo. Overall, this strategy identified the WEE1 kinase for further validation in vivo as RNAi mediated knockdown of WEE1 led to a significant reduction in cell viability and a concomitant increase in apoptosis in all nine HNSCC cell lines tested. Moreover, p53 deficient MSCC and HNSCC cells were highly sensitive to the specific WEE1 inhibitor MK-1775 relative to p53 WT cells, a finding that has been observed in other settings (Hirai, H. et al., Mol Cancer Ther 2009; 8:2992-3000; Bridges, K A et al., Clin Cancer Res 2011; 17:5638-48; and Rajeshkumar, N V et al., Clin Cancer Res 2011; 17:2799-806). Further more, the HPV+p53 wild-type cell lines were more sensitive to MK-1775 than the p53 wild-type cells, consistent with the idea than functional loss of p53, either by E6 viral component of HPV or by somatic mutation is associated with greater sensitivity to the WEE1 inhibitor, MK1775 (FIG. 4D). Mechanistically, WEE1 inhibition in p53 mutant cells, but not WT cells, led to unscheduled mitotic entry, mitotic catastrophe, and apoptosis, consistent with previous reports (Aarts, A. et al., Cancer Discov 2012; 2:524-39; and De Witt Hamer, P C et al., Clin Cancer Res 2011; 17:4200-7). The G2 checkpoint kinase CHK1 was also a top candidate from our screen and p53 deficient SCC cells showed an increased sensitivity to both a CHK1 and a dual WEE1/CHK1 inhibitor. Collectively this suggests p53 deficient SCC cells may be particularly vulnerable to deregulation of the G2/M transition.

As preclinical validation, we demonstrated that oral administration of MK-1775 inhibited the growth of p53 mutant HNSCC xenografts, and also cooperated with cisplatin to induce tumor regression. Our comparably conservative MK-1775 dosing regiment of two times per week, 24 hours pre- and post-cisplatin treatment was performed in the context of limiting potential toxicities from cisplatin treatment. This regime was well-tolerated, suggesting that higher doses of the MK-1775 inhibitor would also be well-tolerated and high efficacy could be obtained either as a single-agent or in combination with genotoxic treatment.

Currently, cisplatin chemotherapy for the treatment of HNSCC is given either in the neoadjuvant setting or concurrently with radiotherapy. Unfortunately, the associated toxicities of combining cisplatin with other chemotherapeutic agents or the three potentially toxic cisplatin doses of 100 mg/m2 administered during radiation treatment can limit the clinical applicability of these regimens. Thus, the degree by which MK-1775 enhances response to cisplating would not only increase the effectiveness of existing thereapy, but would open the possibility of reducing cisplatin dosing to minimize side effects and broaden patient candidacy to these regimens.

MK-1775 has been shown to sensitize other p53 mutant tumors to DNA damaging agents (Hirai, H. et al., Mol Cancer Ther 2009; 8:2992-3000; Bridges, K A et al., Clin Cancer Res 2011; 17:5638-48; and Rajeshkumar, N V et al., Clin Cancer Res 2011; 17:2799-806). Molecular analysis of HNSCC tumor lysates showed reduced phosphorylation of the WEE1 substrate CDC2, indicating that MK-1775 inhibited its intended target. We previously found amplification of 11q13.1 in metastatic HNSCC tumor cells with corresponding over-expression of cyclin B, the activating subunit of CDC2 (Xu, C. et al., Mol Cancer 2010; 9:143), which could exacerbate the sensitivity of HNSCC cells to WEE1 inhibition.

In addition to WEE1 and CHK1, siRNAs to other mitotic kinases including AURKA and NEK4 reduced viability and increased apoptosis in the majority of HNSCC cells including those derived from recurrent/metastatic lesions suggesting potential as therapeutic targets. AURKA and CHK1 are being pursued as drug targets (Dar, A A et al., Mol Cancer Ther 2010; 9:268-78; Katayama, H. et al., Biochim Biophs Acta 2010; 1799:829-39; and Ma, C X et al., Trends Mol Med 2011; 17:88-96), while NEK4 a member of the NIMA family of kinases modulates sensitivity to microtubule poisons and DNA damage (Doles, J. et al., Cancer Res 2010; 70:1033-41; Moniz, L. et al., Cell Div 2011; 6:18; and Nguyen, C L et al., Mol Cell Biol 2012; 32:3963-77).

siRNAs to several Src family kinases (SFKs) or related signaling proteins (FYN, TXK, CAM2 KB) also reduced viability in one or more HNSCC cell lines and were prioritized as candidates in the cross species comparisons. FYN is a SFK that is involved in many pro-oncogenic process such as cell proliferation, integrin-mediated and PI3K signaling, while TXK is a tyrosine kinase that is activated by the SRC family kinase LYN (Xi, S. et al., J Biol Chem 2003; 278:31574-83; Debnath, J. et al., Mol Cell Biol 1999; 19:1498-507; and Mano, H. et al., FASEB J 1996; 10:637-42). SFKs are activated by mitogenic signals to induce HNSCC cell proliferation and LYN mediates cell motility and tumor growth in head and neck cancer (Mano, H. et al., FASEB J 1996; 10:637-42; and Wheeler, S E et al., Clin Cancer Res 2012; 18:2850-60). Furthermore, SRC/FAK signaling correlates strongly with phenotypes associated with tumor progression such as invasion and metastasis (Wheeler, S E et al., Clin Cancer Res 2012; 18:2850-60; and Zhang, Q., et al. Cancer Res 2004; 64:6166-73) and FAK itself is amplified in HNSCC (Agochiya, M. et al., Oncogene 1999; 18:5646-53), providing further support for targeting the SFK pathway in more aggressive subtypes of HNSCC (Egloff, A M et al., Semin Oncol 2008; 35:286-97; and Stabile, L P et al., Clin Cancer Res 2013; 19:380-92).

In summary, our cross-species functional kinomic approach using autologous pairs of primary and recurrent/metastatic p53 mutant HNSCC lines, coupled with isogenic mouse SCC cells with defined mutations along the p53 pathway has identified several survival kinases as candidate therapeutic targets for aggressive HNSCC. These kinases regulate a range of cellular processes such as phosphatidylinositol, focal adhesion, and Src signaling pathways, and the G2/M cell cycle transition, suggesting functional targets for therapeutic intervention. Discovery and development of multiple targets may prove to be a useful strategy, as tumors frequently develop resistance to single agents and targeting multiple vulnerabilities simultaneously may be a required to achieve long term remission.

Our preclinical data on WEE1 illustrates not only the vulnerabilities of p53 mutant HNSCC cells to deregulation of G2/M transition, but also supports the initiation of clinical trials with MK-1775 or other G2/M checkpoint inhibitors for HNSCC, particularly in combination with cisplatin. More generally, this study illustrates the utility of integrating functional genomic approaches with more traditional descriptive genomic and molecular profiles to identify therapeutic targets in cancer.

Example 2

Validation of Therapeutic Drug Targets for Tumor Suppressor Mutant Cancers in Human Patients To confirm the kinases identified in Example 1 as therapeutic drug targets in human cancers, we performed large scale siRNA screens, using primary tumor cell cultures obtained from patients with a mutation in a tumor suppressor gene. These studies validated kinases identified in Example 1 as therapeutic candidates in primary human tumors. Certain screens were performed using siRNAs to 6,650 genes considered druggable, i.e., the "druggable genome." One screen was performed using a custom designed siRNA library (1302 genes) that included the human kinome (713 genes), DNA damage and repair genes (318 genes), and a Kemp Pancreatic Oncolibrary that includes apoptotic and autophagic genes (96 genes), pancreatic-specific biomarkers (81 genes) (Harsha et al., 2009), pancreatic-specific extracellular/membrane associated genes from serial analysis of gene expression (44 genes) (Jones et al., 2008), pancreatic cancer pathway controls (44 genes), and chromatin-modifying enzymes (6 genes).

We performed a large scale siRNA screen, using 6,659 siRNAs, on a primary tumor cell culture derived from a patient with head and neck squamous cell carcinoma. This patient had a mutation in p53 (P278S). Among the 38 kinases identified in the HNSCC cell line screens, nine (WEE1, CHEK1, GK2, PIP5K1B, EPHA2, RPS6KL1, MPP3, EPHA3, AURKA) were identified as "hits" in the primary culture as well, since inhibition of these genes with siRNAs caused growth arrest of primary cultures of cells obtained from this p53 mutant head and neck squamous cell carcinoma tumor. This further validates the evidence for these nine genes being therapeutic targets in human cancers.

We also performed a large scale siRNA screen, using 6,659 siRNAs, on a primary tumor cell culture derived from a patient with pancreatic cancer. This patient had mutations in both KRAS and p53. The following kinases identified in the HNSCC cell line screens, WEE1, CHEK1, CAMK2B, and GK2, were also identified as "hits" in this primary culture, since inhibition of these genes with siRNAs caused growth arrest of primary cultures of cells from KRAS and p53 mutant pancreatic cancer. This further validates these genes as therapeutic targets.

We also performed a larger scale siRNA screen, using 1,302 siRNAs, on a set of seven KRAS mutant pancreatic cancer cell lines and one KRAS WT normal pancreatic ductal epithelial cell line. siRNAs to the following kinases were preferentially lethal to KRAS mutant pancreatic cancer cells as compared to normal cells: FGFR3, NUAK2, ABL1, NEK4, AURKA, WEE1, CHEK1. This further validates these genes as therapeutic targets, since inhibition of these genes with siRNAs caused growth arrest on primary cultures cells from KRAS mutant pancreatic cancer.

These studies demonstrated that therapeutic targets identified in Example 1 are also targets in primary cell cultures of cells obtained from human cancer patients.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

We claim:

1. A method for treating a pancreatic cancer in a subject in need thereof, wherein the pancreatic cancer comprises a mutation in a Kras gene, the method comprising providing to the subject an inhibitor of NUAK2.

2. The method of claim 1, wherein the inhibitor inhibits expression of NUAK2.

3. The method of claim 1, wherein the inhibitor inhibits an activity of NUAK2.

4. The method of claim 1, further comprising providing to the subject cisplatin.

5. The method of claim 1, wherein the pancreatic cancer is a primary tumor.

6. The method of claim 1, wherein the method comprises determining whether the cancer comprises the mutation in the Kras gene before providing the inhibitor to the subject.

7. The method of claim 1, wherein the method comprises determining a level of expression or activity of NUAK2 or the gene encoding NUAK2 in cancer cells obtained from the subject, before providing the inhibitor of NUAK2 to the subject.

8. The method of claim 1, wherein the inhibitor comprises a polynucleotide that binds a NUAK2 gene or mRNA.

9. A method for inhibiting the growth and/or proliferation of pancreatic cancer cells comprising a mutation in a Kras gene, comprising contacting the cells with an inhibitor of NUAK2.

10. The method of claim 9, wherein the inhibitor comprises a polynucleotide that binds a NUAK2 gene or mRNA.

* * * * *

UNITED STATES PATENT AND TRADEMARK OFFICE
CERTIFICATE OF CORRECTION

PATENT NO. : 10,676,746 B2
APPLICATION NO. : 15/038342
DATED : June 9, 2020
INVENTOR(S) : Christopher Kemp et al.

It is certified that error appears in the above-identified patent and that said Letters Patent is hereby corrected as shown below:

In the Specification

At Column 1, Line number 14:
"This invention was made with government support under CAI 76303 awarded by the National Institutes of Health. The government has certain rights in the invention."
Should read:
--This invention was made with government support under CA176303 and CA217883 awarded by the National Institutes of Health. The government has certain rights in this invention.--

Signed and Sealed this
Twenty-eighth Day of July, 2020

Andrei Iancu
*Director of the United States Patent and Trademark Office*

SEQUENCE LISTING

<160> NUMBER OF SEQ ID NOS: 141

<210> SEQ ID NO 1
<211> LENGTH: 21
<212> TYPE: DNA
<213> ORGANISM: Homo sapiens

<400> SEQUENCE: 1
ccagtggaga taacactcta a                                              21

<210> SEQ ID NO 2
<211> LENGTH: 21
<212> TYPE: DNA
<213> ORGANISM: Homo sapiens

<400> SEQUENCE: 2
cccggaagca ggagatcatt a                                              21

<210> SEQ ID NO 3
<211> LENGTH: 21
<212> TYPE: DNA
<213> ORGANISM: Homo sapiens

<400> SEQUENCE: 3
cgcgcggcag gtcattagta a                                              21

<210> SEQ ID NO 4
<211> LENGTH: 21
<212> TYPE: DNA
<213> ORGANISM: Homo sapiens

<400> SEQUENCE: 4
caaggttaag tctttcgaga a                                              21

<210> SEQ ID NO 5
<211> LENGTH: 21
<212> TYPE: DNA
<213> ORGANISM: Homo sapiens

<400> SEQUENCE: 5
aaggaagtgg tactgctgga c                                              21

<210> SEQ ID NO 6
<211> LENGTH: 21
<212> TYPE: DNA
<213> ORGANISM: Homo sapiens

<400> SEQUENCE: 6
ctgaaattac gggtacctga a                                              21

<210> SEQ ID NO 7
<211> LENGTH: 21
<212> TYPE: DNA
<213> ORGANISM: Homo sapiens

<400> SEQUENCE: 7
cagaccttgt ctagttattt a                                              21

<210> SEQ ID NO 8
<211> LENGTH: 21
<212> TYPE: DNA
<213> ORGANISM: Homo sapiens

```
<400> SEQUENCE: 8
aagacatgtg gtgtatataa a                                              21

<210> SEQ ID NO 9
<211> LENGTH: 21
<212> TYPE: DNA
<213> ORGANISM: Homo sapiens

<400> SEQUENCE: 9
tgcgcgagtg ctccagttta a                                              21

<210> SEQ ID NO 10
<211> LENGTH: 21
<212> TYPE: DNA
<213> ORGANISM: Homo sapiens

<400> SEQUENCE: 10
cagaagcatc cagcagattc a                                              21

<210> SEQ ID NO 11
<211> LENGTH: 21
<212> TYPE: DNA
<213> ORGANISM: Homo sapiens

<400> SEQUENCE: 11
aaggaagagc agggacttca a                                              21

<210> SEQ ID NO 12
<211> LENGTH: 21
<212> TYPE: DNA
<213> ORGANISM: Homo sapiens

<400> SEQUENCE: 12
taggagcgaa gagttcaatt a                                              21

<210> SEQ ID NO 13
<211> LENGTH: 21
<212> TYPE: DNA
<213> ORGANISM: Homo sapiens

<400> SEQUENCE: 13
tgccatgttt gctctaaatt a                                              21

<210> SEQ ID NO 14
<211> LENGTH: 21
<212> TYPE: DNA
<213> ORGANISM: Homo sapiens

<400> SEQUENCE: 14
tagggatgct ctaacgaatt a                                              21

<210> SEQ ID NO 15
<211> LENGTH: 21
<212> TYPE: DNA
<213> ORGANISM: Homo sapiens

<400> SEQUENCE: 15
ttcgctatta tgaaaggcaa a                                              21

<210> SEQ ID NO 16
<211> LENGTH: 21
<212> TYPE: DNA
<213> ORGANISM: Homo sapiens
```

```
<400> SEQUENCE: 16
taggaggtat atgcagtatt t                                              21

<210> SEQ ID NO 17
<211> LENGTH: 21
<212> TYPE: DNA
<213> ORGANISM: Homo sapiens

<400> SEQUENCE: 17
cagcaagatc gtgatcgtca t                                              21

<210> SEQ ID NO 18
<211> LENGTH: 21
<212> TYPE: DNA
<213> ORGANISM: Homo sapiens

<400> SEQUENCE: 18
tcggctgata gtggcatgat t                                              21

<210> SEQ ID NO 19
<211> LENGTH: 21
<212> TYPE: DNA
<213> ORGANISM: Homo sapiens

<400> SEQUENCE: 19
tacaatgacg ttaagtctta a                                              21

<210> SEQ ID NO 20
<211> LENGTH: 21
<212> TYPE: DNA
<213> ORGANISM: Homo sapiens

<400> SEQUENCE: 20
gaggatgaag gctcagctca a                                              21

<210> SEQ ID NO 21
<211> LENGTH: 21
<212> TYPE: DNA
<213> ORGANISM: Homo sapiens

<400> SEQUENCE: 21
cggctcccta tttatacaat a                                              21

<210> SEQ ID NO 22
<211> LENGTH: 21
<212> TYPE: DNA
<213> ORGANISM: Homo sapiens

<400> SEQUENCE: 22
atgccagaag tggactatgt a                                              21

<210> SEQ ID NO 23
<211> LENGTH: 21
<212> TYPE: DNA
<213> ORGANISM: Homo sapiens

<400> SEQUENCE: 23
cacgtggact ctagtatgta a                                              21

<210> SEQ ID NO 24
<211> LENGTH: 21
<212> TYPE: DNA
<213> ORGANISM: Homo sapiens
```

-continued

```
<400> SEQUENCE: 24
cagcaatacc ttggatgatt a                                              21

<210> SEQ ID NO 25
<211> LENGTH: 21
<212> TYPE: DNA
<213> ORGANISM: Homo sapiens

<400> SEQUENCE: 25
cccggtgaca ttctatttcc a                                              21

<210> SEQ ID NO 26
<211> LENGTH: 21
<212> TYPE: DNA
<213> ORGANISM: Homo sapiens

<400> SEQUENCE: 26
tcgcgacgag ttcatcttct a                                              21

<210> SEQ ID NO 27
<211> LENGTH: 21
<212> TYPE: DNA
<213> ORGANISM: Homo sapiens

<400> SEQUENCE: 27
cactggtaaa gcattcagta t                                              21

<210> SEQ ID NO 28
<211> LENGTH: 21
<212> TYPE: DNA
<213> ORGANISM: Homo sapiens

<400> SEQUENCE: 28
cactagtgtc tcagaccaga a                                              21

<210> SEQ ID NO 29
<211> LENGTH: 21
<212> TYPE: DNA
<213> ORGANISM: Homo sapiens

<400> SEQUENCE: 29
aaaggtgaaa agctccgggt c                                              21

<210> SEQ ID NO 30
<211> LENGTH: 21
<212> TYPE: DNA
<213> ORGANISM: Homo sapiens

<400> SEQUENCE: 30
cacgaccatc ctgaacccac a                                              21

<210> SEQ ID NO 31
<211> LENGTH: 21
<212> TYPE: DNA
<213> ORGANISM: Homo sapiens

<400> SEQUENCE: 31
cacaaactgt ataacggttt a                                              21

<210> SEQ ID NO 32
<211> LENGTH: 21
<212> TYPE: DNA
<213> ORGANISM: Homo sapiens
```

```
<400> SEQUENCE: 32
caccgtcaag attacggact a                                              21

<210> SEQ ID NO 33
<211> LENGTH: 21
<212> TYPE: DNA
<213> ORGANISM: Homo sapiens

<400> SEQUENCE: 33
aagcgcctgt tcaccaagat t                                              21

<210> SEQ ID NO 34
<211> LENGTH: 21
<212> TYPE: DNA
<213> ORGANISM: Homo sapiens

<400> SEQUENCE: 34
accctacgtt accgtgctca a                                              21

<210> SEQ ID NO 35
<211> LENGTH: 21
<212> TYPE: DNA
<213> ORGANISM: Homo sapiens

<400> SEQUENCE: 35
ttgattctgt aaataagtaa a                                              21

<210> SEQ ID NO 36
<211> LENGTH: 21
<212> TYPE: DNA
<213> ORGANISM: Homo sapiens

<400> SEQUENCE: 36
gtggcccttt atgactatga a                                              21

<210> SEQ ID NO 37
<211> LENGTH: 21
<212> TYPE: DNA
<213> ORGANISM: Homo sapiens

<400> SEQUENCE: 37
ctggaggaac tccgaaccca a                                              21

<210> SEQ ID NO 38
<211> LENGTH: 21
<212> TYPE: DNA
<213> ORGANISM: Homo sapiens

<400> SEQUENCE: 38
ccgcatcatc gaacggctaa a                                              21

<210> SEQ ID NO 39
<211> LENGTH: 21
<212> TYPE: DNA
<213> ORGANISM: Homo sapiens

<400> SEQUENCE: 39
tagccgtagt gtaatgattg a                                              21

<210> SEQ ID NO 40
<211> LENGTH: 21
<212> TYPE: DNA
<213> ORGANISM: Homo sapiens
```

<400> SEQUENCE: 40
aatgatgtcc gagtcaaatt t                                                   21

<210> SEQ ID NO 41
<211> LENGTH: 21
<212> TYPE: DNA
<213> ORGANISM: Homo sapiens

<400> SEQUENCE: 41
cgggcagtct ctttctgttt a                                                   21

<210> SEQ ID NO 42
<211> LENGTH: 21
<212> TYPE: DNA
<213> ORGANISM: Homo sapiens

<400> SEQUENCE: 42
ccggagtggc atgaagctgt a                                                   21

<210> SEQ ID NO 43
<211> LENGTH: 21
<212> TYPE: DNA
<213> ORGANISM: Homo sapiens

<400> SEQUENCE: 43
cacgttggag atgagctccg a                                                   21

<210> SEQ ID NO 44
<211> LENGTH: 21
<212> TYPE: DNA
<213> ORGANISM: Homo sapiens

<400> SEQUENCE: 44
ctcatctagg gtatatacaa a                                                   21

<210> SEQ ID NO 45
<211> LENGTH: 21
<212> TYPE: DNA
<213> ORGANISM: Homo sapiens

<400> SEQUENCE: 45
tacctaatgg tctctaccta a                                                   21

<210> SEQ ID NO 46
<211> LENGTH: 21
<212> TYPE: DNA
<213> ORGANISM: Homo sapiens

<400> SEQUENCE: 46
cgacatgttc aactactata a                                                   21

<210> SEQ ID NO 47
<211> LENGTH: 21
<212> TYPE: DNA
<213> ORGANISM: Homo sapiens

<400> SEQUENCE: 47
cccgaccatg gtagtgttca a                                                   21

<210> SEQ ID NO 48
<211> LENGTH: 21
<212> TYPE: DNA
<213> ORGANISM: Homo sapiens

```
<400> SEQUENCE: 48
cgcgatgtta gtgaggacta t                                              21

<210> SEQ ID NO 49
<211> LENGTH: 21
<212> TYPE: DNA
<213> ORGANISM: Homo sapiens

<400> SEQUENCE: 49
ctgggacgcg gtgttcaaga a                                              21

<210> SEQ ID NO 50
<211> LENGTH: 21
<212> TYPE: DNA
<213> ORGANISM: Homo sapiens

<400> SEQUENCE: 50
cgggatcgaa tattaactcc a                                              21

<210> SEQ ID NO 51
<211> LENGTH: 21
<212> TYPE: DNA
<213> ORGANISM: Homo sapiens

<400> SEQUENCE: 51
caggttgtcc cacatgtata a                                              21

<210> SEQ ID NO 52
<211> LENGTH: 21
<212> TYPE: DNA
<213> ORGANISM: Homo sapiens

<400> SEQUENCE: 52
tccgacttta tgattatgaa a                                              21

<210> SEQ ID NO 53
<211> LENGTH: 21
<212> TYPE: DNA
<213> ORGANISM: Homo sapiens

<400> SEQUENCE: 53
cagctgggtt tagctacgaa a                                              21

<210> SEQ ID NO 54
<211> LENGTH: 21
<212> TYPE: DNA
<213> ORGANISM: Homo sapiens

<400> SEQUENCE: 54
tacaatgaac acggcacgca a                                              21

<210> SEQ ID NO 55
<211> LENGTH: 21
<212> TYPE: DNA
<213> ORGANISM: Homo sapiens

<400> SEQUENCE: 55
caagacctgc taagagaatt a                                              21

<210> SEQ ID NO 56
<211> LENGTH: 21
<212> TYPE: DNA
<213> ORGANISM: Homo sapiens
```

```
<400> SEQUENCE: 56
cagcttgttg ggcgtttcca a                                         21

<210> SEQ ID NO 57
<211> LENGTH: 21
<212> TYPE: DNA
<213> ORGANISM: Homo sapiens

<400> SEQUENCE: 57
aacttggtga aggtagctga t                                         21

<210> SEQ ID NO 58
<211> LENGTH: 21
<212> TYPE: DNA
<213> ORGANISM: Homo sapiens

<400> SEQUENCE: 58
ccggctcacg cagtacattg a                                         21

<210> SEQ ID NO 59
<211> LENGTH: 21
<212> TYPE: DNA
<213> ORGANISM: Homo sapiens

<400> SEQUENCE: 59
cggcaggtca ttagtaatta t                                         21

<210> SEQ ID NO 60
<211> LENGTH: 21
<212> TYPE: DNA
<213> ORGANISM: Homo sapiens

<400> SEQUENCE: 60
tacacctatg acagcgacat a                                         21

<210> SEQ ID NO 61
<211> LENGTH: 21
<212> TYPE: DNA
<213> ORGANISM: Homo sapiens

<400> SEQUENCE: 61
cagcgccaag taaacagggt a                                         21

<210> SEQ ID NO 62
<211> LENGTH: 21
<212> TYPE: DNA
<213> ORGANISM: Homo sapiens

<400> SEQUENCE: 62
ccgatgttat tagatgttac a                                         21

<210> SEQ ID NO 63
<211> LENGTH: 21
<212> TYPE: DNA
<213> ORGANISM: Homo sapiens

<400> SEQUENCE: 63
cacgtggaac ggcagcacta a                                         21

<210> SEQ ID NO 64
<211> LENGTH: 21
<212> TYPE: DNA
<213> ORGANISM: Homo sapiens
```

```
<400> SEQUENCE: 64
aagaagcagg atgctgatct a                                              21

<210> SEQ ID NO 65
<211> LENGTH: 21
<212> TYPE: DNA
<213> ORGANISM: Homo sapiens

<400> SEQUENCE: 65
atcaatggta cctgcggaca a                                              21

<210> SEQ ID NO 66
<211> LENGTH: 21
<212> TYPE: DNA
<213> ORGANISM: Homo sapiens

<400> SEQUENCE: 66
caagatgaac ttcatctaca a                                              21

<210> SEQ ID NO 67
<211> LENGTH: 21
<212> TYPE: DNA
<213> ORGANISM: Homo sapiens

<400> SEQUENCE: 67
cagcccgagt cccgaggata a                                              21

<210> SEQ ID NO 68
<211> LENGTH: 21
<212> TYPE: DNA
<213> ORGANISM: Homo sapiens

<400> SEQUENCE: 68
cagaatgatg tccgagtcaa a                                              21

<210> SEQ ID NO 69
<211> LENGTH: 21
<212> TYPE: DNA
<213> ORGANISM: Homo sapiens

<400> SEQUENCE: 69
aaggataata gagtagccta a                                              21

<210> SEQ ID NO 70
<211> LENGTH: 21
<212> TYPE: DNA
<213> ORGANISM: Homo sapiens

<400> SEQUENCE: 70
cgggatgagc ctcatccgga a                                              21

<210> SEQ ID NO 71
<211> LENGTH: 21
<212> TYPE: DNA
<213> ORGANISM: Homo sapiens

<400> SEQUENCE: 71
cccgacgaga tcagccagat t                                              21

<210> SEQ ID NO 72
<211> LENGTH: 21
<212> TYPE: DNA
<213> ORGANISM: Homo sapiens
```

```
<400> SEQUENCE: 72
ctgggtctgt gagcagttca a                                              21

<210> SEQ ID NO 73
<211> LENGTH: 21
<212> TYPE: DNA
<213> ORGANISM: Homo sapiens

<400> SEQUENCE: 73
gaccataaga tcctagtgaa a                                              21

<210> SEQ ID NO 74
<211> LENGTH: 21
<212> TYPE: DNA
<213> ORGANISM: Homo sapiens

<400> SEQUENCE: 74
tggcgacatg ttcaactact a                                              21

<210> SEQ ID NO 75
<211> LENGTH: 21
<212> TYPE: DNA
<213> ORGANISM: Homo sapiens

<400> SEQUENCE: 75
cacggaaaca cccgtacctt a                                              21

<210> SEQ ID NO 76
<211> LENGTH: 21
<212> TYPE: DNA
<213> ORGANISM: Homo sapiens

<400> SEQUENCE: 76
ctgggagtgc ctgacatgac a                                              21

<210> SEQ ID NO 77
<211> LENGTH: 21
<212> TYPE: DNA
<213> ORGANISM: Homo sapiens

<400> SEQUENCE: 77
ttgggctgag ttcacgaatt a                                              21

<210> SEQ ID NO 78
<211> LENGTH: 21
<212> TYPE: DNA
<213> ORGANISM: Homo sapiens

<400> SEQUENCE: 78
ccgcgccgac tcgcacaaga a                                              21

<210> SEQ ID NO 79
<211> LENGTH: 21
<212> TYPE: DNA
<213> ORGANISM: Homo sapiens

<400> SEQUENCE: 79
tagagacaag cgggaaggat a                                              21

<210> SEQ ID NO 80
<211> LENGTH: 21
<212> TYPE: DNA
<213> ORGANISM: Homo sapiens
```

```
<400> SEQUENCE: 80
cagaaatagg ttaccggaat t                                            21

<210> SEQ ID NO 81
<211> LENGTH: 21
<212> TYPE: DNA
<213> ORGANISM: Homo sapiens

<400> SEQUENCE: 81
taggtgaatg gcggtcacat a                                            21

<210> SEQ ID NO 82
<211> LENGTH: 21
<212> TYPE: DNA
<213> ORGANISM: Homo sapiens

<400> SEQUENCE: 82
tacaagcaag cgtaccatct a                                            21

<210> SEQ ID NO 83
<211> LENGTH: 21
<212> TYPE: DNA
<213> ORGANISM: Homo sapiens

<400> SEQUENCE: 83
acaattacga atagaattga a                                            21

<210> SEQ ID NO 84
<211> LENGTH: 21
<212> TYPE: DNA
<213> ORGANISM: Homo sapiens

<400> SEQUENCE: 84
caggaggagc cagcaccatt a                                            21

<210> SEQ ID NO 85
<211> LENGTH: 21
<212> TYPE: DNA
<213> ORGANISM: Homo sapiens

<400> SEQUENCE: 85
ctcgaccatc atgaccgact a                                            21

<210> SEQ ID NO 86
<211> LENGTH: 21
<212> TYPE: DNA
<213> ORGANISM: Homo sapiens

<400> SEQUENCE: 86
cagaatgtgc tcattcggga a                                            21

<210> SEQ ID NO 87
<211> LENGTH: 21
<212> TYPE: DNA
<213> ORGANISM: Homo sapiens

<400> SEQUENCE: 87
caccttcggc atcctaatat t                                            21

<210> SEQ ID NO 88
<211> LENGTH: 21
<212> TYPE: DNA
<213> ORGANISM: Homo sapiens
```

```
<400> SEQUENCE: 88
cccggaagca ggagatcatt a                                              21

<210> SEQ ID NO 89
<211> LENGTH: 21
<212> TYPE: DNA
<213> ORGANISM: Homo sapiens

<400> SEQUENCE: 89
ttggaataac tcacagggat a                                              21

<210> SEQ ID NO 90
<211> LENGTH: 21
<212> TYPE: DNA
<213> ORGANISM: Homo sapiens

<400> SEQUENCE: 90
tcggatatga ttgtttctca a                                              21

<210> SEQ ID NO 91
<211> LENGTH: 21
<212> TYPE: DNA
<213> ORGANISM: Homo sapiens

<400> SEQUENCE: 91
accacggtat ctggtcataa a                                              21

<210> SEQ ID NO 92
<211> LENGTH: 21
<212> TYPE: DNA
<213> ORGANISM: Homo sapiens

<400> SEQUENCE: 92
ctgaaattac gggtacctga a                                              21

<210> SEQ ID NO 93
<211> LENGTH: 21
<212> TYPE: DNA
<213> ORGANISM: Homo sapiens

<400> SEQUENCE: 93
tcgccggaag ttgtatggtt a                                              21

<210> SEQ ID NO 94
<211> LENGTH: 21
<212> TYPE: DNA
<213> ORGANISM: Homo sapiens

<400> SEQUENCE: 94
aagacatgtg gtgtatataa a                                              21

<210> SEQ ID NO 95
<211> LENGTH: 21
<212> TYPE: DNA
<213> ORGANISM: Homo sapiens

<400> SEQUENCE: 95
gacgaactga atattgatat a                                              21

<210> SEQ ID NO 96
<211> LENGTH: 21
<212> TYPE: DNA
<213> ORGANISM: Homo sapiens
```

```
<400> SEQUENCE: 96
aaggaagagc agggacttca a                                              21

<210> SEQ ID NO 97
<211> LENGTH: 21
<212> TYPE: DNA
<213> ORGANISM: Homo sapiens

<400> SEQUENCE: 97
ctcatctagg gtatatacaa a                                              21

<210> SEQ ID NO 98
<211> LENGTH: 21
<212> TYPE: DNA
<213> ORGANISM: Homo sapiens

<400> SEQUENCE: 98
tcggctgata gtggcatgat t                                              21

<210> SEQ ID NO 99
<211> LENGTH: 21
<212> TYPE: DNA
<213> ORGANISM: Homo sapiens

<400> SEQUENCE: 99
cccttcgata agattattga a                                              21

<210> SEQ ID NO 100
<211> LENGTH: 21
<212> TYPE: DNA
<213> ORGANISM: Homo sapiens

<400> SEQUENCE: 100
tacactctat tcaaacagca a                                              21

<210> SEQ ID NO 101
<211> LENGTH: 21
<212> TYPE: DNA
<213> ORGANISM: Homo sapiens

<400> SEQUENCE: 101
cacgtggact ctagtatgta a                                              21

<210> SEQ ID NO 102
<211> LENGTH: 21
<212> TYPE: DNA
<213> ORGANISM: Homo sapiens

<400> SEQUENCE: 102
cagcaatacc ttggatgatt a                                              21

<210> SEQ ID NO 103
<211> LENGTH: 21
<212> TYPE: DNA
<213> ORGANISM: Homo sapiens

<400> SEQUENCE: 103
cccggtgaca ttctatttcc a                                              21

<210> SEQ ID NO 104
<211> LENGTH: 21
<212> TYPE: DNA
<213> ORGANISM: Homo sapiens
```

```
<400> SEQUENCE: 104
cactggtaaa gcattcagta t                                              21

<210> SEQ ID NO 105
<211> LENGTH: 21
<212> TYPE: DNA
<213> ORGANISM: Homo sapiens

<400> SEQUENCE: 105
ctcctcggtt ctagggctaa a                                              21

<210> SEQ ID NO 106
<211> LENGTH: 21
<212> TYPE: DNA
<213> ORGANISM: Homo sapiens

<400> SEQUENCE: 106
atggccaata taaaccaggt a                                              21

<210> SEQ ID NO 107
<211> LENGTH: 21
<212> TYPE: DNA
<213> ORGANISM: Homo sapiens

<400> SEQUENCE: 107
tcccagcgca ttcctttgca a                                              21

<210> SEQ ID NO 108
<211> LENGTH: 21
<212> TYPE: DNA
<213> ORGANISM: Homo sapiens

<400> SEQUENCE: 108
cacgaccatc ctgaacccac a                                              21

<210> SEQ ID NO 109
<211> LENGTH: 21
<212> TYPE: DNA
<213> ORGANISM: Homo sapiens

<400> SEQUENCE: 109
aactgaagaa gcagtcgcag t                                              21

<210> SEQ ID NO 110
<211> LENGTH: 21
<212> TYPE: DNA
<213> ORGANISM: Homo sapiens

<400> SEQUENCE: 110
ttggatagtt tcctacgtaa a                                              21

<210> SEQ ID NO 111
<211> LENGTH: 21
<212> TYPE: DNA
<213> ORGANISM: Homo sapiens

<400> SEQUENCE: 111
cttcgtcatg ttgaactata a                                              21

<210> SEQ ID NO 112
<211> LENGTH: 21
<212> TYPE: DNA
<213> ORGANISM: Homo sapiens
```

```
<400> SEQUENCE: 112
accctacgtt accgtgctca a                                              21

<210> SEQ ID NO 113
<211> LENGTH: 21
<212> TYPE: DNA
<213> ORGANISM: Homo sapiens

<400> SEQUENCE: 113
ctgccgggtt acgtcaccta a                                              21

<210> SEQ ID NO 114
<211> LENGTH: 21
<212> TYPE: DNA
<213> ORGANISM: Homo sapiens

<400> SEQUENCE: 114
gtggcccttt atgactatga a                                              21

<210> SEQ ID NO 115
<211> LENGTH: 21
<212> TYPE: DNA
<213> ORGANISM: Homo sapiens

<400> SEQUENCE: 115
ctcgggtgtg ccataataat a                                              21

<210> SEQ ID NO 116
<211> LENGTH: 21
<212> TYPE: DNA
<213> ORGANISM: Homo sapiens

<400> SEQUENCE: 116
tagccgtagt gtaatgattg a                                              21

<210> SEQ ID NO 117
<211> LENGTH: 21
<212> TYPE: DNA
<213> ORGANISM: Homo sapiens

<400> SEQUENCE: 117
ctgggtctgt gagcagttca a                                              21

<210> SEQ ID NO 118
<211> LENGTH: 21
<212> TYPE: DNA
<213> ORGANISM: Homo sapiens

<400> SEQUENCE: 118
cgacatgttc aactactata a                                              21

<210> SEQ ID NO 119
<211> LENGTH: 21
<212> TYPE: DNA
<213> ORGANISM: Homo sapiens

<400> SEQUENCE: 119
tcgggaagct accatttctt a                                              21

<210> SEQ ID NO 120
<211> LENGTH: 21
<212> TYPE: DNA
<213> ORGANISM: Homo sapiens
```

<400> SEQUENCE: 120
aagggttacc ttccagttca a                                              21

<210> SEQ ID NO 121
<211> LENGTH: 21
<212> TYPE: DNA
<213> ORGANISM: Homo sapiens

<400> SEQUENCE: 121
caggttgtcc cacatgtata a                                              21

<210> SEQ ID NO 122
<211> LENGTH: 21
<212> TYPE: DNA
<213> ORGANISM: Homo sapiens

<400> SEQUENCE: 122
tccgacttta tgattatgaa a                                              21

<210> SEQ ID NO 123
<211> LENGTH: 21
<212> TYPE: DNA
<213> ORGANISM: Homo sapiens

<400> SEQUENCE: 123
cagctgggtt tagctacgaa a                                              21

<210> SEQ ID NO 124
<211> LENGTH: 21
<212> TYPE: DNA
<213> ORGANISM: Homo sapiens

<400> SEQUENCE: 124
caagacctgc taagagaatt a                                              21

<210> SEQ ID NO 125
<211> LENGTH: 21
<212> TYPE: DNA
<213> ORGANISM: Homo sapiens

<400> SEQUENCE: 125
cacctacgta tttaagatga a                                              21

<210> SEQ ID NO 126
<211> LENGTH: 21
<212> TYPE: DNA
<213> ORGANISM: Homo sapiens

<400> SEQUENCE: 126
cacgaccaca ttgtccgatt t                                              21

<210> SEQ ID NO 127
<211> LENGTH: 21
<212> TYPE: DNA
<213> ORGANISM: Homo sapiens

<400> SEQUENCE: 127
cagggctgcc atataacctg a                                              21

<210> SEQ ID NO 128
<211> LENGTH: 21
<212> TYPE: DNA
<213> ORGANISM: Homo sapiens

<400> SEQUENCE: 128
cccgcacagg tctttcctta t                                                 21

<210> SEQ ID NO 129
<211> LENGTH: 21
<212> TYPE: DNA
<213> ORGANISM: Homo sapiens

<400> SEQUENCE: 129
ccgctggata tgggacgaac a                                                 21

<210> SEQ ID NO 130
<211> LENGTH: 21
<212> TYPE: DNA
<213> ORGANISM: Homo sapiens

<400> SEQUENCE: 130
cccagtgaga aggctaacaa a                                                 21

<210> SEQ ID NO 131
<211> LENGTH: 21
<212> TYPE: DNA
<213> ORGANISM: Homo sapiens

<400> SEQUENCE: 131
ccgatgttat tagatgttac a                                                 21

<210> SEQ ID NO 132
<211> LENGTH: 21
<212> TYPE: DNA
<213> ORGANISM: Homo sapiens

<400> SEQUENCE: 132
tagacctttc gtagagatgt a                                                 21

<210> SEQ ID NO 133
<211> LENGTH: 21
<212> TYPE: DNA
<213> ORGANISM: Homo sapiens

<400> SEQUENCE: 133
aagaagcagg atgctgatct a                                                 21

<210> SEQ ID NO 134
<211> LENGTH: 21
<212> TYPE: DNA
<213> ORGANISM: Homo sapiens

<400> SEQUENCE: 134
tacgttagaa gagcactgta a                                                 21

<210> SEQ ID NO 135
<211> LENGTH: 21
<212> TYPE: DNA
<213> ORGANISM: Homo sapiens

<400> SEQUENCE: 135
cagcccgagt cccgaggata a                                                 21

<210> SEQ ID NO 136
<211> LENGTH: 21
<212> TYPE: DNA
<213> ORGANISM: Homo sapiens

```
-continued

<400> SEQUENCE: 136
tggcgacatg ttcaactact a                                              21

<210> SEQ ID NO 137
<211> LENGTH: 21
<212> TYPE: DNA
<213> ORGANISM: Homo sapiens

<400> SEQUENCE: 137
cggaaagact acagatctta a                                              21

<210> SEQ ID NO 138
<211> LENGTH: 21
<212> TYPE: DNA
<213> ORGANISM: Homo sapiens

<400> SEQUENCE: 138
aaggctcaac gtataagcga a                                              21

<210> SEQ ID NO 139
<211> LENGTH: 21
<212> TYPE: DNA
<213> ORGANISM: Homo sapiens

<400> SEQUENCE: 139
tagagacaag cgggaaggat a                                              21

<210> SEQ ID NO 140
<211> LENGTH: 21
<212> TYPE: DNA
<213> ORGANISM: Homo sapiens

<400> SEQUENCE: 140
cagaaatagg ttaccggaat t                                              21

<210> SEQ ID NO 141
<211> LENGTH: 21
<212> TYPE: DNA
<213> ORGANISM: Homo sapiens

<400> SEQUENCE: 141
taggtgaatg gcggtcacat a                                              21
```